US006936617B2

(12) United States Patent
Hutchison et al.

(10) Patent No.: US 6,936,617 B2
(45) Date of Patent: Aug. 30, 2005

(54) HETEROARYL SUBSTITUTED FUSED BICYCLIC HETEROARYL COMPOUND AS GABA$_A$ RECEPTOR LIGANDS

(75) Inventors: Alan Hutchison, Madison, CT (US); George Maynard, Clinton, CT (US); Pamela Albaugh, Carmel, IN (US); Linghong Xie, Guilford, CT (US); Jun Yuan, Guilford, CT (US); Scott Mitchell, East Haven, CT (US); Vinod Singh, Kanpur (IN); Manuka Ghosh, Madison, CT (US); Guiying Li, Branford, CT (US); Nian Liu, North Branford, CT (US)

(73) Assignee: Neurogen Corporation, Branford, CT (US)

( * ) Notice: Subject to any disclaimer, the term of this patent is extended or adjusted under 35 U.S.C. 154(b) by 12 days.

(21) Appl. No.: 10/194,852

(22) Filed: Jul. 12, 2002

(65) Prior Publication Data

US 2003/0207885 A1 Nov. 6, 2003

Related U.S. Application Data

(60) Provisional application No. 60/305,533, filed on Jul. 13, 2001.

(51) Int. Cl.[7] .................... C07D 471/04; C07D 487/04; C07D 513/04; A61K 31/437
(52) U.S. Cl. ....................... 514/256; 514/300; 544/333; 546/121
(58) Field of Search .................... 546/121; 544/333; 514/256, 300

(56) References Cited

U.S. PATENT DOCUMENTS

| 6,271,241 B1 | 8/2001 | DeSimone et al. | ......... 514/303 |
| 6,358,949 B1 | 3/2002 | DeSimone et al. | ...... 514/234.5 |
| 6,380,210 B1 | 4/2002 | DeSimone et al. | ......... 514/303 |
| 6,420,365 B1 | 7/2002 | Peterson et al. | ............. 514/248 |

FOREIGN PATENT DOCUMENTS

| WO | WO 96/34866 | * 11/1996 |
| WO | WO 99/37303 | 7/1999 |
| WO | WO 99/47131 | 9/1999 |
| WO | WO 99/47142 | 9/1999 |
| WO | WO 99/47171 | 9/1999 |
| WO | WO 02/050062 A3 | 12/2001 |

OTHER PUBLICATIONS

Cooper et al., The Biochemical Basis of Neuropharmacology 6th ed., (1991), pp. 145–148.
Da–Rocha, et al., J. Psychopharmacology (1997) 11(3) 211–218.
Jones, Jr. et al., J. Het. Chem. (1987), p. 1221.
Huff, et al., JCS Perkin 'Trans. I (1972), p. 2584.
Lee, et al., Alcohol and Alcoholism (1996) 31 Suppl. 27–32.
Mohler et al., Neuroch. Res. (1995) 20(5), pp. 631–636.
Oravcova et al., Journal of Chromatograph B (1996) vol. 677, pp. 1–27.
Remington's Pharmaceutical Sciences, 17th ed., Mack Publishing Co., Easton PA, p. 1418 (1985).
Smith, et al., Am. J. Psychiatry (1998) 155(10) pp. 1339–1345.
Tang, C. C., et al., J. Am. Chem. Soc. (1978), 100, 3918.
Thomas and Tallman J. Bio. Chem. (1981) 156: pp. 9838–9842.
Thomas and Tallman, J. Neurosci. (1983) 3:pp. 433–440.
White and Gurley, NeuroReport (1995) 6: pp. 1313–1316.
White, et al., Receptors and Channels (1995) 3: pp. 1–5.

* cited by examiner

*Primary Examiner*—Deepak Rao
(74) *Attorney, Agent, or Firm*—McDonnell Boehnen Hulbert & Berghoff LLP

(57) ABSTRACT

This invention relates to heteroaryl substituted fused bicyclic heteroaryl compounds, such as heteroaryl substituted imidazopyridines, imidazopyrazines, imidazopyridizines, imidazopyrimidines, and imidazothiazoles, which may be described by Formula I or Formula II:

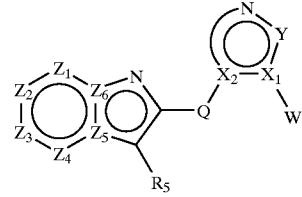

Formula I

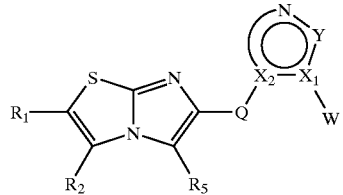

Formula II

The invention is particularly related to such compounds that bind with high selectivity and high affinity to the benzodiazepine site of GABA$_A$ receptors. This invention also relates to pharmaceutical compositions comprising such compounds and to the use of such compounds in treatment of certain central nervous system (CNS) diseases. Processes for preparing compounds of Formula I and Formula II are disclosed.

This invention also relates to the use of benzimidazoles, pyridylimidazoles and related bicyclic heteroaryl compounds of Formula I or Formula II in combination with one or more other CNS agents to potentiate the effects of the other CNS agents. Additionally this invention relates to the use such compounds as probes for the localization of GABA$_A$ receptors in tissue sections.

32 Claims, No Drawings

US 6,936,617 B2

HETEROARYL SUBSTITUTED FUSED BICYCLIC HETEROARYL COMPOUND AS GABA$_A$ RECEPTOR LIGANDS

This application claims the benefit of Provisional Application No. 60/305,533 filed Jul. 31, 2001.

FIELD OF THE INVENTION

This invention relates to heteroaryl substituted fused bicyclic heteroaryl compounds, such as heteroaryl substituted imidazopyridines, imidazopyrazines, imidazopyridizines, imidazopyrimidines, and imidazothiazoles, and more specifically to such compounds that bind with high selectivity and high affinity to the benzodiazepine site of GABA$_A$ receptors. This invention also relates to pharmaceutical compositions comprising such compounds and to the use of such compounds in treatment of certain central nervous system (CNS) diseases. This invention also relates to the use of these heteroaryl substituted imidazopyridines, imidazopyrazines, imidazopyridizines, imidazopyrimidines, and imidazothiazoles compounds and related compounds in combination with one or more other CNS agents to potentiate the effects of the other CNS agents. Additionally this invention relates to the use such compounds as probes for the localization of GABA$_A$ receptors in tissue sections.

BACKGROUND

The GABA$_A$ receptor superfamily represents one of the classes of receptors through which the major inhibitory neurotransmitter, γ-aminobutyric acid, or GABA, acts. Widely, although unequally, distributed throughout the mammalian brain, GABA mediates many of its actions through a complex of proteins called the GABA$_A$ receptor, which causes alteration in chloride conductance and membrane polarization. In addition to being the site of neurotransmitter action, a number of drugs including the anxiolytic and sedating benzodiazepines bind to this receptor. The GABA$_A$ receptor comprises a chloride channel that generally, but not invariably, opens in response to GABA, allowing chloride to enter the cell. This, in turn, effects a slowing of neuronal activity through hyperpolarization of the cell membrane potential.

GABA$_A$ receptors are composed of five protein subunits. A number of cDNAs for these GABA$_A$ receptor subunits have been cloned and their primary structures determined. While these subunits share a basic motif of 4 membrane-spanning helices, there is sufficient sequence diversity to classify them into several groups. To date at least 6α, 3β, 3γ, 1ε, 1δ and 2ρ subunits have been identified. Native GABA$_A$ receptors are typically composed of 2α, 2β, and 1γ. Various lines of evidence (such as message distribution, genome localization and biochemical study results) suggest that the major naturally occurring receptor combinations are $\alpha_1\beta_2\gamma_2$, $\alpha_2\beta_3\gamma_2$, $\alpha_3\beta_3\gamma_2$, and $\alpha_5\beta_3\gamma_2$ (Mohler et al. *Neuroch. Res.* 1995; 20(5):631–36).

The GABA$_A$ receptor binding sites for GABA (2 per receptor complex) are formed by amino acids from the α and β subunits. Amino acids from the α and γ subunits together form one benzodiazepine site per receptor. Benzodiazepines exert their pharmacological actions by interacting with the benzodiazepine binding sites associated with the GABA$_A$ receptor. In addition to the benzodiazepine site (sometimes referred to as the benzodiazepine or BDZ receptor), the GABA$_A$ receptor contains sites of interaction for several other classes of drugs. These include a steroid binding site, a picrotoxin site, and a barbiturate site. The benzodiazepine site of the GABA$_A$ receptor is a distinct site on the receptor complex that does not overlap with the site of interaction for other classes of drugs that bind to the receptor or for GABA (see, e.g., Cooper, et al., The Biochemical Basis of Neuropharmacology, 6$^{th}$ ed., 1991, pp. 145–148, Oxford University Press, New York).

In a classic allosteric mechanism, the binding of a drug to the benzodiazepine site increases the affinity of the GABA receptor for GABA. Benzodiazepines and related drugs that enhance the ability of GABA to open GABA$_A$ receptor channels are known as agonists or partial agonists depending on the level of GABA enhancement. Other classes of drugs, such as β-carboline derivatives, that occupy the same site and negatively modulate the action of GABA are called inverse agonists. A third class of compounds exists which occupy the same site as both the agonists and inverse agonists and yet have little or no effect on GABA activity. These compounds will, however, block the action of agonists or inverse agonists and are thus referred to as GABA$_A$ receptor antagonists.

The important allosteric modulatory effects of drugs acting at the benzodiazepine site were recognized early, and the distribution of activities at different subtype receptors has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have enjoyed long pharmaceutical use as anxiolytics, these compounds are known to exhibit a number of unwanted side effects. These may include cognitive impairment, sedation, ataxia, potentiation of ethanol effects, and a tendency for tolerance and drug dependence.

GABA$_A$ selective ligands may also act to potentiate the effects of certain other CNS active compounds. For example, there is evidence that selective serotonin reuptake inhibitors (SSRIs) may show greater antidepressant activity when used in combination with GABA$_A$ selective ligands than when used alone.

SUMMARY OF THE INVENTION

This invention provides compounds of Formula I and Formula II (shown below), particularly heteroaryl substituted imidazopyridines, imidazopyrazines, imidazopyridizines, imidazopyrimidines, and imidazothiazoles that bind to the benzodiazepine site of GABA$_A$ receptors, including human GABA$_A$ receptors. Preferred compounds of the invention bind with high selectivity and/or high affinity to GABA$_A$ receptors. Preferred compounds act as agonists, antagonists or inverse agonists of such receptors. As such, they are useful in the treatment of various CNS disorders.

The invention further provides compounds pharmaceutical compositions comprising compounds of Formula I and/or Formula II.

The invention provides methods for synthesizing compounds of Formula I and Formula II.

The invention further provides methods of treating patients suffering from certain CNS disorders with an effective amount of a compound of Formula I and/or Formula II. The patient may be a human or other mammal. Treatment of humans, domesticated companion animals (pets) or livestock animals suffering from certain CNS disorders with an effective amount of a compound of the invention is encompassed by the invention.

In a separate aspect, the invention provides methods of potentiating the actions of other CNS active compounds. These methods comprise administering an effective amount of a compound of Formula I and/or Formula II in conjunction with the administration of another CNS active compound.

Additionally this invention relates to the use of compounds of Formula I or Formula II as probes for the localization of GABA$_A$ receptors in tissue sections.

Accordingly an embodiment of the invention is directed to compounds of Formula I

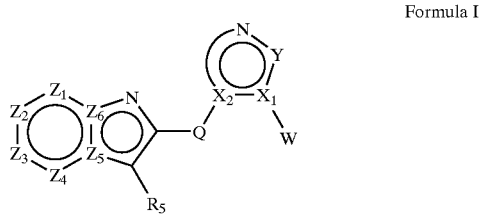

Formula I and the pharmaceutically acceptable salts thereof.

$Z_1$ (in Formula I) is nitrogen or $CR_1$; $Z_2$ is nitrogen or $CR_2$; $Z_3$ is nitrogen or $CR_3$; $Z_4$ is nitrogen or $CR_4$; $Z_5$ is nitrogen or carbon; and $Z_6$ is nitrogen or carbon; provided that no more than two of $Z_1$, $Z_2$, $Z_3$, $Z_4$, $Z_5$, and $Z_6$ are nitrogen.

$R_1$, $R_2$, $R_3$, and $R_4$ are independently selected from:
(i) hydrogen, halogen, hydroxy, nitro, cyano, amino, haloalkyl, and haloalkoxy;
(ii) alkyl, alkoxy, cycloalkyl, alkenyl, alkynyl, (cycloalkyl)alkyl, —NH($R_{10}$), —N($R_{10}$)($R_{11}$), hydroxyalkyl, aminoalkyl, ($R_{10}$)NHalkyl, ($R_{10}$)($R_{11}$)Nalkyl, alkanoyl, alkoxycarbonyl, alkylsulfonyl, alkylsulfinyl, alkylthio, mono- and dialkylaminocarbonyl, heterocycloalkyl, aryl, and heteroaryl, each of which is unsubstituted or substituted with 1, 2, 3, or 4 substituents independently selected from $R_{20}$;
(iii) groups of the formula:

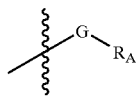

wherein G is alkyl, —O—, —C(=O)—, or —CH$_2$—C(=O)—, and $R_A$ is cycloalkyl, heterocycloalkyl, aryl, or heteroaryl, each of which is unsubstituted or substituted with 1, 2, 3, or 4 of $R_{20}$;
(iv) groups of the formula:

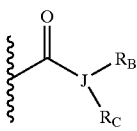

wherein J is N, CH, or C-alkyl, and $R_B$ and $R_C$ are each independently selected from the group consisting of hydrogen, alkyl, alkenyl, alkynyl, alkoxy, cycloalkyl, (cycloalkyl)alkyl, heterocycloalkyl, aryl, arylalkyl, alkanoyl, heteroaryl, and mono and dialkylaminoalkyl, each of which is unsubstituted or substituted with 1 or 2 substituents independently chosen from halogen, hydroxy, cyano, amino, nitro, alkoxy, haloalkoxy, alkyl and haloalkyl; or $R_B$ and $R_C$ and the atom to which they are attached form a 4- to 10-membered monocyclic or bicyclic ring, comprising: a) 0, 1, 2 or 3 double bonds, and b) 0, 1, 2 or 3 of oxo, O, S, SO, SO$_2$, or N—$R_D$, wherein $R_D$ is (1)hydrogen; or (2) Ar$_1$, alkyl, cycloalkyl, heterocycloalkyl, or Ar$_1$alkyl; wherein Ar$_1$ is aryl or heteroaryl, each of which is unsubstituted or substituted with 1 or 2 substituents independently chosen from halogen, hydroxy, cyano, amino, nitro, alkoxy, and alkyl; and
(v) —OC(=O)$R_E$, —C(=O)NH$_2$, —C(=O)NHR$_E$, —C(=O)NR$_E$R$_F$, —S(O)$_n$R$_E$, —S(O)$_n$NH$_2$, —S(O)$_n$NHR$_E$, —S(O)$_n$NR$_E$R$_F$, —NHC(=O)R$_E$, —C(=NR$_E$)R$_F$, —HC=N—OH, —HC=N(alkoxy), —HC=N(alkyl), —NR$_E$C(=O)R$_F$, —NHS(O)$_n$R$_E$, and —NR$_E$S(O)$_n$R$_F$, wherein n is 0, 1 or 2; R$_E$ and R$_F$ are independently selected at each occurrence from alkyl, cycloalkyl, heterocycloalkyl, alkoxy, mono- and dialkylamino, aryl, and heteroaryl, each of which is unsubstituted or substituted with 1, 2, or 3 substituents independently selected from R$_{30}$.

$R_5$ represents: (i) hydrogen, halogen, cyano, or haloalkyl; (ii) alkyl, cycloalkyl, (cycloalkyl)alkyl, each of which comprises from 0 to 3 double bonds and/or from 0 to 3 triple bonds, and is unsubstituted or substituted with 1, 2, or 3 substituents independently selected from $R_{30}$; or (iii) aryl, arylalkyl, heteroaryl, or heteroarylalkyl, each of which is unsubstituted or substituted with 1, 2, or 3 substituents independently selected from the group consisting of haloalkyl, amino, —NH($R_{10}$), —N($R_{10}$)($R_{11}$), carboxamido, ($R_{10}$)NHcarbonyl, ($R_{10}$)($R_{11}$)Ncarbonyl, halogen, hydroxy, nitro, cyano, amino, alkyl, alkoxy, alkoxy substituted with amino or mono- or dialkylamino, cycloalkyl, cycloalkylalkyl, cycloalkylalkoxy, cycloalkyloxy, heterocycloalkyl, alkenyl, alkynyl, haloalkyl, haloalkoxy, aminoalkyl, and mono- and dialkylaminoalkyl.

$R_{10}$ and $R_{11}$ are independently selected from the group consisting of alkyl, alkenyl, alkynyl, alkoxy, cycloalkyl, cycloalkylalkyl, aryl, arylalkyl, alkanoyl, and mono and dialkylaminoalkyl.

Q represents —C($R_6$)($R_7$), —N(alkyl)— or oxygen, wherein $R_6$ and $R_7$ independently represent hydrogen, fluorine, or alkyl; with the proviso that Q is not oxygen when $X_2$ is nitrogen.

$R_{20}$ is independently selected at each occurrence from: halogen, hydroxy, nitro, cyano, amino, alky, alkoxy, alkoxy substituted with amino or mono- or dialkylamino, cycloalkyl, cycloalkylalkyl, cycloalkylalkoxy, cycloalkyloxy, alkenyl, alkynyl, haloalkyl, haloalkoxy, mono- and dialkylamino, aminoalkyl, and mono- and dialkylaminoalkyl.

$R_{30}$ is independently selected at each occurrence from: halogen, hydroxy, nitro, cyano, amino, alkyl, alkoxy; alkoxy substituted with amino or mono- or dialkylamino, cycloalkyl, cycloalkylalkyl, cycloalkylalkoxy, cycloalkyloxy, heterocycloalkyl, alkenyl, alkynyl, haloalkyl, haloalkoxy, mono- and dialkylamino, aminoalkyl, and mono- and dialkylaminoalkyl.

The group:

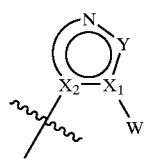

represents a 5 to 7 membered heteroaryl group containing from 1 to 4 heteroatoms independently selected from nitrogen, sulfur, and oxygen, unsubstituted or substituted at each carbon atom by R, and unsubstituted or substituted at each nitrogen atom available for substitution by R'.

R, in the above group, is independently chosen at each occurrence from halogen, amino, alkyl, alkenyl, alkynyl, alkoxy, cycloalkyl, (cycloalkyl)alkyl, haloalkyl, haloalkoxy, carboxamido, and 3- to 7-membered carbocyclic and heterocyclic rings, each of which is unsubstituted or substituted with one or more substituents independently selected from halogen, oxo, hydroxy, alkyl, and alkoxy.

R' is independently chosen at each occurrence from alkyl, cycloalkyl, cycloalkyl(alkyl), and 3- to 7-membered carbocyclic and heterocyclic rings, each of which unsubstituted or substituted with one or more substituents independently selected from halogen, oxo, hydroxy, alkyl, and alkoxy.

$X_1$ and $X_2$ independently represent nitrogen, carbon or CH.

Y is nitrogen, carbon, —CH—, —CH$_2$—, or absent.

W represents aryl or heteroaryl, each of which is unsubstituted or substituted with from 0 to 4 groups independently selected from $R_{30}$, —C(=O)OR$_E$, —C(=O)NR$_E$, —C(O)R$_E$, —OR$_E$ and —S(O)$_m$R$_E$, wherein m is 0, 1, or 2.

In another embodiment the invention provides compounds of Formula II:

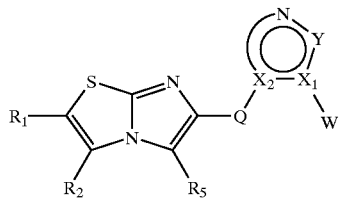

Formula II and the pharmaceutically acceptable salts thereof.

$R_1$ and $R_2$, in Formula II, are independently selected from hydrogen, halogen, nitro, cyano, haloalkyl, haloalkoxy, alkyl, alkoxy, cycloalkyl, alkenyl, alkynyl, (cycloalkyl)alkyl, mono and dialkylamino, and aminoalkyl.

The remaining variables shown in Formula II, e.g. Q, $R_5$, W, $X_1$, $X_2$, and Y, carry the definitions set forth above for compounds of Formula I.

DETAILED DESCRIPTION

Chemical Description and Terminology

Prior to setting forth the invention in detail, it may be helpful to provide definitions of certain terms to be used herein. Compounds of the present invention are generally described using standard nomenclature. Certain compounds are described herein using a general formula that includes variables. Unless otherwise specified, each variable within such a formula is defined independently of other variables.

Formula I includes, but is not limited to the subformulae exemplified as Formula III–Formula XXIV and their pharmaceutically acceptable acid and base addition salts. Formula II includes, but is not limited to the subformulae exemplified as Formula XV–Formula XXVI and their pharmaceutically acceptable acid and base addition salts.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. As used herein, "pharmaceutically acceptable salts" refers to derivatives of the disclosed compounds wherein the parent compound is modified by making acid or base salts thereof. Those skilled in the art will recognize a wide variety of non-toxic pharmaceutically acceptable addition salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, hydroiodic, sulfuric, sulfamic, sulfinic, phosphoric, nitric and the like; and the salts prepared from organic acids such as alkanoic such as acetic, HOOC—(CH$_2$)n-ACOOH where n is 0–4, and the like, tartaric, maleic, propionic, succinic, glycolic, stearic, lactic, malic, tartaric, citric, ascorbic, pamoic, malefic, hydroxymaleic, phenylacetic, glutamic, benzoic, salicylic, sulfanilic, 2-acetoxybenzoic, fumaric, toluenesulfonic, methanesulfonic, ethanesulfonic, ethane disulfonic, oxalic, isethionic, HOOC—(CH$_2$)n-COOH where n is 0–4, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985).

The invention includes hydrates of compounds of Formula I and Formula II.

The invention includes all crystalline forms of the compounds of Formula I and Formula II. Certain crystalline forms may be preferred.

The present invention also encompasses the acylated prodrugs of the compounds of Formula I and Formula II. Those skilled in the art will recognize various synthetic methodologies that may be employed to prepare non-toxic pharmaceutically acceptable addition salts and acylated prodrugs of the compounds encompassed by Formula I and Formula II. The invention further encompasses all enantiomers and diastereomers of the disclosed compounds. Those of ordinary skill in the art will readily recognize methods by which mixtures of enantiomers and diasteromers may be resolved. The definitions of Formula I and Formula II as used in herein include possible isomers, such as tautomers and rotamers.

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

When any variable occurs more than one time in any constituent or formula for a compound, its definition at each occurrence is independent of its definition at every other occurrence. Thus, for example, if a group is shown to be substituted with 0 to 3 R*, (where R* indicates any variable group such as R) then said group may optionally be substituted with up to three R* groups and R* at each occurrence is selected independently from the definition of R*. Also, combinations of substituents and/or variables are permissible only if such combinations result in stable compounds.

When any group, such as an aryl group, heteroaryl group, carbocyclic group, heterocyclic group, or monocylic or bicyclic ring is said to be "substituted by one or more substituents" that group may contain from 1 to the maximum number of substituents allowable without exceeding the valency of the atoms of the substituted group. Preferably such groups are substituted from 1 to 4 substituents, and more preferably such groups are substituted with from 1 to 3 substituents. Preferably such groups are not substituted with more that one oxo substituent.

A dash "-" that is not between two letters or symbols is used to indicate a point of attachment for a substituent. For example —C(=O)NH$_2$ is attached through the carbon atom.

As used herein, "alkyl" is intended to include both branched and straight-chain saturated aliphatic hydrocarbon groups, having the specified number of carbon atoms. Thus, the term C$_1$–C$_6$ alkyl as used herein includes alkyl groups consisting of 1 to 6 carbon atoms. When C$_1$–C$_n$alkyl is used herein in conjunction with another group, for example, arylC$_1$–C$_4$alkyl, the indicated group, in this case aryl, is attached by an alkyl chain having the specified number of carbon atoms, in this case from 1 to 4 carbon atoms. Examples of alkyl include, but are not limited to, methyl, ethyl, n-propyl, i-propyl, n-butyl, s-butyl, t-butyl, n-pentyl, and s-pentyl. Preferred alkyl groups are C$_1$–C$_6$ and C$_1$–C$_4$ alkyl groups.

"Alkenyl" is intended to include hydrocarbon chains of either a straight or branched configuration comprising one or more unsaturated carbon-carbon bonds, which may occur in any stable point along the chain, such as ethenyl and propenyl.

"Alkynyl" is intended to include hydrocarbon chains of either a straight or branched configuration comprising one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkanoyl" represents an alkyl group as defined above with the indicated number of carbon atoms attached through a carbonyl bridge.

"Alkoxycarbonyl" indicates a group of the formula:

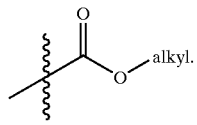

As used herein, the term "mono- and di-alkylamino" includes secondary (monoalkylamino) or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, methyl-propyl-amino. The term "mono- and di-alkylaminoalkyl" is used to indicate and alkyl group, as described above, substituted by a mono- or di-alkylamino group, as described above. The term "mono- and di-alkylaminocarbonyl" is used to indicate a mono- or di-alkylamino group, as described above, attached through a carbonyl bridge.

As used herein, the term "aminoalkyl" indicates an alkyl group substituted at the terminal position by NH$_2$, e.g. a 3-propylamine group.

As used herein, the term "alkylsulfinyl" includes those groups having one or more sulfoxide (SO) linkage groups and typically from 1 to about 8 carbon atoms, more typically 1 to about 6 carbon atoms.

As used herein, the term "alkylsulfonyl" includes those groups having one or more sulfonyl (SO$_2$) linkage groups and typically from 1 to about 8 carbon atoms, more typically 1 to about 6 carbon atoms.

As used herein, the term "alkylthio" includes those groups having one or more thioether linkages and preferably from 1 to about 8 carbon atoms, more typically 1 to about 6 carbon atoms.

As used herein, the term "aryl" indicates aromatic groups containing only carbon in the aromatic ring. Such aromatic groups may be further substituted with carbon or non-carbon atoms or groups. Typical aryl groups contain 1 to 3 separate, fused, or pendant rings and from 6 to about 18 ring atoms, without heteroatoms as ring members. Specifically preferred aryl groups include phenyl, naphthyl, including 1-naphthyl and 2-naphthyl, and biphenyl.

"Carboxamido" indicates a group of the formula —C(=O)NH$_2$.

"Cycloalkyl" is intended to include saturated hydrocarbon ring groups, having the specified number of carbon atoms, usually from 3 to about 8 ring carbon atoms. Preferred cycloalkyl groups have from 3 to 7 ring carbon atoms. Examples of cycloalkyl groups include cyclopropyl, cyclobutyl, cyclopentyl, or cyclohexyl and bridged or caged saturated ring groups such as norborane or adamantane and the like.

In the term "(cycloalkyl)alkyl" cycloalkyl and alkyl are as defined above, and the point of attachment is on the alkyl group. This term encompasses, but is not limited to, cyclopropylmethyl, cyclohexylmethyl, and cyclohexylmethyl. Likewise, in the term "(cycloalkyl)alkoxy", cycloalkyl and alkoxy are as define above, and the point of attachment in the oxygen of the alkoxy group. The term "cycloalkyloxy" indicates a cycloalkyl group, as defined above, attached through an oxygen bridge.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

As used herein, the terms "heteroaryl" is intended to indicate a stable 5- to 7-membered monocyclic or bicyclic or 7- to 10-membered bicyclic heterocyclic ring which contains at least 1 aromatic ring that contains from 1 to 4 heteroatoms selected from N, O, and S, with remaining ring atoms being carbon. When the total number of S and O atoms in the heteroaryl group exceeds 1, it is understood that these heteroatoms are not adjacent to one another. It is preferred that the total number of S and O atoms in the heterocycle is not more than 1, 2, or 3, more typically 1 or 2. It is particularly preferred that the total number of S and O atoms in the aromatic heterocycle is not more than 1.

Preferred heteroaryl groups include imidazolyl, pyrfoyl, pyridyl, thiazolyl, pyrazolyl, thiazolyl, pyrimidinyl, and thienyl.

The term "heterocycloalkyl" is used to indicate saturated cyclic groups containing from 1 to about 3 heteroatoms selected from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, and pyrrolidinyl groups.

As used herein, the term "heterocyclic group" is intended to include 3 to 7 membered saturated, partially unsaturated, or aromatic monocyclic groups having at least one atom selected from N, O or S. The remaining ring atoms are carbon. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen atom in the heterocycle may optionally be quaternized. It is preferred that the total number of heteroatoms in the heterocyclic groups is not more than 4 and that the total number of S and O atoms in the heterocyclic group is not more than 2, more preferably not more than 1.

Additional examples of heteroaryl and heterocyclic groups include, but are not limited to, pyrimidinyl, pyridyl, quinolinyl, benzothienyl, indolyl, pryidazinyl, pyazinyl, isoindolyl, isoquinolyl, quinazolinyl, quinoxalinyl, phthalazinyl, imidazolyl, isoxazolyl, pyrazolyl, oxazolyl, thienyl, thiazolyl, indolizinyl, indazolyl, benzothiazolyl, benzimidazolyl, benzofuranyl, benzoisoxolyl, dihydrobenzodioxinyl, furanyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pleridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide.

The term "oxo" indicates a carbonyl group. When an oxo group appears as a substituent the allowed valence of the substituted position is not exceeded.

GABA Receptor Ligands

The invention includes certain compounds and pharmaceutically acceptable salts of Formula I (shown above) in which the variables, e.g. $R_1$, $R_2$, $R_3$, $R_4$, Q, and W, carry the following definitions:

$R_1$, $R_2$, $R_3$, and $R_4$ are independently selected from:

(i) hydrogen, halogen, hydroxy, nitro, cyano, amino, halo($C_1$–$C_6$) alkyl, and halo($C_1$–$C_6$)alkoxy, (ii) ($C_1$–$C_6$)alkyl, ($C_1$–$C_6$)alkoxy, ($C_3$–$C_8$)cycloalkyl, ($C_2$–$C_6$)alkenyl, ($C_2$–$C_6$)alkynyl, (($C_3$–$C_8$)cycloalkyl)($C_1$–$C_4$)alkyl, —NH($R_{10}$), —N($R_{10}$)($R_{11}$), hydroxy($C_1$–$C_6$)alkyl, amino($C_1$–$C_6$)alkyl, ($R_{10}$)NH, ($C_1$–$C_6$)alkyl, ($R_{10}$)($R_{11}$)N($C_1$–$C_6$)alkyl, ($C_1$–$C_6$)alkanoyl, ($C_1$–$C_6$)alkoxycarbonyl, ($C_1$–$C_6$)alkylsulfonyl, ($C_1$–$C_6$)alkylsulfinyl, ($C_1$–$C_6$)alkylthio, mono- and di($C_1$–$C_6$)alkylaminocarbonyl, and 3- to 8-membered heterocycloalkyl, aryl, and heteroaryl, each of which is unsubstituted or substituted with 1, 2, 3, or 4 substituents independently selected from $R_{20}$;

(iii) groups of the formula:

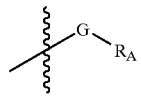

wherein G is ($C_1$–$C_6$)alkyl, —O—, —C(=O)—, or —CH$_2$—C(=O)—, and $R_A$ is 3- to 8-membered cycloalkyl, heterocycloalkyl, aryl, or heteroaryl, each of which is unsubstituted or substituted with 1, 2, 3, or 4 of $R_{20}$;

(iv) groups of the formula:

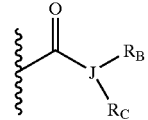

wherein J is N, CH, or C—($C_1$–$C_6$)alkyl and $R_B$ and $R_C$ are each independently selected from the group consisting of hydrogen, ($C_1$–$C_6$)alkyl, ($C_2$–$C_6$)alkenyl, ($C_2$–$C_6$)alkynyl, ($C_1$–$C_6$)alkoxy, ($C_3$–$C_8$)cycloalkyl, ($C_3$–$C_8$cycloalkyl)($C_1$–$C_4$)alkyl, 3- to 8-membered heterocycloalkyl, aryl, aryl ($C_1$–$C_4$)alkyl, ($C_1$–$C_6$)alkanoyl, 3- to 8-membered heteroaryl, and mono and di($C_1$–$C_6$)alkylamino($C_1$–$C_6$) alkyl, each of which is unsubstituted or substituted with 1 or 2 substituents independently chosen from halogen, hydroxy, cyano, amino, nitro, $C_1$–$C_6$alkoxy, halo($C_1$–$C_6$)alkoxy, $C_1$–$C_6$alkyl and halo($C_1$–$C_6$)alkyl; or $R_B$ and $R_C$ and the atom to which they are attached form a 4- to 10-membered monocyclic or bicyclic ring, comprising: a) 0, 1, 2 or 3 double bonds, and b) 0, 1, 2 or 3 of oxo, O, S, SO, $SO_2$, or N—$R_D$, wherein $R_D$ is (1) hydrogen; or (2) $Ar_1$, ($C_1$–$C_6$) alkyl, ($C_3$–$C_8$)cycloalkyl, 3- to 8-membered heterocycloalkyl, or Ar₁(C₁–C₆)alkyl wherein Ar₁ is aryl or heteroaryl, each of which is unsubstituted or substituted with 1 or 2 substituents independently chosen from halogen, hydroxy, cyano, amino, nitro, C₁–C₆alkoxy, and C₁–C₆alkyl; and (v) —OC(=O)R$_E$, —C(=O)NH₂, —C(=O)NHR$_E$, —C(=O)NR$_E$R$_F$, —S(O)$_n$R$_E$, —S(O)$_n$NH₂, —S(O)$_n$NHR$_E$, —S(O)$_n$NR$_E$R$_F$, —NHC(=O)R$_E$, —C(=NR$_E$)R$_F$, —HC=N—OH, —HC=N(C₁–C₆alkoxy), —HC=N(C₁–C₆alkyl), —NR$_E$C(=O)R$_F$, —NHS(O)$_n$R$_E$, and —NR$_E$S(O)$_n$R$_F$, wherein n is 0, 1 or 2, where R$_E$ and R$_F$ are independently selected at each occurrence from (C₁–C₆) alkyl, (C₃–C₈)cycloalkyl, 3- to 8-membered heterocycloalkyl, (C₁–C₆)alkoxy, mono- and di(C₁–C₆) alkylamino, aryl, and 3- to 8-membered heteroaryl, each of which is unsubstituted or substituted with 1, 2, or 3 substituents independently selected from R₃₀.

R₅ represents: (i) hydrogen, halogen or cyano; (ii) (C₁–C₆)alkyl, (C₃–C₈)cycloalkyl, (C₃–C₈cycloalkyl) (C₁–C₄)alkyl, or an analogue of the foregoing that comprises from 1 to 3 double bonds and/or from 1 to 3 triple bonds, each of which is unsubstituted or substituted with 1, 2, or 3 substituents independently selected from R₃₀; or (iii) 3- to 8-membered aryl, 3- to 8-membered aryl (C₁–C₄)alkyl, 3- to 8-membered heteroaryl, or 3- to 8-membered heteroaryl(C₁–C₄)alkyl, each of which is unsubstituted or substituted with 1, 2, or 3 substituents independently selected from the group consisting of halo (C₁–C₆alkyl, amino, —NHR₁₀), —NR₁₀)(R₁₁), carboxamido, (R₁₀)NHcarbonyl, (R₁₀)(R₁₁)Ncarbonyl, halogen, hydroxy, nitro, cyano, amino, (C₁–C₆)alkyl, (C₁–C₆)alkoxy, (C₁–C₆)alkoxy substituted with amino or mono- or di(C₁–C₆)alkylamino, (C₃–C₈)cycloalkyl, (C₃–C₈)cycloalkyl(C₁–C₄)alkyl, (C₃–C₈)cycloalkyl(C₁–C₄) alkoxy, heterocyclo(C₁–C₄)alkyl, (C₂–C₆)alkenyl, (C₂–C₆) alkynyl, halo(C₁–C₆)alkyl, halo(C₁–C₆)alkoxy, amino (C₁–C₆)alkyl, and mono- and di(C₁–C₆)alkylamino(C₁–C₆) alkyl.

R₁₀ and R₁₁ are independently selected from the group consisting of (C₁–C₆)alkyl, (C₂–C₆)alkenyl, (C₁–C₆)alkoxy, (C₃–C₈)cycloalkyl, (C₃–C₈)cycloalkylalkyl, aryl, aryl (C₁–C₆)alkyl, (C₁–C₆)alkanoyl, and mono and di(C₁–C₆) alkylaminoalkyl.

R₂₀ is independently selected at each occurrence from the group consisting of halogen, hydroxy, nitro, cyano, amino, (C₁–C₆)alkyl, (C₁–C₆)alkoxy, (C₁–C₆)alkoxy substituted with amino or mono- or di(C₁–C₆)alkylamino, (C₃–C₈) cycloalkyl, (C₃–C₈)cycloalkyl(C₁–C₄)alkyl, (C₃–C₈) cycloalkyl(C₁–C₄)alkoxy, (C₂–C₆)alkenyl, (C₂–C₆)alkynyl, halo(C₁–C₆)alkyl, halo(C₁–C₆)alkoxy, mono- and di(C₁–C₆)alkylamino, amino(C₁–C₆)alkyl, and mono- and di(C₁–C₆)alkylamino(C₁–C₆)alkyl.

R₃₀ is independently selected at each occurrence from halogen, hydroxy, nitro, cyano, amino, (C₁–C₆)alkyl, (C₁–C₆)alkoxy, (C₁–C₆)alkoxy substituted with amino or mono- or di(C₁–C₆)alkylamino, (C₃–C₈)cycloalkyl, (C₃–C₈)cycloalkyl(C₁–C₄)alkyl, (C₃–C₈)cycloalkyl(C₁–C₄) alkoxy, 3- to 8-membered heterocycloalkyl, (C₂–C₆)alkenyl, (C₂–C₆)alkynyl, halo(C₁–C₆)alkyl, halo(C₁–C₆)alkoxy, mono- and di(C₁–C₆)alkylamino, amino(C₁–C₆)alkyl, and mono- and di(C₁–C₆)alkylamino(C₁–C₆)alkyl.

Q represents C(R₆)(R₇), N(C₁–C₆alkyl) or oxygen, wherein R₆ and R₇ independently represent hydrogen, fluorine, or C₁–C₆alkyl; with the proviso that Q is not oxygen when X₂ is nitrogen.

R is independently chosen at each occurrence from halogen, amino, C₁–C₆alkyl, (C₂–C₆)alkenyl, (C₂–C₆) alkynyl, C₁–C₆alkoxy, (C₃–C₈)cycloalkyl, (C₃–C₈cycloalkyl)(C₁–C₄)alkyl, halo(C₁–C₆)alkyl, haloalkoxy, carboxamido, and 3- to 7-membered carbocyclic and heterocyclic rings, each of which is unsubstituted substituted with from 1 to 4 substituents independently selected from halogen, oxo, hydroxy, C₁–C₄alkyl, and C₁–C₄alkoxy.

R' is independently chosen at each occurrence from C₁–C₆alkyl, C₃–C₈cycloalkyl, C₃–C₈cycloalkyl (C₁–C₄alkyl), and 3- to 7-membered carbocyclic and heterocyclic rings, each of which is unsubstituted or substituted with from 1 to 4 substituents independently selected from halogen, oxo, hydroxy, C₁–C₄alkyl, and C₁–C₄alkoxy.

W represents 3- to 8-membered aryl or heteroaryl, each of which is unsubstituted or substituted with from 1 to 4 groups independently selected from R₃₀, —C(=O)OR$_E$, —C(=O) NR$_E$, —C(O)R$_E$, —OR$_E$ and —S(O)$_m$R$_E$, wherein im is 0, 1, or 2.

Such compounds will be referred to as compounds of Formula III. Variables that are not specifically defined in Formula III, e.g. R₅, carry the values set forth in Formula I.

The invention further includes compounds and salts of Formula IV

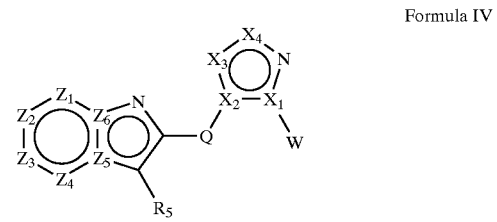

Formula IV wherein X₃ and X₄ are independently selected from the group consisting of CH, CR, N, O, S, NH, and N(C₁–C₆) alkyl provided that at least one of X₁, X₂, X₃, and X₄ is CH or CR.

R in Formula IV is independently chosen at each occurrence from: halogen, amino, (C₁–C₆)alkyl, (C₁–C₆)alkoxy, (C₃–C₈)cycloalkyl, (C₃–C₈)cycloalkyl(C₁–C₆)alkyl, (C₂–C₆)alkenyl, (C₂–C₆)alkynyl, halo(C₁–C₆)alkyl, halo (C₁–C₆)alkoxy, carboxamido, and 3- to 7-membered carbocyclic or heterocyclic rings, each of which is unsubstituted or substituted with from 1 to 4 substituents independently selected from halogen, oxo, hydroxy, (C₁–C₄) alkyl, and —O(C₁–C₄alkyl).

The remaining variables shown in Formula IV, e.g., Z₁–Z₆, R₅, and Q carry the definitions given for compounds of Formula III.

The invention includes compounds and salts of Formula IV in which:

Z₁ is CR₁, Z₂ is CR₂, Z₃ is CR₃, and Z₄ is nitrogen;
Z₁ is CR₁, Z₂ is CR₂, Z₃ is nitrogen, and Z₄ is CR₄;
Z₁ is CR₁, Z₂ is nitrogen, Z₃ is CR₃ and Z₄ is CR₄; or in which Z₁ is nitrogen, Z₂ is CR₂, Z₃ is CR₃ and Z₄ is CR₄.

The invention includes compounds and salts of Formula IV in which X₂ is carbon and Q is oxygen. The invention also includes compounds and salts of Formula IV in which X₂ is carbon and Q is —NH—, or —N(C₁–C₆alkyl)—. The invention further includes compounds and salts of Formula IV in which Q is C(R₆)(R₇).

The invention is further directed to compounds of Formula V–Formula XIV shown in Table I. The variables shown in Formula V–Formula XIV, e.g. Z₁–Z₆, Q, W, R, and R' carry the definitions set forth in Formula III. In certain preferred compounds of Formula V–Formula X and Formula XII–Formula XIV these variables carry the definitions set forth in Formula IV.

TABLE I

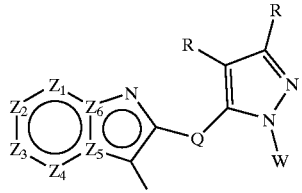

Formula V

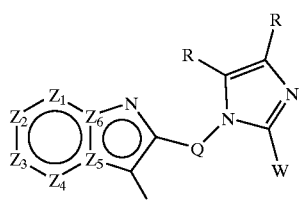

Formula VI

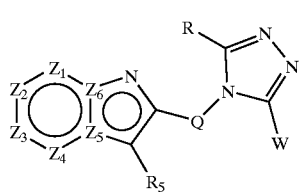

Formula VII

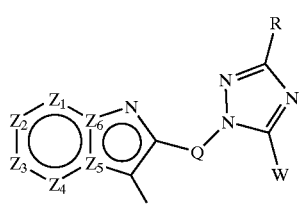

Formula VIII

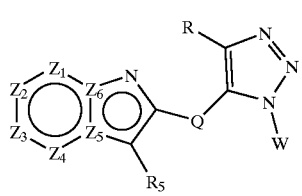

Formula IX

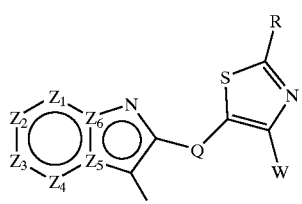

Formula X

TABLE I-continued

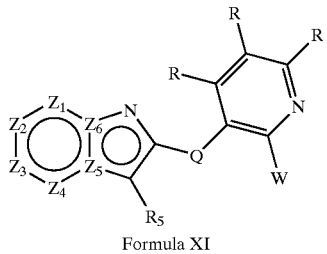

Formula XI

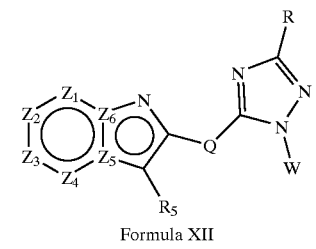

Formula XII

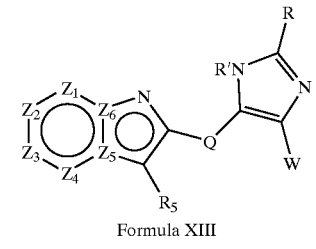

Formula XIII

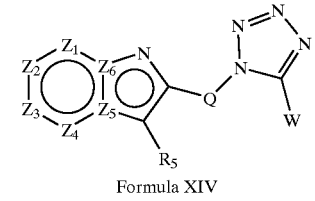

Formula XIV

The invention includes compounds and salts of Formula V–Formula XIV in which Q is $C(R_6)(R_7)$.

The invention also pertains to compounds of Formula V–Formula XIV in which Q is $C(R_6)(R_7)$; R is independently selected from the group consisting of: (i) hydrogen, halogen, $(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_1-C_6)$alkyl, halo$(C_1-C_6)$alkoxy; and (ii) phenyl and pyridyl, each of which is unsubstituted or substituted with from 1 to 3 substituents independently chosen from halogen, hydroxy, $C_1-C_4$alkyl, and $C_1-C_4$alkoxy; and R' is independently chosen at each occurrence from $C_1-C_6$alkyl, $C_3-C_8$cycloalkyl, and $C_3-C_8$cycloalkyl$(C_1-C_4$alkyl$)$.

$R_1$, $R_2$, $R_3$, and $R_4$ are independently selected from:
(i) hydrogen, halogen, hydroxy, nitro, cyano and amino;
(ii) $(C_1-C_6)$alkyl, $(C_1-C_6)$alkoxy, $(C_1-C_6)$alkanoyl, $(C_1-C_6)$alkyl ether, $(C_3-C_8)$cycloalkyl, $(C_3-C_8)$cycloalkyl$(C_1-C_6)$alkyl, $(C_2-C_6)$alkenyl, $(C_2-C_6)$alkynyl, 3- to 8-membered heterocycloalkyl, 3- to 8-membered heteroaryl, halo$(C_1-C_6)$alkyl, halo$(C_1-C_6)$alkoxy, mono and di$(C_1-C_6)$alkylamino, amino$(C_1-C_6)$alkyl, and mono- and di$(C_1-C_6)$alkylamino$(C_1-C_6)$alkyl, each of which is unsubstituted or substituted with 1 or substituents independently selected from hydroxy, halogen, $(C_1-C_6)$alkyl, $(C_1-C_6)$alkoxy, halo$(C_1-C_6)$alkyl, halo$(C_1-C_6)$alkoxy; and (iii) groups of the formula

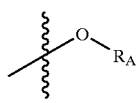

wherein $R_A$ is 5- to 7-membered cycloalkyl, heterocycloalkyl, aryl or heteroaryl, each of which is unsubstituted or substituted with 1 or 2 substituents independently selected from hydroxy, halogen, $(C_1-C_6)$alkyl, halo$(C_1-C_6)$alkyl, $(C_1-C_6)$alkoxy, halo$(C_1-C_6)$alkoxy.

$R_5$, for these embodiments of the invention, represents hydrogen, halogen, $(C_1-C_6)$alkyl, $(C_3-C_8)$cycloalkyl, $(C_3-C_8)$cycloalkyl$(C_1-C_6)$alkyl, phenyl, benzyl, thiophenyl, thiazolyl, pyridyl, imidazolyl, pyrazolyl, or pyrimidinyl.

$R_6$ and $R_7$ independently represent hydrogen, fluorine, or $C_1-C_6$ alkyl.

W represents phenyl, thienyl, thiazolyl, pyridyl, imidazolyl, pyrazolyl, isoxazolyl, or pyrimidinyl, each of which is unsubstituted or substituted with from 1 to 4 groups independently selected from $R_{30}$. $R_{30}$ carries the definition set forth for compounds and salts of Formula III.

The invention is further directed to compounds and pharmaceutically acceptable salts of Formula XV–Formula XXIV shown in Table II. The variables shown in Formula XV–Formula XXIV carry the definitions set forth in Formula IV.

TABLE II

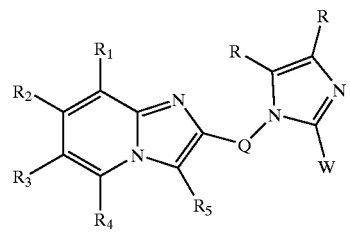

Formula XV

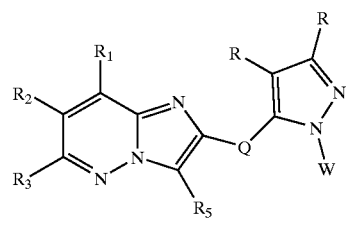

Formula XVII

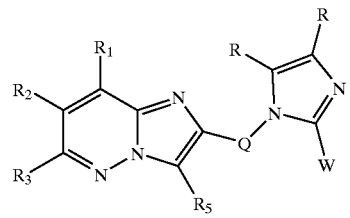

Formula XVIII

TABLE II-continued

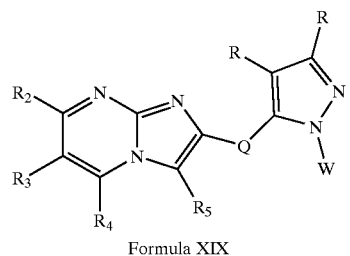

Formula XIX

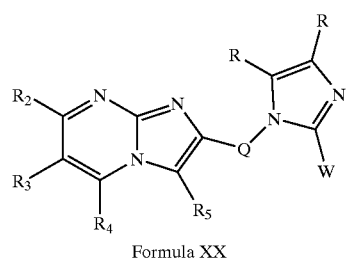

Formula XX

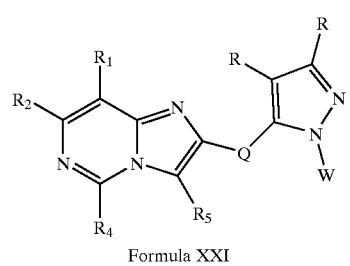

Formula XXI

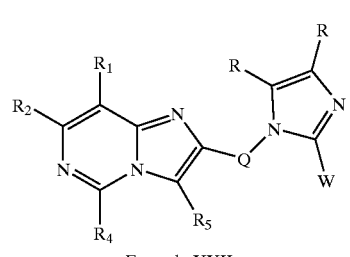

Formula XXII

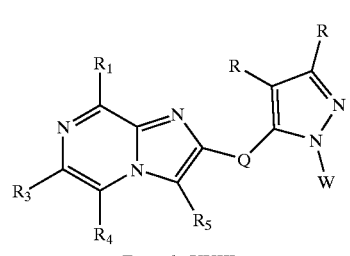

Formula XXIII

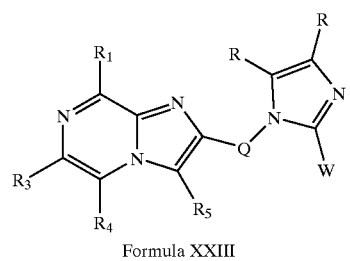

Formula XXIII

TABLE II-continued

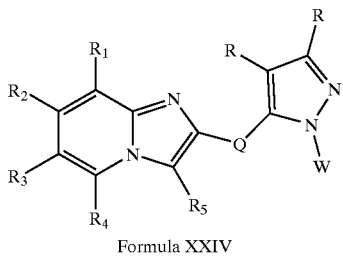

Formula XXIV

Preferred compounds and salts of Formula XV–Formula XXIV are those wherein Q is $C(R_6)(R_7)$.

Other preferred compounds and salts of Formula XV–Formnula XXIV are those wherein Q is $C(R_6)(R_7)$; and R is independently selected from the group consisting of (i) hydrogen, halogen, $(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_1-C_6)$alkyl and halo$(C_1-C_6)$alkoxy, and (ii) phenyl and pyridyl, each of which is unsubstituted or substituted with from 1 to 3 substituents independently chosen from halogen, hydroxy, $C_1-C_4$alkyl, and $C_1-C_4$alkoxy.

$R_1$, $R_2$, $R_3$, and $R_4$ in these embodiments of the invention are independently selected from:

(i) hydrogen, halogen, hydroxy, nitro, cyano and amino;
(ii) $(C_1-C_6)$alkyl, $(C_1-C_6)$alkoxy, $(C_1-C_6)$alkanoyl, $(C_1-C_6)$alkyl ether, $(C_3-C_8)$cycloalkyl, $(C_3-C_8)$cycloalkyl$(C_1-C_6)$alkyl, $(C_2-C_6)$alkenyl, $(C_2-C_6)$alkynyl, 3- to 8-membered heterocycloalkyl, 3- to 8-membered heteroaryl, halo$(C_1-C_6)$alkyl, halo$(C_1-C_6)$alkoxy, mono and di$(C_1-C_6)$alkylamino, amino$(C_1-C_6)$alkyl, and mono- and di$(C_1-C_6)$alkylamino$(C_1-C_6)$alkyl, each of which is unsubstituted or substituted with 1 or substituents independently selected from hydroxy, halogen, $(C_1-C_6)$alkyl, $(C_1-C_6)$alkoxy, halo$(C_1-C_6)$alkyl, halo$(C_1-C_6)$alkoxy; and
(iii) groups of the formula

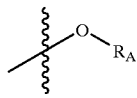

wherein $R_A$ is 5- to 7-membered cycloalkyl, heterocycloalkyl, aryl or heteroaryl, each of which is unsubstituted or substituted with 1 or 2 substituents independently selected from hydroxy, halogen, $(C_1-C_6)$alkyl, halo$(C_1-C_6)$alkyl, $(C_1-C_6)$alkoxy, halo$(C_1-C_6)$alkoxy. $R_5$ represents hydrogen, halogen, $(C_1-C_6)$alkyl, $(C_3-C_8)$cycloalkyl, $(C_3-C_8)$cycloalkyl$(C_1-C_6)$alkyl, phenyl, benzyl, thiophenyl, thiazolyl, pyridyl, imidazolyl, pyrazolyl, or pyrimidinyl. Preferably $R_5$ represents hydrogen, halogen, or $(C_1-C_6)$alkyl.

$R_6$ and $R_7$ independently represent hydrogen, fluorine, or $C_1-C_6$alkyl.

W represents phenyl, thienyl, thiazolyl, pyridyl, imidazolyl, pyrazolyl, isoxazolyl, or pyrimidinyl, each of which is unsubstituted or substituted with from 1 to 4 groups independently selected from $R_{30}$. Preferably W represents phenyl, 2-thiazoyl, or 2-pyridyl, each of which is unsubstituted or substituted with from 1 to 4 groups independently selected from $R_{30}$. $R_{30}$ carries the definition set forth in Formula III.

The invention also includes compounds of Formula V–Formula XXIV wherein $R_1$ and $R_4$ are independently selected from hydrogen, halogen, methyl, ethyl, methoxy, and ethoxy.

The invention includes compounds of Formula I and Formula II in which the group represented by

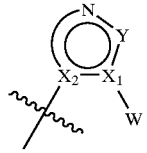

represents an imidazolyl or pyrrolyl group, each of which may be unsubstituted or substituted at each carbon atom by R, and unsubstituted or substituted at each nitrogen atom available for substitution by R' where R, R' and W, carry the definitions set forth above.

Additionally the invention includes compounds and pharmaceutically acceptable salts of Formula V–Formula XXIV wherein $R_1$ and $R_4$ are independently chosen from hydrogen, halogen, $C_1-C_2$haloalkyl, $C_1-C_2$haloalkoxy, $C_1-C_6$alkyl, hydroxy$C_1-C_6$alkyl, and $C_1-C_6$alkoxy. Preferably $R_1$ and $R_4$ are independently chosen from hydrogen, ethyl, methyl, methoxy, and 1-hydroxy-ethyl. In certain preferred embodiments, the invention includes compounds of Formula V–Formula XXIV in which $R_1$ and $R_4$ are both hydrogen.

Preferred values of $R_2$ for compounds and pharmaceutically acceptable salts of Formula V–Formula XXIV include hydrogen, cyano, halogen, $C_1-C_2$haloalkyl, $C_1-C_2$haloalkoxy, $C_1-C_6$alkyl, hydroxy$C_1-C_6$alkyl, $C_1-C_6$alkoxy, and heterocycloalkyl. Particularly preferred values of $R_2$ for compounds Formula V–Formula XXIV include hydrogen, cyano, bromo, chloro, methyl, ethyl, methoxy, trifluoromethyl, and pyrrolidinyl.

In certain embodiments $R_3$ for compounds and pharmaceutically acceptable salts of Formula V–Formula XXIV is chosen from hydrogen, cyano, halogen, $C_1-C_2$haloalkyl, $C_1-C_2$haloalkoxy, $C_1-C_6$alkyl, $C_2-C_6$alkenyl, $C_2-C_6$alkenyl substituted with hydroxy, mono- and di-$C_1-C_6$alkylamino, $C_1-C_3$alkanoyl, hydroxy$C_1-C_6$alkyl, $C_1-C_6$alkoxy, $C_1-C_6$alkoxy substituted with hydroxy, heteroaryl, heterocycloalkyl, and phenyl which is optionally substituted with one or more of halogen, $C_1-C_2$alkyl, $C_1-C_2$alkoxy, and $C_1-C_2$haloalkyl. The invention particularly includes compounds and salts of Formula V–Formula XXIV those wherein $R_3$ is chosen from hydrogen, chloro, fluoro, bromo, methyl, methylamino, dimethylamino, 1,3,4-oxadiazolyl, thienyl, 1,3-thiazolyl, pyridyl, acetyl, trifluoromethyl, 3-hydroxy-3-methylbutoxy, 2-hydroxy-2-methyl-3-butenyl, phenyl, methylphenyl, methoxyphenyl, and trifluormethylphenyl. In certain preferred embodiments $R_3$ in compounds and salts of Formula V–Formula XXIV is chosen from hydrogen, $C_1-C_6$ alkyl, acetyl, cyano, and trifluoromethyl.

The invention particularly includes compounds and salts of Formula V–Formula XXIV in which $R_5$ is ethyl or propyl.

Preferred values of W for compounds and salts of Formula V–Formula XXIV include phenyl, thiazolyl, pyridyl, and pyrimidinyl, each of which is unsubstituted or substituted with 1 or 2 groups independently chosen from halogen, $C_1-C_2$alkyl, $C_1-C_2$alkoxy, and $C_1-C_2$ haloalkyl. The invention particularly includes compounds and salts of Formula V–Formula XXIV in which W is selected from thiazolyl, pyrimidinyl, phenyl, 2-pyridyl, 3-fluorophenyl and 3-fluoro-2-pyridyl.

As an additional embodiment, invention includes compounds and pharmaceutically acceptable salts of Formula II (shown above) in which $R_1$ and $R_2$ are independently selected from hydrogen, halogen, nitro, cyano, halo($C_1$–$C_6$) alkyl, halo($C_1$–$C_6$)alkoxy, $C_1$–$C_6$alkyl, $C_1$–$C_6$alkoxy, $C_3$–$C_7$cycloalkyl, $C_2$–$C_6$alkenyl, $C_2$–$C_6$alkynyl, ($C_3$–$C_7$) cycloalkyl) $C_1$–$C_4$alkyl, mono and di($C_1$–$C_6$)alkylamino, and amino($C_1$–$C_6$)alkyl.

$R_5$ in this embodiment of the invention represents: (i) hydrogen, halogen, cyano, or haloalkyl; (ii) ($C_1$–$C_6$)alkyl, ($C_3$–$C_8$)cycloalkyl, ($C_3$–$C_8$cycloalkyl)($C_1$–$C_4$)alkyl, each of which comprises from 0 to 3 double bonds and/or from 0 to 3 triple bonds, each of which is unsubstituted or substituted with 1, 2, or 3 substituents independently selected from $R_{30}$; or (iii) aryl, aryl($C_1$–$C_4$)alkyl, 3- to 8-membered heteroaryl, or 3- to 8-membered heteroaryl($C_1$–$C_4$)alkyl, each of which is unsubstituted or substituted with 1, 2, or 3 substituents independently selected from the group consisting of ($C_1$–$C_6$) alkyl, halo($C_1$–$C_6$)alkyl, amino, —NH($R_{10}$), —N($R_{10}$) ($R_{11}$), carboxamido, ($R_{10}$)NHcarbonyl, ($R_{10}$)($R_{11}$) Ncarbonyl, halogen, hydroxy, nitro, cyano, amino, ($C_1$–$C_6$) alkoxy, ($C_1$–$C_6$)alkoxy substituted with amino or mono- or di($C_1$–$C_6$)alkylamino, halo($C_1$–$C_6$)alkoxy, ($C_3$–$C_8$) cycloalkyl, ($C_3$–$C_8$)cycloalkyl($C_1$–$C_4$)alkyl, ($C_3$–$C_8$) cycloalkyl ($C_1$–$C_4$)alkoxy, heterocyclo($C_1$–$C_4$)alkyl, ($C_2$–$C_6$)alkenyl, ($C_2$–$C_6$)alkynyl, amino($C_1$–$C_6$) alkyl, and mono- and di($C_1$–$C_6$)alkylamino($C_1$–$C_6$)alkyl.

Q represents C($R_6$)($R_7$), N($C_1$–$C_6$alkyl) or oxygen, wherein $R_6$ and $R_7$ independently represent hydrogen, fluorine, or ($C_1$–$C_6$)alkyl; with the proviso that Q is not oxygen when $X_2$ is nitrogen.

$R_{10}$ and $R_{11}$ are independently selected from the group consisting of ($C_1$–$C_6$)alkyl, ($C_2$–$C_6$)alkenyl, ($C_2$–$C_6$) alkynyl, ($C_1$–$C_6$)alkoxy, ($C_3$–$C_8$)cycloalkyl, ($C_3$–$C_8$) cycloalkyl($C_1$–$C_4$)alkyl, aryl, aryl($C_1$–$C_4$)alkyl, ($C_1$–$C_6$) alkanoyl, and mono and di($C_1$–$C_6$)alkylamino($C_1$–$C_6$)alkyl.

$R_{30}$ is independently selected at each occurrence from halogen, hydroxy, nitro, cyano, amino, ($C_1$–$C_6$)alkyl, ($C_1$–$C_6$)alkoxy, ($C_1$–$C_6$)alkoxy substituted with amino or mono- or di($C_1$–$C_6$)alkylamino, ($C_3$–$C_8$)cycloalkyl, ($C_3$–$C_8$)cycloalkyl($C_1$–$C_4$)alkyl, ($C_3$–$C_8$)cycloalkyl($C_1$–$C_4$) alkoxy, 3- to 8-membered heterocyclo($C_1$–$C_6$)alkyl, ($C_2$–$C_6$)alkenyl, ($C_2$–$C_6$)alkynyl, halo($C_1$–$C_6$)alkyl, halo ($C_1$–$C_6$)alkoxy, mono- and di($C_1$–$C_6$)alkylamino, amino ($C_1$–$C_6$)alkyl, and mono- and di($C_1$–$C_6$)alkylamino($C_1$–$C_6$) alkyl.

R is independently chosen at each occurrence from halogen, amino, $C_1$–$C_6$alkyl, ($C_2$–$C_6$)alkenyl, ($C_2$–$C_6$) alkynyl, $C_1$–$C_6$alkoxy, ($C_3$–$C_8$)cycloalkyl, ($C_3$–$C_8$cycloalkyl)($C_1$–$C_4$)alkyl, halo($C_1$–$C_6$)alkyl, haloalkoxy, carboxamido, and 3- to 7-membered carbocyclic and heterocyclic rings, each of which is unsubstituted or substituted with from 1 to 4 substituents independently selected from halogen, oxo, hydroxy, $C_1$–$C_4$alkyl, and $C_1$–$C_4$alkoxy.

R' is independently chosen at each occurrence from $C_1$–$C_6$alkyl, $C_3$–$C_8$cycloalkyl, $C_3$–$C_8$cycloalkyl ($C_1$–$C_4$alkyl), and 3- to 7-membered carbocyclic and heterocyclic rings, each of which is unsubstituted or substituted with from 1 to 4 substituents independently selected from halogen, oxo, hydroxy, $C_1$–$C_4$alkyl, and $C_1$–$C_4$alkoxy.

W represents 3- to 8-membered aryl or heteroaryl, each of which is unsubstituted or substituted with from 1 to 4 groups independently selected from $R_{30}$, —C(=O)O$R_E$, —C(=O) N$R_E$, —C(O)$R_E$, —O$R_E$ and —S(O)$_m$$R_E$, wherein m is 0, 1, or 2. $R_E$ carries the definition set fort compounds of Formula II. Such compounds will be referred to as compounds of Formula XV.

The invention includes compounds and pharmaceutically acceptable salts of Formula XVI

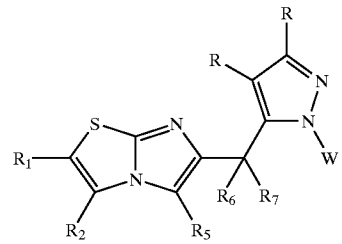

Formula XVI $R_5$ in this embodiment of the invention represents hydrogen, halogen, or ($C_1$–$C_6$)alkyl, and $R_6$ and $R_7$ independently represent hydrogen or ($C_1$–$C_6$) alkyl. The remaining variables shown in Formula XVI, e.g., $R_1$ and $R_2$ carry the definitions set forth in Formula XVI.

Certain preferred compounds and salts of Formula XVI are those wherein W represents phenyl, 2-thiazoyl, or 2-pyridyl, each of which is unsubstituted or substituted with from 1 to 4 groups independently selected from $R_{30}$.

Other preferred compounds and salts of Formula XVI are those wherein W represents phenyl, 2-thiazoyl, or 2-pyridyl, each of which is unsubstituted or substituted with from 1 to 4 groups independently selected from $R_{30}$ and $R_1$ and $R_2$ are independently selected from hydrogen, halogen, nitro, cyano, ($C_1$–$C_6$)alkyl, ($C_1$–$C_6$)alkoxy, ($C_3$–$C_8$)cycloalkyl, ($C_3$–$C_8$)cycloalkyl($C_1$–$C_6$)alkyl, ($C_2$–$C_6$)alkenyl, ($C_2$–$C_6$) alkynyl, heterocycloalkyl, halo($C_1$–$C_6$)alkyl, halo($C_1$–$C_6$) alkoxy, mono and di($C_1$–$C_6$)alkylamino, amino($C_1$–$C_6$) alkyl, and mono- and di($C_1$–$C_6$)alkylamino($C_1$–$C_6$)alkyl.

This invention relates to heteroaryl substituted fused bicyclic heteroaryl compounds, such as heteroaryl substituted imidazopyridines, imidazopyrazines, imidazopyridizines, imidazopyrimidines, and imidazothiazoles, preferred examples of which bind with high affinity to the benzodiazepine site of $GABA_A$ receptors, including human $GABA_A$ receptors. Affinity of a compound of Formula I or Formula II for $GABA_A$ receptors may be determined using a standard $GABA_A$ receptor radioligand binding assay such as the assay given in Example 17. Preferred compounds of Formula I and/or Formula II exhibit a $K_i$ of less than 1 micromolar in a $GABA_A$ receptor radioligand binding assay such as the assay given in Example 17, or more preferably less than 100 nM or most preferably less than 10 nM in such and assay. Preferred benzimidazole and pyridylimidazole derivatives that bind with high selectivity to the benzodiazepine site of $GABA_A$ receptors, including human $GABA_A$ receptors, are also included in this invention. Without wishing to be bound to any particular theory, it is believed that the interaction of the compounds of Formula I and Formula II with the benzodiazepine site results in the pharmaceutical utility of these compounds.

The invention further comprises methods of treating patients in need of such treatment with an amount of a compound of the invention sufficient to alter the symptoms of a CNS disorder. Compounds of Formula I and/or Formula II that exhibit agonist or inverse agonist activity at particular receptor subtypes are particularly useful for treating certain CNS disorders. For example, compounds of Formula I and/or Formula II that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\beta_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as inverse agonists at the $\alpha_5\beta_3\gamma_2$ are particularly useful in treating cognitive disorders through the enhancement of memory, and particularly short-term memory, in memory-impaired patients. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases and/or disorders that can also be treated using compounds and compositions according to the invention include:

Depression, e.g. depression, atypical depression, bipolar disorder, depressed phase of bipolar disorder.

Anxiety, e.g. general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, memory impairment, short-term memory impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

Attention Deficit Disorder, e.g. attention deficit disorder (ADD), and attention deficit and hyperactivity disorder (ADHD).

Speech disorders, e.g. stuttering, including motor tic, clonic stuttering, dysfluency, speech blockage, dysarthria, Tourete's syndrome or logospasm.

Psychosis e.g. schizophrenia, hallucinatory disorders

The invention also provides pharmaceutical compositions comprising one or more compounds of the invention together with a pharmaceutically acceptable carrier or excipient, for treating disorders responsive to $GABA_A$ receptor modulation, e.g., treatment of anxiety, depression, sleep disorders or cognitive impairment by $GABA_A$ receptor modulation. Pharmaceutical compositions include packaged pharmaceutical compositions comprising a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5-HT_{1A}$) agonists and antagonists; for anxiety and depression, neurokinin receptor antagonists or corticotropin releasing factor receptor $(CRF_1)$ antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the $GABA_A$ receptor ligand 3-(5-methylisoxazol-3-yl)-6-(1-methyl-1,2,3-triazol-4-yl)methyloxy-1,2,4-triazolo[3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The present invention also pertains to methods of inhibiting the binding of benzodiazepine compounds, such as Ro15-1788 (flumazenil), or GABA to the $GABA_A$ receptors which methods involve contacting a solution containing compound of the invention with cells expressing $GABA_A$ receptors, wherein the compound is present at a concentration sufficient to inhibit benzodiazepine binding or GABA binding to $GABA_A$ receptors in vitro. This method includes inhibiting the binding of benzodiazepine compounds to $GABA_A$ receptors in vivo, e.g., in a patient given an amount of a compound of Formula I or Formula II that would be sufficient to inhibit the binding of benzodiazepine compounds or GABA to $GABA_A$ receptors in vitro. In one embodiment, such methods are useful in treating benzodiazepine drug overdose. The amount of a compound that would be sufficient to inhibit the binding of a benzodiazepine compound to the $GABA_A$ receptor may be readily determined via a $GABA_A$ receptor binding assay, such as the assay described in Example 17. The $GABA_A$ receptors used to determine in vitro binding may be obtained from a variety of sources, for example from preparations of rat cortex or from cells expressing cloned human $GABA_A$ receptors.

The present invention also pertains to methods for altering the signal-transducing activity, particularly the chloride ion conductance of $GABA_A$ receptors, said method comprising exposing cells expressing such receptors to an effective amount of a compound of the invention. This method includes altering the signal-transducing activity of $GABA_A$ receptors in vivo, e.g., in a patient given an amount of a compound of Formula I or Formula II that would be sufficient to alter the signal-transducing activity of $GABA_A$ receptors in vitro. The amount of a compound that would be sufficient to alter the signal-transducing activity of $GABA_A$ receptors may be determined via a $GABA_A$ receptor signal transduction assay, such as the assay described in Example 18. The cells expressing the GABA receptors in vivo may be, but are not limited to, neuronal cells or brain cells. Such cells may be contacted with compounds of the invention through contact with a body fluid containing the compound, for example through contact with cerebrospinal fluid. Alteration of the signal-transducing activity of $GABA_A$ receptors in vitro may be determined from a detectable change in the electrophysiology of cells expressing $GABA_A$ receptors, when such cells are contacted with a compound of the invention in the presence of GABA.

Intracellular recording or patch-clamp recording may be used to quantitate changes in electrophysiology of cells. A reproducible change in behavior of an animal given a compound of the invention may also be used to indicate that changes in the electrophysiology of the animal's cells expressing $GABA_A$ receptors has occurred.

The $GABA_A$ receptor ligands provided by this invention and labeled derivatives thereof are also useful as standards and reagents in determining the ability of a potential pharmaceutical to bind to the $GABA_A$ receptor. Radiolabeled derivatives the $GABA_A$ receptor ligands provided by this invention are also useful as radiotracers for positron emission tomography (PET) imaging or for single photon emission computerized tomography (SPECT).

More particularly compounds of the invention may be used for demonstrating the presence of $GABA_A$ receptors in cell or tissue samples. This may be done by preparing a plurality of matched cell or tissue samples, at least one of which is prepared as an experimental sample and at least one of which is prepared as a control sample. The experimental sample is prepared by contacting (under conditions that permit binding of RO15-1788 to $GABA_A$ receptors within cell and tissue samples) at least one of the matched cell or tissue samples that has not previously been contacted with any compound or salt of the invention with an experimental solution comprising the detectably-labeled preparation of the selected compound or salt at the first measured molar concentration. The control sample is prepared by in the same manner as the experimental sample and also contains an unlabelled preparation of the same compound or salt of the invention at a greater molar concentration.

The experimental and control samples are then washed to remove unbound detectably-labeled compound. The amount of remaining bound detectably-labeled compound is then measured and the amount of detectably-labeled compound in the experimental and control samples is compared. A comparison that indicates the detection of a greater amount of detectable label in the at least one washed experimental sample than is detected in any of control samples demonstrates the presence of $GABA_A$ receptors in that experimental sample.

The detectably-labeled compound used in this procedure may be labeled with a radioactive label or a directly or indirectly luminescent label. When tissue sections are used in this procedure and the detectably-labeled compound is radiolabeled, the bound, labeled compound may be detected autoradiographically to generate an autoradiogram. The amount of detectable label in an experimental or control sample may be measured by viewing the autoradiograms and comparing the exposure density of the autoradiograms.

Pharmaceutical Compositions

The compounds of general Formulas I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and/or a compound of general Formula II and a pharmaceutically acceptable carrier. One or more compounds of general Formula I or Formula II may be present in association with one or more non-toxic pharmaceutically acceptable carriers and/or diluents and/or adjuvants and if desired other active ingredients. The pharmaceutical compositions containing compounds of general Formula I and/or Formula II may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or. more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or peanut oil, or a mineral oil, for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formulas I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formulas I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to high solubility (preferably 500 ng/ml or more) in aqueous solutions, oral bioavailability, low toxicity, low serum protein binding, lack of clinically relevant EKG effects, and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

EXAMPLES

Preparation of Compounds

A general illustration of the preparation of compounds of Formula I and Formula XXVI in the present invention is given in Schemes 1–9. The following abbreviations are used in the reaction schemes and examples which follow:

AIBN—2,2'-Azabisisobutronitrile

DIBAL-H—Diisobutylaluminum hydride

LDA—Lithium diisopropylamide

NBS—N-bromosuccinamide

NCS—N-chlorosuccinamide

THF—tetrahydrofuran

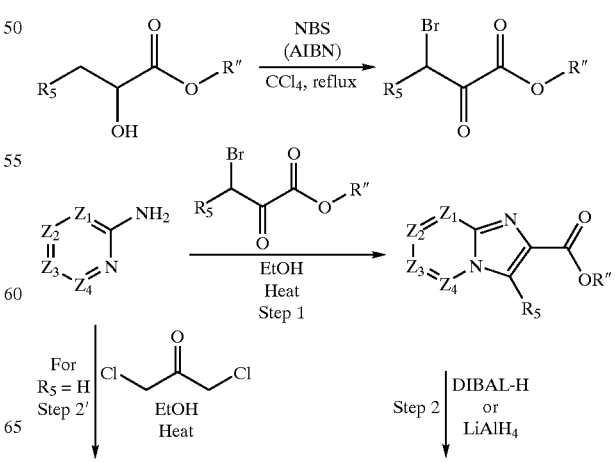

SCHEME 1

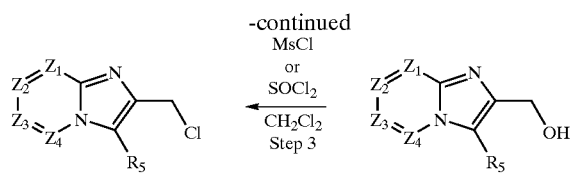

Scheme 1 shows a route for synthesizing chloromethyl or mesylmethyl fused imidazo compounds used in the preparation of compounds of Formula I. Step 1 involves reaction of an alpha-bromoketoester with a 2-aminopyridine, 2-aminopyrmidine, 2-aminopyrazine, 4-aminopyrimidine, 3-aminopyridazine or other appropriate aminoheteroaromatic to form an imidazo acid ester. The requisite alpha-bromoketoester is prepared by reaction of the corresponding alpha-hydroxyester with N-bromosuccinimide (wherein R" is alkyl) in carbon tetrachloride in the presence of catalytic AIBN. Step 1 results in an isomeric mixture when $Z_1$ is nitrogen. In step 2, the imdiazo acid ester is reduced to the corresponding alcohol using diisobutylaluminum hydride, lithium aluminum hydride or other appropriate reducing agent. Low yields are often obtained from Step 2 of Scheme 1 when $Z_2$ or $Z_3$ is nitrogen. In cases where reduction of the fused heteroaromatic ring occurs, the transformation from imdazo acid ester to alcohol may be accomplished by hydrolyzing the ester, converting the acid to the acid chloride and treating the acid chloride with sodium borohydride or other appropriate reducing agent. In step 3, the alcohol is converted to the corresponding mesylate or chloride by reaction with thionyl chloride or methanesulfonyl chloride. Compounds of Formula I with $R_5$=H may be obtained by reaction of 1,1' -dichloroacetone with the appropriate aminoheteroaromatic compound as shown in Step 2'. Those skilled in the art will recognize that the starting materials, reagents and reactions in Scheme 1 can be modified to readily obtain a variety of intermediates used in preparing compounds of Formula I.

lithium followed by tri-n-butyltin chloride to obtain the corresponding 2-(tri-n-butyltin)-imidazole. The 2-(tri-n-butyltin)-imidazole intermediate must be handled with care to avoid decomposition. Subsequent palladium (0) catalyzed coupling with an appropriate aryl or heteroaryl halide (denoted as ArX in scheme 2) provides the corresponding 2-aryl or 2-heteroaryl methoxymethyl-protected imidazole. Removal of the methoxymethyl protecting group with acid provides the desired aryl or heteroaryl imidazole for use in preparing compounds of Formula I and Formula II.

SCHEME 3

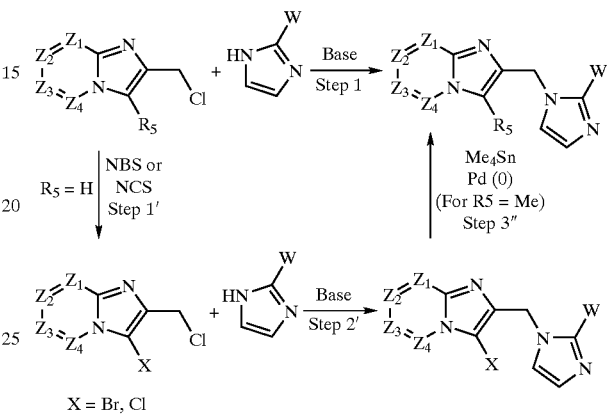

X = Br, Cl

Scheme 3 provides a route for preparing compounds of Formula I by reacting the appropriate chloromethyl fused imidazo compounds and aryl or heteroaryl imidazoles. In step 1, a chloromethyl fused imidazo compound is reacted with an aryl or heteroaryl imidazole in the presence of an appropriate base to form compounds of Formula I. Appropriate bases include but are not limited to sodium hydride, potassium carbonate and cesium carbonate. When $R_5$=H in Scheme 3, step 1' may be employed to produce a chlorom-

SCHEME 2

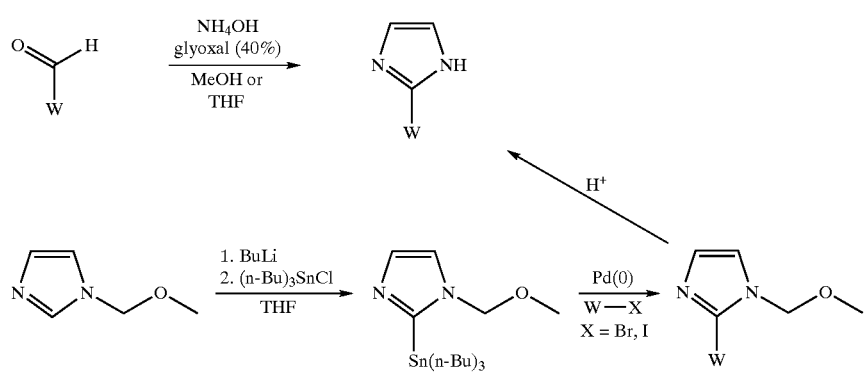

Scheme 2 illustrates two routes to aryl and heteroaryl imidazoles which are intermediates in the synthesis of selected compounds of Formula I and Formula II.

In the first route, an aryl or heteroaryl aldehyde is treated with glyoxal and ammonium hydroxide to form the corresponding aryl or heteroaryl imidazole. The second route, involving palladium (0) catalyzed cross-coupling, is used when direct conversion of the aryl or heteroaryl aldehyde to aryl or heteroaryl imidazole provides low yields, e.g., in the preparation of 2-(1H-imidazolyl-2-yl)-thiazole. In this route, methoxymethyl-protected imidazole is treated with butyl ethyl fused imidazo compound with $R_5$=Br or Cl. Reaction of the resulting haloimidazo compound with an aryl or heteroaryl imidazole in step 2' provides compounds of Formula I with $R_5$=Br or Cl. In step 3', a compound of Formula I with $R_5$=Br is optionally converted to a compound of Formula I with $R_5$=methyl via the action of tetramethyltin in the presence of palladium (0). Steps 1', 2' and 3' provide a convenient method for preparing compounds of Formula I wherein $Z_2$ or $Z_3$ is nitrogen and $R_5$ is methyl.

SCHEME 4

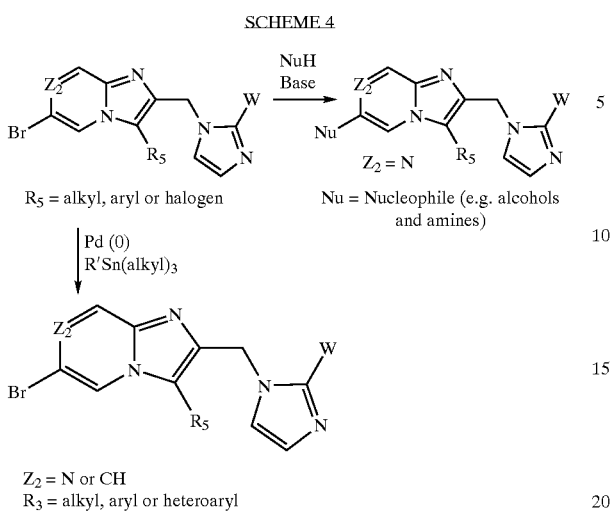

$R_5$ = alkyl, aryl or halogen
Nu = Nucleophile (e.g. alcohols and amines)
$Z_2$ = N or CH
$R_3$ = alkyl, aryl or heteroaryl Scheme 4 provides a method for obtaining compounds of Formula I with substitution at $Z_3$. Analogous chemistry can be used to introduce substitution at $Z_1$, $Z_2$, or $Z_4$. In this scheme, a compound of Formula I with $Z_3$=halogen (preferably bromine) is coupled with an aryl or alkyl tin reagent in the presence of palladium (0) catalyst to obtain a compound of Formula I with $Z_3$=aryl or alkyl. Those skilled in the art will recognize that suitable aryl or alkyl boronic acids may be used in place of aryl or alkyl tin reagents in some cases. When $Z_2$ is nitrogen and $Z_3$ is Br or Cl, a nitrogen or oxygen nucleophile (NuH) can be used to displace $Z_3$ to obtain compounds of Formula I with $Z_2$=nitrogen or oxygen. For example, compounds of Formula I with $Z_2$=N and $Z_3$=alkylamino are readily produced by this route.

SCHEME 5

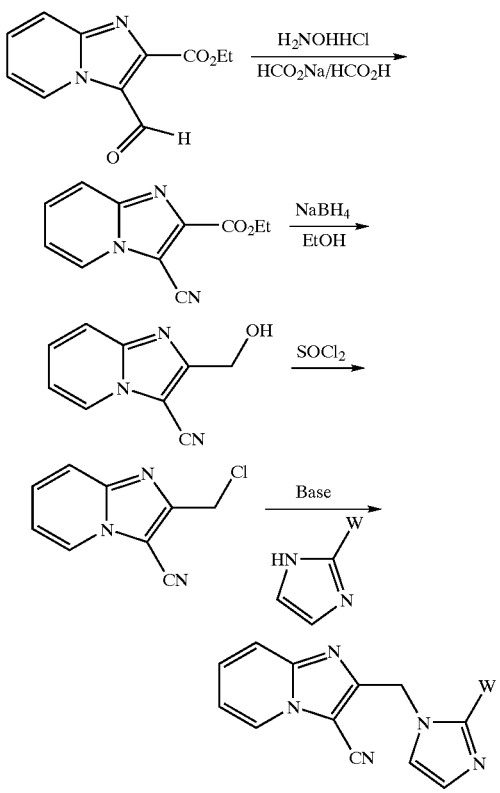

Scheme 5 is used to prepare compounds of Formula I wherein $R_5$ is cyano. In this scheme, imidazo[1,2-a]pyridine-2-carboxylic acid ethyl ester is reacted with formaldehyde in acetic acid to produce the corresponding hydroxymethyl derivative. Oxidation of the primary alcohol provides the aldehyde which is subsequently converted to the oxime and dehydrated to the nitrile. Selective reduction of the ethyl ester group in 3-cyano-imidazo[1,2-a]pyridine-2-carboxylic acid ethyl ester provides the corresponding alcohol which is converted to the chloromethyl derivative and reacted with an aryl or heteroaryl imidazole as described in Scheme 3. Those skilled in the art will recognize that this synthetic route can be readily modified to incorporate alternate starting materials and reagents to synthesize many other compounds of Formula I, where $R_5$=CN and $Z_1$, $Z_2$, $Z_3$ and $Z_4$ are $CR_1$, $CR_2$, $CR_2$, and $CR_4$.

SCHEME 6

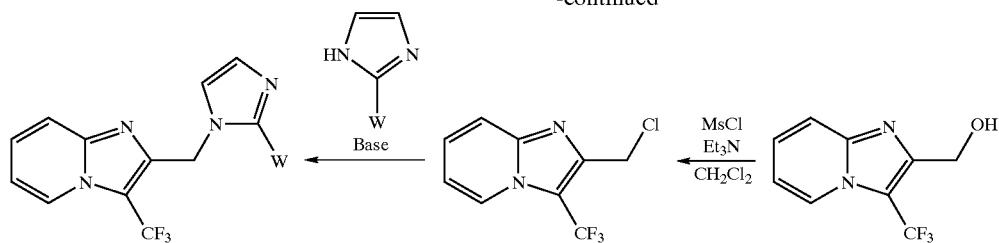

Scheme 6 is used to prepare compounds of Formula I wherein $R_5$ is trifluoromethyl. In this route, known 3-bromo-imidazo[1,2-a]pyridine-2-carboxylic acid ethyl ester is produced by bromination of imidazo[1,2-a]pyridine-2-carboxylic acid ethyl ester with N-bromosuccinamide. The resulting 3-bromo-imidazo[1,2-a]pyridine-2-carboxylic acid ethyl ester is reacted with trifluoromethyltriethylsilane in the presence of potassium fluoride and copper (I) chloride to obtain the corresponding 3-trifluoromethyl derivative. This material is converted to compounds of Formula I as described in Schemes 1 and 3. Those skilled in the art will recognize that this synthetic route can be readily modified to incorporate alternate starting materials and reagents to synthesize many other compounds of Formula I, where $R_5=CF_3$ and $Z_1$, $Z_2$, $Z_3$ and $Z_4$ are $CR_1$, $CR_2$, $CR_2$, and $CR_4$.

SCHEME 7

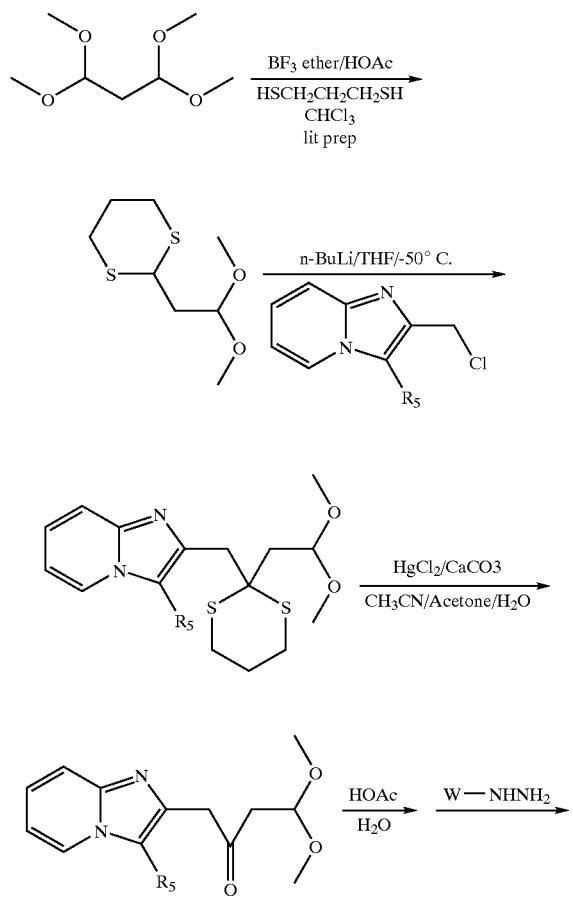

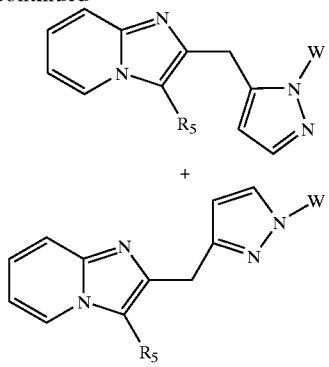

Scheme 7 shows a method of synthesizing aryl and heteroaryl pyrazole compounds of Formula I. In this route, 2-(2,2-dimethoxyethyl)-[1,3]dithiane (J. Het. Chem. 1987, 1221) is reacted with n-butyllithium followed by a chloromethyl fused imidazo compound to produce the corresponding alkylation product. Removal of the [1,3]dithiane yields the corresponding ketone acetal derivative. This material is deprotected to the ketone aldehyde and reacted in situ to obtain the desired pyrazole compounds of Formula I. Undesired isomeric pyrazole is separated by chromatography on silica gel. Those skilled in the art will recognize that this synthetic route can be readily modified to incorporate alternate starting materials and reagents to synthesize many other pyrazole compounds of Formula I, including compounds wherein $Z_1$, $Z_2$, $Z_3$ and $Z_4$ are N or $CR_1$, $CR_2$, $CR_2$, and $CR_4$.

SCHEME 8

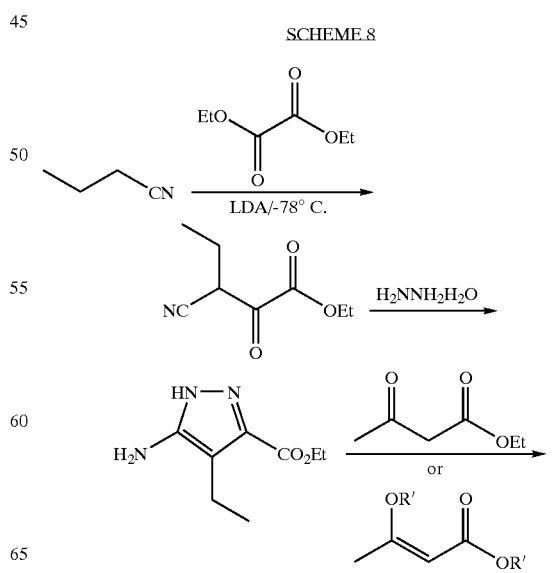

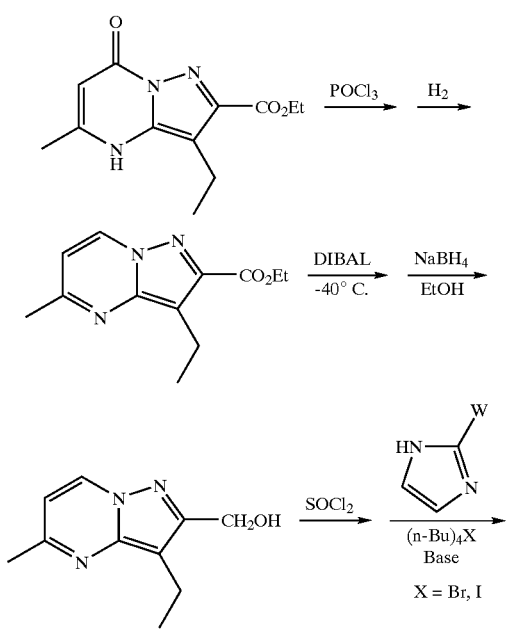

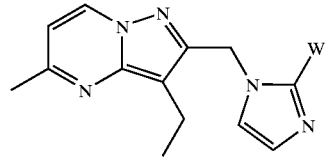

Scheme 8 illustrates a route for preparing compounds of Formula I wherein $Z_4$ and $Z_6$ are nitrogen. In this route an alkyl nitrile is condensed with oxalic acid diethyl ester to obtain the corresponding 3-alkyl-3-cyano-2-oxo-propionic acid ethyl ester. Treatment of the 3-alkyl-3-cyano-2-oxo-propionic acid ethyl ester with hydrazine monohydrate provides the 5-amino-4-alkyl-1H-pyrazole-3-carboxylic acid ethyl ester which is subsequently reacted with 3-oxo-butyric acid ethyl ester or equivalent reagent to obtain the 3-alkyl-5-methyl-7-oxo-4,7-dihydro-pyrazolo[1,5-a]-pyrimidine-2-carboxylic acid ethyl ester. Reduction of the ethyl ester to the corresponding alcohol is accomplished using diisobutylaluminum hydride at low temperature. Further synthetic transformations as previously described in Schemes 1 and 3 provide compounds of Formula I with $Z_4$ and $Z_6$=nitrogen. Those skilled in the art will recognize that this synthetic route can be readily modified to incorporate alternate starting materials and reagents to synthesize many other compounds of Formula I wherein $Z_4$ and $Z_6$ are nitrogen.

SCHEME 9

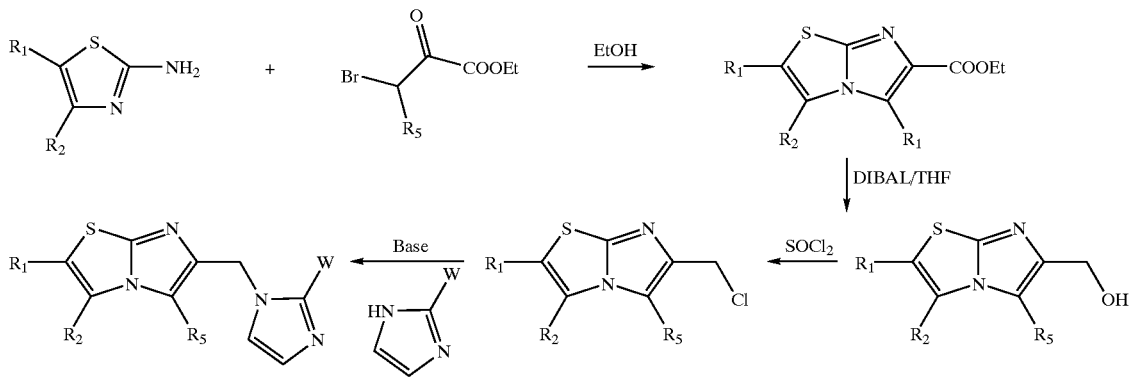

Scheme 9 provides a method for preparing compounds of Formula II from 2-aminothiazoles. The various synthetic transformations involved have previously been described in Schemes 1, 3 and 8.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. Unless otherwise stated starting material and reagents employed in this synthesis are of standard commercial grade. In some cases, protection of certain reactive functionalities may be necessary to achieve some of the above transformations. In general, such need for protecting groups, as well as the conditions necessary to attach and remove such groups, will be apparent to those skilled in the art of organic synthesis.

Example 1
Synthesis of 3-Fluoro-(1H-imidazol-2-yl)benzene

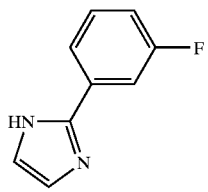

Saturated ammonium hydroxide solution (30 mL) is slowly added to a solution of 3-fluorobenzaldehyde (12.4 g, 100 mmol) and glyoxal (17.5 mL of 40% wt in water, 120 mmol) in methanol (100 mL) at ambient temperature. After stirring for 24 hours, most of the solvent is removed at reduced pressure. Benzene is added and evaporated to remove residual water. The resulting dark oil is purified by chromatography on silica gel (2% MeOH/CH$_2$Cl$_2$) to obtain a tan solid. Trituration with ether/hexane provides 3-fluoro-(1H-imidazol-2-yl)benzene as a white solid. LRMS m/z (M+1) 163.2.

Example 2
Synthesis of 3-Chloro-4-fluoro-(1H-imidazol-2-yl)benzene

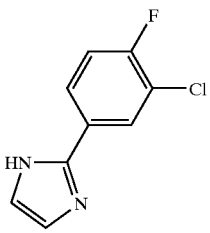

A mixture of 3-chloro-4-fluoro-benzaldehyde (0.032 mol), glyoxal (40% in water, 0.038 mol) and ammonium hydroxide (28% in water, 0.16 mol) in MeOH (60 mL) is stirred at room temperature overnight. Solvent is removed in vacuo and the residue is partitioned between water and CH$_2$Cl$_2$. The organic layer is washed with brine, dried (Na$_2$SO$_4$), and concentrated. The residue is purified by column chromatography on silica gel eluting with CH$_2$Cl$_2$/MeOH (95/5) to afford 3-chloro-4-fluoro-(1H-imidazol-2-yl)benzene as a yellow solid. $^1$H NMR (CDCl$_3$) δ 7.88 (dd, 1H), 7.70 (m, 1H), 7.19 (t, 1H), 7.17 (s, 2H). LRMS m/z (M+1) 197.0.

Example 3
Synthesis of 2,3,4-Trifluoro-(1H-imidazol-2-yl)benzene

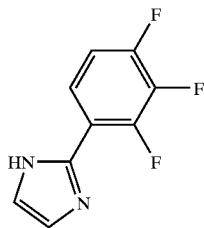

Saturated ammonium hydroxide solution (26 mL) is slowly added to a solution of 2,3,4-trifluorobenzaldehyde (5.0 g, 31.2 mmol) and glyoxal (10.75 mL of 40% wt in water, 93.7 mmol) in methanol (100 mL) at ambient temperature. After stirring for 24 hours, most of the solvent is removed at reduced pressure. Benzene is added and evaporated to remove residual water. The resulting dark oil is purified by chromatography on silica gel (5% MeOH/CH$_2$Cl$_2$) to obtain a tan solid. Trituration with ether/hexane provides 2,3,4-trifluoro-(1H-imidazol-2-yl)benzene as a white solid. LRMS m/z (M+1) 199.10.

Example 4
Synthesis of 1-Ethoxymethyl-2-tributylstannanyl-1H-imidazole

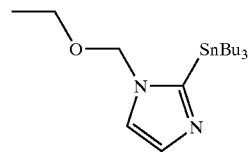

1.6 M n-BuLi (12.0 mL, 19.2 mmol) is slowly added to a solution of 1-ethoxymethyl-1H-imidazole [available via the procedure outlined in Tang, C. C.; Davalian, D.; Huang, P.; Breslow, R. J. Am. Chem. Soc. 1978, 100, 3918] (2.20 g, 17.4 mmol) in THF (30 mL) at −78° C. under N$_2$. The reaction mixture is stirred at −78° C. for 20 minutes whereupon tributyl tin chloride (5.7 mL, 20.9 mmol) is added slowly. The reaction mixture is stirred at −78° C. for 10 minutes and then warmed to room temperature. After stirring at room temperature for 1.5 hours, the reaction mixture is concentrated in vacuo. The residue is triturated with hexanes and filtered, and the filtrate is concentrated in vacuo. The residue is again triturated with hexanes and filtered, and the filtrate concentrated in vacuo. The $^1$H NMR of the resulting oil indicates a 2:1 mixture of 1-ethoxymethyl-2-tributylstannanyl-1H-imidazole: 1-ethoxymethyl-1H-imidazole. This material is used in the next reaction (Example 5) without further purification. Selected $^1$H NMR resonances (400 MHz, CDCl$_3$) δ 7.21 (s, 1H), 7.14 (s, 1H), 5.24 (s, 2H) ppm.

Example 5
Synthesis of 2-(1-Ethoxymethyl-1H-imidazol-2-yl)-thiazole

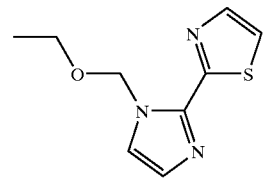

A solution of crude 1-ethoxymethyl-2-tributylstannanyl-1H-imidazole (previous example), 2-bromothiazole (1.05 mL, 11.6 mmol, 1.0 equivalents based on integration of $^1$H NMR of crude 1-ethoxymethyl-2-tributylstannanyl-1H-imidazole), and Pd(PPh$_3$)$_4$ (0.67 g, 0.58 mmol) in toluene (20 mL) is stirred at 80° C. for 18 hours. After cooling to room temperature, the reaction mixture is poured into saturated aqueous NaHCO$_3$ and extracted twice with CH$_2$Cl$_2$. The combined extracts are dried over Na$_2$SO$_4$ and concentrated in vacuo. The residue is purified by flash chromatography on silica gel, eluting with 2:1 hexanes:EtOAc (+0.5% Et$_3$N). Fractions containing product are concentrated and subjected again to flash chromatography on silica gel. Elution with 2:1 hexanes:EtOAc (+0.5% Et₃N) affords (26%) of 2-(1-ethoxymethyl-1H-imidazol-2-yl)-thiazole as a bright yellow oil. $^1$H NMR (400 MHz, CDCl₃) δ 7.82 (d, J=3.2 Hz, 1H), 7.33 (d, J=3.2 Hz, 1H), 7.20 (d, J=1.2 Hz, 1H), 7.15 (d, J=1.2 H, 1H), 6.03 (s, 2H), 3.56 (q, J=7.2 Hz, 2H), 1.17 (t, J=7.2 Hz, 3H) ppm.

Example 6

Synthesis of 2-(1H-Imidazol-2-yl)-thiazole

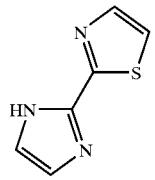

Concentrated HCl (10 ml) is added to a solution of 2-(1-ethoxymethyl-1H-imidazol-2-yl)-thiazole (940 mg, 4.49 mmol) in 24 mL of 1:1 EtOH—H₂O at room temperature. The solution is stirred at reflux for 3 hours. The reaction mixture is then cooled to 0° C. and made basic by the addition of about 12 mL of 10 N aqueous NaOH. The mixture is back titrated to approximately pH 4 using concentrated HCl. Solid NaHCO₃ is added to the point of saturation and approximately pH 8. The mixture is then extracted twice using a mixture of THF and EtOAc. The combined extracts are dried over Na₂SO₄ and concentrated to an oily solid, which is triturated with a small amount of CH₂Cl₂. The solid is collected by filtration. The filtrate is concentrated, and the oily solid triturated once more with CH₂Cl₂. The second resultant solid is collected by filtration and combined with the solid first obtained. The product, 2-(1H-imidazol-2-yl)-thiazole, is obtained as a slightly off-white solid. $^1$H NMR (400 MHz, DMSO-d₆) δ 13.04 (br, 1H), 7.87 (d, J=3.2 Hz, 1H), 7.70 (d, J=3.2 Hz, 1H), 7.14 (br, 2H) ppm.

Example 7

Synthesis of 3-{1-[(3-Propylimidazo[1,2-A]pyridin-2-yl)methyl]-1H-imidazol-2-yl}benzonitrile Step 1. Preparation of 3-bromo-2-oxo-hexanoic acid ethyl ester

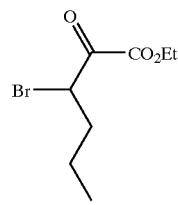

In a modification of the method described in JCS Perkin Trans. I 1972, 2584, a mixture of 2-hydroxy-hexanoic acid ethyl ester (5 g, 31 mmol), N-bromosuccinimide (12 g, 67 mmol) and catalytic AIBN in anhydrous CCl₄ (60 mL) is refluxed. After heating for about 20 minutes, the reaction initiates with evolution of a red-brown gas. After refluxing 4 hours, the resulting mixture is filtered and the filtrate evaporated at reduced pressure to obtain 3-bromo-2-oxo-hexanoic acid ethyl ester as a dark liquid.

Step 2. Preparation of 3-(1-propyl)-imidazolo[1,2-a]pyridine-2-carboxylate

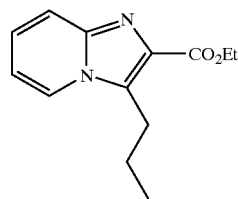

A solution of 3-bromo-2-oxo-hexanoic acid ethyl ester (2.4 g, 10 mmol) in THF (5 mL) is added to a solution of 2-aminopyridine (940 mg, 10 mmol) in anhydrous THF (5 mL). After 1 hour, ethanol (50 mL) is added and the solution is heated at reflux with magnetic stirring for 6 hours. The resulting dark mixture is evaporated at reduced pressure, diluted with EtOAc (100 mL), washed with saturated aqueous NaHCO₃ solution (30 mL), water (30 mL), brine (30 mL), dried over anhydrous Na₂SO₄ and evaporated at reduced pressure to obtain a yellow-orange solid. Recrystallization from diethyl ether provides pure 3-(1-propyl)-imidazolo[1,2-a]pyridine-2-carboxylate as a cream-colored solid. TLC (10% MeOH/CH₂Cl₂) Rf=0.60.

Step 3. Preparation of 2-hydroxymethyl-3-(1-propyl)-imidazolo[1,2-a]pyridine

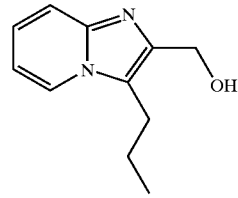

A solution of LiAlH₄ (1M in THF, 4.0 mL, 4.0 mmol) is added to a solution of 3-(1-propyl)-imidazolo[1,2-a]pyridine-2-carboxylate (1 g, 4.3 mmol) in anhydrous THF (50 mL) at 0° C. under nitrogen with magnetic stirring. The resulting pale yellow solution is stirred at 0° C. for 4 h and then quenched by addition of 75 mL of EtOAc and 2 mL saturated aqueous Na₂SO₄. The resulting mixture is stirred for 1 hour at ambient temperature, dried over anhydrous Na₂SO₄, filtered through celite and evaporated at reduced pressure to obtain 2-hydroxymethyl-3-(1-propyl)-imidazolo[1,2-a]pyridine as a colorless film. TLC (10% MeOH/CH₂Cl₂) Rf=0.15.

Step 4. Preparation of 2-chloromethyl-3-(1-propyl)-imidazolo[1,2-a]pyridine

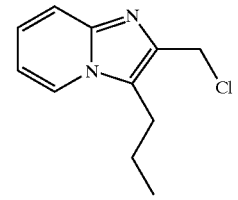

Thionyl chloride (125 mg, 1.06 mmol) is added to a solution of 2-hydroxymethyl-3-(1-propyl)-imidazolo[1,2-a]pyridine (100 mg, 0.53 mmol) in CH₂Cl₂ (3 mL) at 0° C. under nitrogen with magnetic stirring. After 1 hour, the reaction is diluted with EtOAc (20 mL), washed with saturated aqueous NaHCO₃ (10 mL), water (10 mL) and brine (10 mL). The solution is then dried over anhydrous sodium sulfate, filtered and evaporated at reduced pressure to obtain 2-chloromethyl-3-(1-propyl)-imidazolo[1,2-a]pyridine as a colorless oil. TLC (10% MeOH/CH₂Cl₂) Rf=0.60.

Step 5. Preparation of 3-{1-[(3-propylimidazo[1,2-a]pyridin-2-yl)methyl]-1H-imidazol-2-yl}benzonitrile

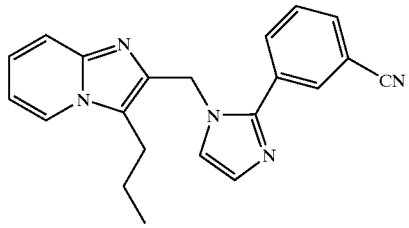

NaH (13.5 mg of 60% wt., 0.34 mmol) is added to a solution of 3-cyano-(1H-imidazol-2-yl)benzene (57.2 mg, 0.34 mmol) in anhydrous DMF (3.5 mL). After 15 minutes, 2-chloromethyl-3-(1-propyl)-imidazolo[1,2-a]pyridine (70.5 mg, 0.34 mmol) is added and the reaction mixture is stirred at ambient temperature for 18 hours. Concentration at reduced pressure followed by purification by chromatography on silica gel (5% MeOH/CHCl₃) provides 3-{1-[(3-propylimidazo[1,2-a]pyridin-2-yl)methyl]-1H-imidazol-2-yl}benzonitrile as a light yellow solid. TLC (5% MeOH/CHCl₃) Rf=0.50. ¹H NMR (CDCl₃): 8.13, s (1H); 8.07, d (1H); 7.90, d (1H); 7.71, d (1H); 7.60, d (1H); 7.58, d (1H); 7.20, dd (1H); 7.14, bs (2H); 6.85, t (1H); 5.32, s (2H); 2.70, t (2H); 1.50, p (2H); 0.90, t (3H). LRMS m/z (M+1) 342.30.

Example 8
Synthesis of 6-Chloro-2-{[2-(3-fluorophenyl)-1H-imidazol-1-yl]methyl}-3-propylimidazo[1,2-A]pyridine

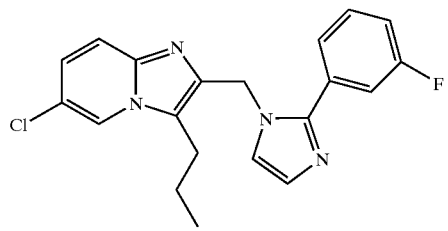

Kt-BuO (0.69 mL of 1 M in THF, 0.69 mmol) is added to a solution of 3-fluoro-(1H-imidazol-2-yl)benzene (88 mg, 0.58 mmol) in anhydrous DMA (1 mL). After 15 minutes, 2-chloromethyl-6-chloro-3-(1-propyl)-imidazolo[1,2-a]pyridine (140 mg, 0.58 mmol) is added and the reaction mixture is stirred and heated at 60° C. for 15 minutes. The reaction mixture is diluted with EtOAc (10 mL), washed with water (3 mL), brine (3 mL), dried over Na₂SO₄, filtered and evaporated at reduced pressure to obtain a yellow solid. Sequential chromatography on silica gel eluting with EtOAc and then 5%MeOH/CH₂Cl₂ provides 6-chloro-2-{[2-(3-fluoropheny)-1H-imidazol-1-yl]methyl}-3-propylimidazo[1,2-a]pyridine as a cream-colored yellow solid. TLC (10% MeOH/CH₂Cl₂) Rf=0.35.

Example 9
Synthesis of 2-{[2-(6-fluoropyridin-2-yl)-1H-imidazol-1-yl]methyl}-3-(trifluoromethyl)imidazo[1,2-A]pyridine
Step 1. Preparation of 3-trifluomethyl-imidazolo[1,2-a]pyridine-2-carboxylate

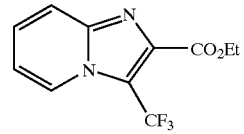

A mixture containing ethyl 3-bromo-imidazolo[1,2-alpyridine-2-carboxylate (1 g, 3.7 mmol), triethyltrifluoromethylsilane (754 mg, 4.09 mmol), copper (I) iodide (779 mg, 4.09 mmol) and potassium fluoride (238 mg, 4.09 mmol) in anhydrous DMF (4.1 mL) is heated at 80° C. with magnetic stirring in a pyrex glass sealed tube. After 40 hours, the resulting dark mixture is poured into a mixture of EtOAc (100 mL) and water/sat. NH₄Cl solution (50 mL, 1:1). After stirring for 1 h, the mixture is filtered to remove solids. The solids are washed with EtOAc (20 mL×3) and the organic layer of the combined filtrates is separated, washed with brine (30 mL), dried over sodium sulfate, filtered and evaporated at reduced pressure to obtain crude product as a dark oil. Purification by radial chromatography using a solvent gradient (35%–45% EtOAc/hexane) provides ethyl 3-trifluomethyl-imidazolo[1,2-a]pyridine-2-carboxylate as a yellow oil. TLC (35% EtOAc/hexane) Rf=0.28.

Step 2. Preparation of 2-hydroxymethyl-3-trifluomethyl-imidazolo[1,2-a]pyridine

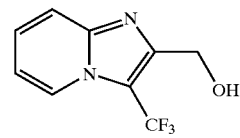

A solution of LiAlH₄ (1M in THF, 0.60 mL, 0.60 mmol) is added to a solution of 3-trifluomethyl-imidazolo[1,2-a]pyridine-2-carboxylate (110 mg, 0.5 mmol) in anhydrous THF (3 mL) at 0° C. under nitrogen with magnetic stirring. The resulting pale yellow solution is allowed to warm to ambient temperature over a 1 hour period and then quenched by addition of 0.35 mL of 2 M aqueous KOH. The resulting mixture is extracted with EtOAc (10 mL×3) and the combined organic layers are dried over anhydrous sodium sulfate, filtered and evaporated at reduced pressure to obtain a pale yellow oil that solidifies on standing. Purification by radial chromatography (35–50% EtOAc/hexane) provides 2-hydroxymethyl-3-trifluomethyl-imidazolo[1,2-a]pyridine as a colorless solid. TLC (5% MeOH/CH₂Cl₂/0.3% NH₄OH) Rf=0.24.

Step 3. Preparation of 2-chloromethyl-3-trifluomethyl-imidazolo[1,2-a]pyridine

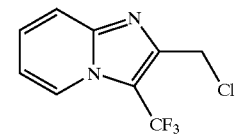

To a solution of 2-hydroxymethyl-3-trifluomethyl-imidazolo[1,2-a]pyridine (70 mg, 0.32 mmol) and anyhydrous triethylamine (72 mg, 0.71 mmol) in CH₂Cl₂ (3.2 mL) at 0° C. under nitrogen methanesulfonyl chloride (39 mg, 0.34 mmol) is added with magnetic stirring. After 1 h, the reaction is diluted with CH₂Cl₂ (30 mL), washed with water (10 mL), dried over anhydrous sodium sulfate, filtered and evaporated at reduced pressure to obtain 2-chloromethyl-3-trifluomethyl-imidazolo[1,2-a]pyridine as a colorless solid. TLC (5% MeOH/CH₂Cl₂/0.3% NH₄OH) Rf=0.75. LRMS m/z (M+1) 235.1.

Step 4. Preparation of 2-{[2-(6-fluoropyridin-2-yl)-1H-imidazol-1-yl]methyl}-3-(trifluoromethyl)imidazo[1,2-a]pyridine

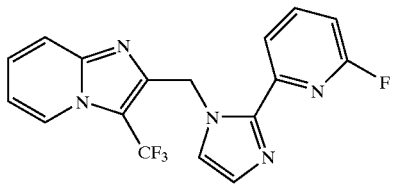

A mixture of 2-chloromethyl-3-trifluomethyl-imidazolo [1,2-a]pyridine (93.7 mg, 0.32 mmol), 2-fluoro-6-(1H-imidazol-2-yl)pyridine (104 mg, 0.64 mmol) and cesium carbonate (211 mg, 0.64 mmol) in DMF (3 mL) is stirred at 50° C. under nitrogen for 8 hours and then at ambient temperature for 16 hours. The reaction mixture is partitioned between EtOAc (30 mL) and water (10 mL), the organic layer is separated, washed with water (10 mL), brine (10 mL), dried over anhydrous sodium sulfate, filtered and evaporated at reduced pressure to obtain a pale yellow solid. Purification by radial chromatography (3% MeOH/CH₂Cl₂/ 0.1% NH₄OH) provides 2-{[2-(6-fluoropyridin-2-yl)-1H-imidazol-1-yl]methyl}-3-(trifluoromethyl)imidazo[1,2-a] pyridine (75.5 mg) as a colorless solid. ¹H NMR (CDCl₃): 8.21 (d, J=6.9 Hz, 1H), 8.10 (m, 1H), 7.82 (dd, J₁=15.9 Hz, J₂=8.2 Hz, 1H), 7.62 (d, J=9.1 Hz, 1H), 7.34 (m, 1H), 7.17 (d, J=1.1 Hz, 1H), 6.98 (m, 1H), 6.82 (m, 1H), 6.18 (s, 2H). LRMS m/z (M+1) 362.2.

Example 10
Synthesis of 6-Chloro-2-[2-(6-fluoro-pyridin-2-yl)-2H-pyrazol-3-ylmethyl]-3-Methyl-Imidazo[1,2-A]Pyridine
Step 1. Preparation of 6-Chloro-2-[2-(2,2-dimethoxy-ethyl)-[1,3]dithian-2-ylmethyl]-3-methyl-imidazol[1,2-a]pyridine

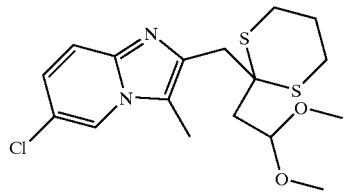

A solution of n-BuLi in hexanes (1.6 M, 1.4 mL) is added dropwise at −50° C. to a solution of 2-(2,2-dimethoxy-ethyl)-[1,3]dithiane (450 mg, prepared according J. Het. Chem, 1987, 1221) in THF. The mixture is then warmed to −30° C. for 1 hour. After cooling to −50° C., a solution of 6-chloro-2-chloromethyl-3-methyl-imidazo[1,2-a]pyridine (300 mg) in 3 mL of THF is added dropwise; the reaction mixture is then slowly warmed to room temperature. After quenching with aqueous NH₄Cl solution, the mixture is extracted with ethyl acetate. The extract is washed with brine, dried over Na₂SO₄ and concentrated under vacuum. The residue is purified on flash chromatographic column, eluting with 5% MeOH in CH₂Cl₂, to give 6-Chloro-2-[2-(2,2-dimethoxy-ethyl)-[1,3]dithian-2-ylmethyl]-3-methyl-imidazo[1,2-a]pyridine. ¹H NMR (CDCl₃, ppm): 7.80 (s, 1H); 7.50(d, 1H); 7.05(d, 1H); 4.80(t, 1H); 3.40(m, 8H); 2.75–3.00(m, 4H); 2.40–2.50(m, 5H); 1.80–2.05(m, 2H).

Step 2. Preparation of 6-Chloro-2-[2-(6-fluoro-pyridin-2-yl)-2H-pyrazol-3-ylmethyl]-3-methyl-imidazol[1,2-a]pyridine

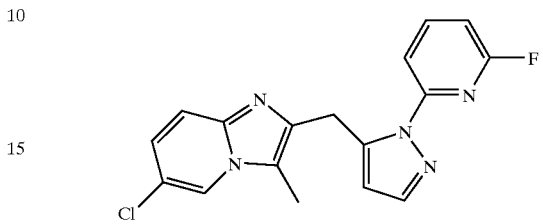

A mixture of 6-Chloro-2-[2-(2,2-dimethoxy-ethyl)-[1,3] dithian-2-ylmethyl]-3-methyl-imidazol[1,2-a]pyridine (200 mg), HgCl₂ (200 mg) and CaCO₃ (100 mg) in a mixed solvent (Acetone/CH₂CN/H₂O, 5/5/5 mL) is stirred at room temperature overnight. Additional HgCl₂ (200 mg) and CaCO₃ (100 mg) are added and then heated at 50° C. for 2 hours. The solvent is evaporated under vacuum, and the residue is partitioned between CH₂Cl₂ and water. The organic layer is separated, washed with water, and concentrated under vacuum. The residue is dissolved in Acetic acid/H₂O (10/1 mL), and the solution is heated at 50° C. for 0.5 hours. After cooling, 20 mg of (6-Fluoro-pyridin-2-yl)-hydrazine is added, and the reaction mixture is then heated at 80° C. overnight. The mixture is evaporated under vacuum, basified with aqueous NaHCO₃, and extracted with CH₂Cl₂. The extracted is washed with brine and concentrated. The residue is purified on a preparative TLC plate, 10% MeOH/CH₂Cl₂ to give 6-Chloro-2-[2-(6-fluoro-pyridin-2-yl)-2H-pyrazol-3-ylmethyl]-3-methyl-imidazo[1, 2-a]pyridine as a white solid. ¹H NMR (CDCl₃, ppm): 7.80–7.90(m, 3H); 7.58(s, 1H); 7.50(d, 1H); 7.11(dd, 1H); 6.80(dd, 1H); 6.08(s, 1H); 4.70(s, 2H); 2.44(s, 3H).

Example 11
Synthesis 1-[3-Ethyl-2-(2-thiazol-2-yl-Imidazo-1-ylmethyl) imidazo[1,2-B]pyrida-Zin-6-yl]ethanone

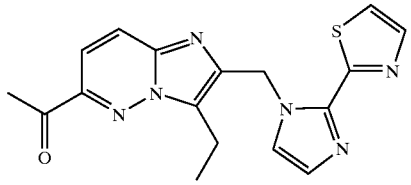

A mixture of 6-chloro-3-ethyl-2-(2-thiazol-2-yl-imidazol-1-ylmethyl)-imidazo[1,2-b]pyridazine (100 mg, 0.26 mmol), 1-ethoxyvinyltributylstannane (142 mg, 0.39 mmol) and PdCl₂(Ph₃P)₂ (10 mg) in anhydrous toluene (5 mL) is heated at 110° C. in a sealed tube for 5 hours. On cooling, water (2 mL), and concentrated HCl (2 mL) are added and the mixture is stirred at room temperature for 2 hours. The mixture is neutralized with sodium carbonate solution and extracted with methylene chloride (3×15 mL). The combined organic layers are dried (Na₂SO₄) and the solvent removed. The residue is purified by PTLC (5% methanol in methylene chloride) to give 1-[3-ethyl-2-(2-thiazol-2-yl-imidazol-1-ylmethyl)imidazo[1,2-b]pyridazin-6-yl]ethanone as a solid. $^1$H NMR (CDCl$_3$): 7.95, d (1H); 7.86, d (1H0; 7.70, d (1H); 7.36, d (1H); 7.25, d (1H); 7.11, d (1H); 6.18, s (2H); 3.10, q (2H); 2.75, s (3H); 1.18, t (3H).

Example 12

Synthesis of 4-[3-Ethyl-2-(2-thiazol-2-yl-imidazol-1-ylmethyl)-imidazo[1,2-B]pyridazin-6-yloxy]-2-methyl-butan-2-ol

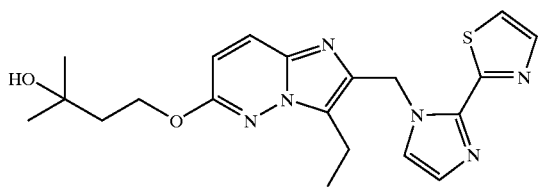

To a solution of 3-methyl-1,3-butandiol (92 mg, 0.88 mmol) in THF (10 mL) under N$_2$ at room temperature is added tBuOK (1M in THF, 0.88 mL, 0.88 mmol). After 5 minutes, 6-chloro-3-ethyl-2-(2-thiazol-2-yl-imidazol-1-ylmethyl)-imidazo[1,2-b]pyridazine (46 mg, 0.12 mmol) is added. The mixture is refluxed for 2.5 hr. On cooling, solvent is removed in vacuo. To the residue is added saturated NH$_4$Cl aqueous solution (8 mL) and extracted with methylene chloride (15×3 mL). The organic layers are combined, dried (Na$_2$SO$_4$) and solvent removed. The crude product is purified by PTLC (10% methanol in methylene chloride) to give 4-[3-ethyl-2-(2-thiazol-2-yl-imidazol-]-ylmethyl)-imidazo[1,2-b]pyridazin-6-yloxyl-2-methyl-butan-2-ol as an oil. $^1$H NMR (CDCl$_3$): 7.88, d (1H); 7.73, d (1H); 7.38, d (1H); 7.21, d (1H); 7.08, d (1H); 6.62, d (1H); 6.02, s (2H); 4.51, t (2H); 2.93, q (2H); 2.21, t (2H); 1.35, s (6H); 1.05, t (3H).

Example 13

Synthesis of 5-Ethyl-6-[2-(6-fluoro-pyridin-2-yl)-imidazol-1-ylmethyl]-Imidazo[2,1-B]thiazole Step 1. Preparation of 5-ethyl-imidazo[2,1-b]thiazole-6-carboxylic acid ethyl ester

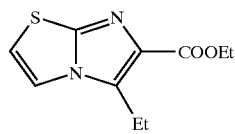

A mixture of 2-aminothiazole (2 g, 20 mmol) and 3-bromo-2-oxo-pentanoic acid ethyl ester (4.4 g, 20 mmol) in ethanol (40 mL) is refluxed for 20 h. The solvent is removed in vacuo until dryness. The residue is purified by column chromatography (5% methanol in methylene chloride) to give 5-ethyl-imidazo[2,1-b]thiazole-6-carboxylic acid ethyl ester as an oil.

Step 2. Preparation of 5-ethyl-6-hydroxymethyl-imidazo[2,1-b]thiazole

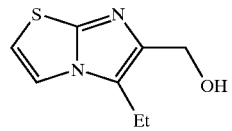

Diisobutylaluminum hydride (1M in THF, 11 mL, 11 mmol) is added to a solution of 5-ethyl-imidazo[2,1-b]thiazole-6-carboxylic acid ethyl ester (800 mg, 3.6 mmol) in THF (20 mL). The mixture is stirred at room temperature for 0.5 h. HCl (10%, 2 mL) is added, and the mixture is stirred for an additional 5 min. The mixture is neutralized by the addition of sodium hydroxide (2 N) until pH is above 10 and then extracted with ethyl acetate (3×20 mL). The combined organic layers are dried and solvent removed to give 5-ethyl-6-hydroxymethyl-imidazo[2,1-b]thiazole as a solid.

Step 3. Preparation of 6-chloromethyl-5-ethyl-imidazo[2,1-b]thiazole

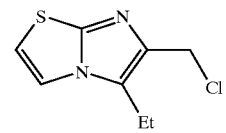

Thionyl chloride (2M in methylene chloride, 10 mL) is added to 5-ethyl-imidazo[2,1-b]thiazol-6-yl)methanol (700 mg, 3.8 mmol) is added. The mixture is stirred at room temperature for 0.5 h. All volatile material is removed until dryness to give 6-chloromethyl-5-ethyl-imidazo[2,1-b]thiazole as a solid.

Step 4. Preparation of 5-ethyl-6-[2-(6-fluoro-pyridin-2-yl)-imidazol-1-ylmethyl]-imidazo[2,1-b]thiazole

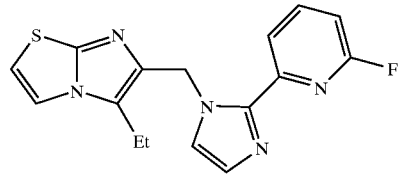

A mixture of 6-chloromethyl-5-ethyl-imidazo[2,1-b]thiazole (120 mg, 0.6 mmol), 2-fluoro-6-(1H-imidazol-2-yl)pyridine (82 mg, 0.6 mmol) and potassium carbonate (278 mg, 2.4 mmol) in DMF (6 mL) is stirred at room temperature for 48 h. Brine (15 mL) and methylene chloride (20 mL) are added. The organic layer is separated and the aqueous layer is extracted with methylene chloride (2×20 mL). The combined organic layers are washed with brine (3×15 mL) and dried. The solvent is removed in vacuo. The residue is purified by preparative TLC to give 32 mg of 5-ethyl-6-[2-(6-fluoro-pyridin-2-yl)-imidazol-1-ylmethyl]-imidazo[2,1-b]thiazole as an oil. $^1$H NMR (CDCl$_3$): 8.10, dd (1H); 7.82, dd (1H); 7.35, d (1H); 7.26, d (1H); 7.12, d (1H); 6.83, dd (1H); 6.80, d (1H); 5.92, s (2H); 2.90, q (2H); 1.07, t (3H).

Example 14

Additional Compounds of the Invention

The compounds shown in Tables 1–8 are prepared according to the methods given in Schemes 1–9 and further illustrated by Examples 1–13. "X" shown in the table cells indicates the point of attachment of the group in the structure shown at the top of that table.

TABLE 1

| CMP # | Name | W | R5 | R4 | R3 | R2 | 1H NMR | Mass Spec (Cald./Obs. M + 1) |
|---|---|---|---|---|---|---|---|---|
| 13 | 6-chloro-2-[(2-phenyl-1H-imidazol-1-yl)methyl]-3-propylimidazo[1,2-a]pyridine | phenyl (X₁) | X₃—CH₂CH₂CH₃ | H | Cl—X₅ | H | | 350.1/351.2 |
| 14 | 6-chloro-2-{[2-(3-fluorophenyl)-1H-imidazol-1-yl]methyl}imidazo[1,2-a]pyridine | 3-fluorophenyl (X₁) | H | H | Cl—X₅ | H | | 326.1/327.1 |
| 15 | 6-chloro-2-{[2-(3-chlorophenyl)-1H-imidazol-1-yl]methyl}imidazo[1,2-a]pyridine | 3-chlorophenyl (X₁) | H | H | Cl—X₅ | H | | 342.0/343.1 |
| 16 | 6-chloro-2-{[2-(3-fluorophenyl)-1H-imidazol-1-yl]methyl}-3-propylimidazo[1,2-a]pyridine | 3-fluorophenyl (X₁) | X₃—CH₂CH₂CH₃ | H | Cl—X₅ | H | | 368.1/369.2 |

TABLE 1-continued

| CMP # | Name | W | R5 | R4 | R3 | R2 | 1H NMR | Mass Spec (Cald./Obs. M + 1) |
|---|---|---|---|---|---|---|---|---|
| 17 | 3-ethyl-2-[[2-(3-fluorophenyl)-1H-imidazol-1-yl]methyl]imidazo[1,2-a]pyridine-7-carbonitrile | 3-fluorophenyl (X₁) | X₃-CH₂-CH₃ | H | H | N≡C-X₆ | | 345.1/346.2 |
| 18 | 3-ethyl-2-[[2-(6-fluoropyridin-2-yl)-1H-imidazol-1-yl]methyl]imidazo[1,2-a]pyridine-7-carbonitrile | 6-fluoropyridin-2-yl (X₁) | X₃-CH₂-CH₃ | H | H | N≡C-X₆ | | 346.6/347.3 |
| 19 | 3-ethyl-2-[(2-phenyl-1H-imidazol-1-yl)methyl]imidazo[1,2-a]pyridine | phenyl (X₁) | X₃-CH₂-CH₃ | H | H | H | 1Hnmr(CDCl3, 400 MHz)-7.85(1H, dd), 7.72–7.70(2H, m), 7.57(1H, dd). 7.49–7.42(3H, m), 7.19–7.10(1H, m), 7.10(2H, m), 6.83–6.80(1H, m), 5.35(2H, s), 2.59(2H, q), 0.99(3H, t), Å1H, m), 5.35(2H, s), 2.59(2H, q), 0.99(3H, t). | 302.4/303.2 |
| 20 | 3-ethyl-2-[[2-(3-fluorophenyl)-1H-imidazol-1-yl]methyl]imidazo[1,2-a]pyridine | 3-fluorophenyl (X₁) | X₃-CH₂-CH₃ | H | H | H | 1Hnmr(CDCl3, 400 MHz)-7.88(1H, dd), 7.58(1H, dd), 7.54–7.42(3H, m), 7.21–7.10(4H, m), 6.84(1H, t), 5.35(2H, s), 2.65(2H, q), 1.04(3H, t). | 320.4/321.3 |

TABLE 1-continued

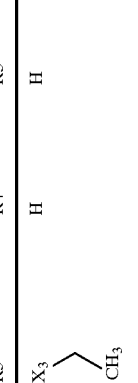

| CMP # | Name | W | R5 | R4 | R3 | R2 | 1H NMR | Mass Spec (Cald./Obs.) M + 1 |
|---|---|---|---|---|---|---|---|---|
| 21 | 3-ethyl-2-[[2-(6-fluoropyridin-2-yl)-1H-imidazol-1-yl]methyl]imidazo[1,2-a]pyridine | 6-fluoropyridin-2-yl (X₁) | X₃-CH₂-CH₃ | H | H | H | 1Hnmr(CDCl3, 400 MHz)- 8.13–8.10(1H, m), 7.90–7.82(2H, m), 7.57(1H, dd), 7.32(1H, s), 7.17–7.13(1H, m), 7.11(1H, s), 6.87(1H, dd), 6.81(1H, t), 6.08(2H, s), 3.00(2H, q), 1.06(3H, t). | 321.4/322.3 |
| 22 | 7-chloro-2-[[2-(6-fluoropyridin-2-yl)-1H-imidazol-1-yl]methyl]-3-propylimidazo[1,2-a]pyridine | 2,6-difluoropyridinyl (X₁) | X₃-CH₂-CH₂-CH₃ | H | H | Cl (X₆) | free base in CDCl3: 8.12, dd(1H); 7.85, dd(1H); 7.78, dd(1H); 7.56, dd(1H); 7.32, ddd(1H); 7.10, dd(1H); 6.87, dd(1H); 6.77, dd(1H); 2.91, t(2H); 1.45, p(2H); 0.88, t(3H) | 369.12/370.19 |
| 23 | 6-chloro-2-[[2-(6-fluoropyridin-2-yl)-1H-imidazol-1-yl]methyl]-3-propylimidazo[1,2-a]pyridine | 6-fluoropyridin-2-yl (X₁) | X₃-CH₂-CH₂-CH₃ | H | Cl (X₅) | H | free base in CDCl3: 8.11, dd(1H); 7.89, d(1H); 7.85, dd(1H); 7.51, d(1H); 7.32, d(1H); 7.26, m(1H); 7.11, d(1H); 7.09, dd(1H); 6.04, s(2H); 2.94, t(2H); 1.51, p(2H); 0.84, t(3H) | 369.12/371.90 |
| 24 | 7-chloro-2-[[2-(6-fluoropyridin-2-yl)-1H-imidazol-1-yl]methyl]imidazo[1,2-a]pyridine | 6-fluoropyridin-2-yl (X₁) | X₃-CH₂-CH₃ | H | H | Cl (X₆) | free base in CDCl3: 8.12, dd(1H); 7.81, d(1H); 7.57, d(1H); 7.31, s(1H); 7.12, s(1H); 6.88, dd(1H); 6.80, dd(1H); 6.07, s(1H); 3.01, q(2H); 1.06, t(3H) | 355.10/356.20 |
| 25 | 7-chloro-3-ethyl-2-[[2-(3-fluorophenyl)-1H-imidazol-1-yl]methyl]imidazo[1,2-a]pyridine | 3-fluorophenyl (X₁) | X₃-CH₂-CH₃ | H | H | Cl (X₆) | free base in CDCl3: 7.80, d(1H); 7.58, d(1H); 7.44, m(3H); 7.13, m(3H); 6.82, dd(1H); 5.32, s(2H); 2.64, q(2H); 1.04, t(3H) | 354.10/355.20 |

TABLE 1-continued

| CMP # | Name | W | R5 | R4 | R3 | R2 | 1H NMR | Mass Spec (Cald./Obs. M + 1) |
|---|---|---|---|---|---|---|---|---|
| 26 | 3-{1-[(3-propylimidazo[1,2-a]pyridin-2-yl)methyl]-1H-imidazol-2-yl}benzonitrile | 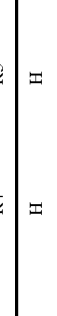 |  | H | H | H | free base in CDCl3: 8.13, s(1H); 8.07, d(1H); 7.90, d(1H); 7.71, d(1H); 7.60, d(1H); 7.58, d(1H); 7.20, dd(1H); 7.14, bs(2H); 6.85, t(1H); 5.32, s(2H); 2.70, t(2H); 1.50, p(2H); 0.90, t(3H) | 341.16/342.30 |
| 27 | 3-ethyl-6-fluoro-2-{(2-(6-fluoropyridin-2-yl)-1H-imidazol-1-yl]methyl}imidazo[1,2-a]pyridine | 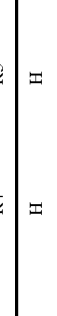 |  | H |  | H | free base in CDCl3: 8.14, dd(1H); 7.86, dd(1H); 7.81, m(1H); 7.55, dd(1H); 7.27, m(1H); 7.07, m(2H); 6.88, dd(1H); 6.08, s(2H); 2.98, q(2H); 1.06, t(3H) | 339.13/3340.20 |
| 28 | 3-ethyl-6-fluoro-2-{[2-(3-fluorophenyl)-1H-imidazol-1-yl]methyl}imidazo[1,2-a]pyridine | 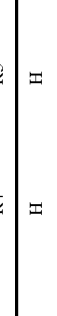 |  | H |  | H | free base in CDCl3: 8.14, dd(1H); 7.86, dd(1H); 7.81, m(1H); 7.55, dd(1H); 7.27, m(1H); 7.08, m(2H); 6.88, dd(1H); 6.08, s(2H); 2.98, q(2H); 1.06, t(3H) | 338.13/339.20 |
| 29 | 2-{[2-(3-chlorophenyl)-1H-imidazol-1-yl]methyl}-3-ethyl-6-fluoroimidazo[1,2-a]pyridine | 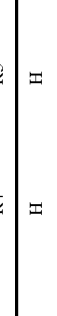 |  | H | F | H | free base in CDCl3: 7.80, m(2H); 7.61, m(1H); 7.55, m(1H); 7.39, d(1H); 7.28, m(1H); 7.10, m(3H); 5.32, s(1H); 2.65, q(2H); 1.06, t(3H) | 354.10/355.20 |
| 30 | 2-{[2-(2,5-difluorophenyl)-1H-imidazol-1-yl]methyl}-3-ethyl-6-fluoroimidazo[1,2-a]pyridine |  | 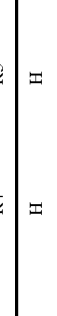 | H |  | H | free base in CDCl3: 7.86, m(1H); 7.54, dd(1H); 7.35, m(1H); 7.17, m(5H); 5.21, s(2H); 2.62, q(2H); 1.02, t(3H) | 356.12/357.20 |

TABLE 1-continued

| CMP # | Name | W | R5 | R4 | R3 | R2 | 1H NMR | Mass Spec (Cald./Obs. M + 1) |
|---|---|---|---|---|---|---|---|---|
| 31 | 3-{1-[(3-ethylimidazo[1,2-a]pyridin-2-yl)methyl]-1H-imidazol-2-yl}benzonitrile | 3-cyanophenyl (X1) | X3-CH2-CH3 | H | H | H | tartrate salt in CD3OD: 8.26, d(1H); 8.06, s(1H); 8.00, d(1H); 7.85, d(1H); 7.69, t(1H); 7.50, d(1H); 7.35, t(1H); 7.29, s(1H); 7.19, s(1H); 6.99, t(1H); 5.46, s(2H); 4.50, s(2H); 2.85, q(2H), 1.11, t(3H) | 327.15/328.30 |
| 32 | 6-bromo-2-{[2-(3-fluorophenyl)-1H-imidazol-1-yl]methyl}-3-propylimidazo[1,2-a]pyridine | 3-fluorophenyl (X1) | X3-CH2-CH2-CH3 | H | Br (X5) | H | free base in CDCl3: 7.99, d(1H); 7.48, m(4H); 7.24, dd(1H); 7.15, dd(1H); 7.11, bs(1H); 5.32, s(2H); 2.57, t(2H); 1.43, p(2H), 0.84, t(3H) | 412.07/415.00 |
| 33 | 3-ethyl-2-{[2-(3-fluorophenyl)-1H-imidazol-1-yl)methyl}-6-(5-methyl-1,3,4-oxadiazol-2-yl)imidazo[1,2-a]pyridine | 3-fluorophenyl (X1) | X3-CH2-CH3 | H | 5-methyl-1,3,4-oxadiazol-2-yl (X5) | H | free base in CDCl3: 8.62, d(1H); 7.77, dd(1H); 7.69, dd(1H); 7.49, m(3H); 7.15, m(3H); 5.37, s(2H); 2.74, q(2H), 2.66, s(3H); 1.11, t(3H) | 402.16/403.40 |
| 34 | 6-chloro-2-{[2-(6-fluoropyridin-2-yl)-1H-imidazol-1-yl]methyl}-3-methylimidazo[1,2-a]pyridine | 6-fluoropyridin-2-yl (X1) | X3-CH3 | H | Cl (X5) | H | | 341.7/342.0 |
| 35 | 6-chloro-2-{[2-(3-fluorophenyl)-1H-imidazol-1-yl]methyl}-3-methylimidazo[1,2-a]pyridine | 3-fluorophenyl (X1) | X3-CH3 | H | Cl (X5) | H | | 340.7/341.0 |

TABLE 1-continued

| CMP # | Name | W | R5 | R4 | R3 | R2 | 1H NMR | Mass Spec (Cald./Obs. M + 1) |
|---|---|---|---|---|---|---|---|---|
| 36 | 6-chloro-3-ethyl-2-{[2-(6-fluoropyridin-2-yl)-1H-imidazol-1-yl]methyl}imidazo[1,2-a]pyridine | 6-fluoropyridin-2-yl (F at 6, X1 at 2) | X3—CH2CH3 | H | Cl—X5 | H | | 355.8/356.0 |
| 37 | 6-chloro-3-ethyl-2-{[2-(3-fluoropyridin-2-yl)-1H-imidazol-1-yl]methyl}imidazo[1,2-a]pyridine | 3-fluoropyridin-2-yl | X3—CH2CH3 | H | Cl—X5 | H | | 355.8/356.7 |
| 38 | 2-{[2-(6-fluoropyridin-2-yl)-1H-imidazol-1-yl]methyl}imidazo[1,2-a]pyridine-3-carbonitrile | 6-fluoropyridin-2-yl | X3—C≡N | H | H | H | | 318.32/319.2 |
| 39 | 2-{[2-(3-fluoropyridin-2-yl)-1H-imidazol-1-yl]methyl}imidazo[1,2-a]pyridine-3-carbonitrile | 3-fluoropyridin-2-yl | X3—C≡N | H | H | H | Free base in CDCl3: 8.56, dd(1H); 8.26, dd(1H); 7.67, d(1H); 7.53, (1H); 7.51–7.43, m(3H); 7.41–7.29, m(2H), 7.08, t(1H); 5.93, s(2H) | |
| 40 | 2-{[2-(6-fluoropyridin-2-yl)-1H-imidazol-1-yl]methyl}-3,6-dimethylimidazo[1,2-a]pyridine | 6-fluoropyridin-2-yl | X3—CH3 | H | X5—CH3 | H | | 321.3/322.0 |

TABLE 1-continued

| CMP # | Name | W | R5 | R4 | R3 | R2 | 1H NMR | Mass Spec (Cald./Obs. M + 1) |
|---|---|---|---|---|---|---|---|---|
| 41 | 2-[[2-(3-fluorophenyl)-1H-imidazol-1-yl]methyl]-3,6-dimethylimidazo[1,2-a]pyridine | 3-fluorophenyl (X1) | X3–CH3 | H | X5–CH3 | H | | 320.3/321.0 |
| 42 | 7-ethyl-2-[[2-(6-fluoropyridin-2-yl)-1H-imidazol-1-yl]methyl]-3-methylimidazo[1,2-a]pyridine | 6-fluoropyridin-2-yl (X1) | X3–CH3 | H | H | H | | 335.3/336.0 |
| 43 | 7-ethyl-2-[[2-(3-fluorophenyl)-1H-imidazol-1-yl]methyl]-3-methylimidazo[1,2-a]pyridine | 3-fluorophenyl (X1) | X3–CH3 | X4–CH3 | H | CH3–X6 | | 334.3/335.8 |
| 44 | 5-ethyl-2-[[2-(6-fluoropyridin-2-yl)-1H-imidazol-1-yl]methyl]-3-methylimidazo[1,2-a]pyridine | 6-fluoropyridin-2-yl (X1) | X3–CH3 | H | H | H | | 335.3/336.0 |

TABLE 1-continued

| CMP # | Name | W | R5 | R4 | R3 | R2 | 1H NMR | Mass Spec (Cald./Obs. M + 1) |
|---|---|---|---|---|---|---|---|---|
| 45 | 1-(2-{[2-(3-fluorophenyl)-1H-imidazol-1-yl]methyl})-3-methylimidazo[1,2-a]pyridin-5-yl)ethanol | 3-fluorophenyl (X1) | X3—CH3 | X4—CH(CH3)OH | H | H | | 350.3/351.2 |
| 46 | 6-chloro-2-{[2-(2,5-difluorophenyl)-1H-imidazol-1-yl]methyl}-3-methylimidazo[1,2-a]pyridine | 2,5-difluorophenyl (X1) | X3—CH3 | H | Cl—X5 | H | free base in CDCl3: 7.82, d(1H); 7.46, d(1H); 7.28, m(1H); 7.12, m(5H); 5.20, s(2H); 2.13, s(3H) | |
| 47 | 6-chloro-2-{[2-(5-fluoro-2-methylphenyl)-1H-imidazol-1-yl]methyl}-3-methylimidazo[1,2-a]pyridine | 5-fluoro-2-methylphenyl (X1) | X3—CH3 | H | Cl—X5 | H | free base in CDCl3: 7.81, d(1H); 7.48, dd(1H); 7.21, m(2H); 7.16, d(1H); 7.12, d(1H); 7.06, m(2H); 5.04, s(2H); 2.12, s(3H); 2.05, s(3H) | |
| 48 | 2-{[2-(6-fluoropyridin-2-yl)-1H-imidazol-1-yl]methyl}-3,5,7-trimethylimidazo[1,2-a]pyridine | 6-fluoropyridin-2-yl (X1) | X3—CH3 | X4—CH3 | H | CH3 X6 | | 335.38/336.21 |

TABLE 1-continued

| CMP # | Name | W | R5 | R4 | R3 | R2 | 1H NMR | Mass Spec (Cald./Obs. M + 1) |
|---|---|---|---|---|---|---|---|---|
| 49 | 2-[[2-(3-fluoropyridin-2-yl)-1H-imidazol-1-yl]methyl]-3,5,7-trimethylimidazo[1,2-a]pyridine | 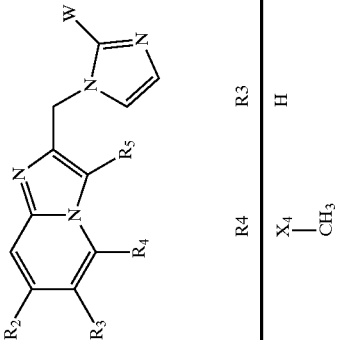 | X₃—CH₃ | X₄—CH₃ | H | CH₃—X₆ | | 335.38/336.20 |
| 50 | 2-[[2-(6-fluoropyridin-2-yl)-1H-imidazol-1-yl]methyl]-3-(trifluoromethyl)imidazo[1,2-a]pyridine | 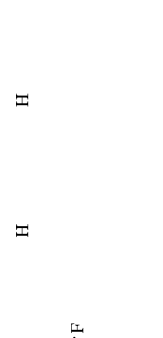 | X₃—CF₃ | H | H | H | | 361.1/362.2 |
| 51 | 2-[[2-(6-fluoropyridin-2-yl)-1H-imidazol-1-yl]methyl]-3-methyl-6-(trifluoromethyl)imidazo[1,2-a]pyridine |  | X₃—CH₃ | H | X₅—CF₃ | H | | 375.32/376.20 |
| 52 | 2-[[2-(3-fluorophenyl)-1H-imidazol-1-yl]methyl]-3-(trifluoromethyl)imidazo[1,2-a]pyridine |  | X₃—CH₃ | H | X₅—CF₃ | H | | 374.34/375.10 |
| 53 | 3-bromo-2-[[2-(6-fluoropyridin-2-yl)-1H-imidazol-1-yl]methyl]imidazo[1,2-a]pyridine |  | X₃—Br | H | H | H | | 371.0/373.9 |

TABLE 1-continued

| CMP # | Name | W | R5 | R4 | R3 | R2 | 1H NMR | Mass Spec (Cald./Obs. M + 1) |
|---|---|---|---|---|---|---|---|---|
| 54 | 3-ethyl-2-([2-pyrimidin-2-yl-1H-imidazol-1-yl]methyl)-6-(trifluoromethyl)imidazo[1,2-a]pyridine |  |  | H |  | H | | 372.35/373.20 |
| 55 | 3-ethyl-2-[[2-(1,3-thiazol-2-yl)-1H-imidazol-1-yl]methyl]-6-(trifluoromethyl)imidazo[1,2-a]pyridine | 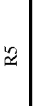 |  | H |  | H | | 377.39/378.30 |
| 56 | 3-ethyl-2-[[2-(1,3-thiazol-2-yl)-1H-imidazol-1-yl]methyl]-5-(ethyl)imidazo[1,2-a]pyridine |  |  | H | H | 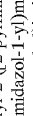 | | 337.44/338.20 |
| 57 | 3-ethyl-2-[[2-(1,3-thiazol-2-yl)-1H-imidazol-1-yl]methyl]-6-(acetyl)imidazo[1,2-a]pyridine |  |  | H |  | H | | 337.41/378.3 |
| 58 | 3-ethyl-2-[[2-(1,3-thiazol-2-yl)-1H-imidazol-1-yl]methyl]-6-(bromo)imidazo[1,2-a]pyridine | | | H | | H | free base in CDCl3: 8.00, s(1H); 7.85, dd(1H); 7.45, d(1H); 7.35, d(1H); 7.25, s(1H); 7.20, d(1H); 7.10, s(1H); 6.10, s(2H); 2.90, q(2H); 1.00, t(3H) | |

TABLE 1-continued

| CMP # | Name | W | R5 | R4 | R3 | R2 | 1H NMR | Mass Spec (Cald./Obs.) M + 1 |
|---|---|---|---|---|---|---|---|---|
| 59 | 3-ethyl-2-{[2-(1,3-thiazol-2-yl)-1H-imidazol-1-yl]methyl}-6-(thien-2-yl)imidazo[1,2-a]pyridine | thiazole-X1 | X3-CH2-CH3 | H | thien-2-yl-X5 | H | | 377.49/380.3 |
| 60 | 3-ethyl-2-{[2-(1,3-thiazol-2-yl)-1H-imidazol-1-yl]methyl}-6-(1,3-thiazol-2-yl)imidazo[1,2-a]pyridine | thiazole-X1 | X3-CH2-CH3 | H | thiazol-2-yl-X5 | H | | 378.48/379.5 |
| 61 | 3-ethyl-2-{[2-(1,3-thiazol-2-yl)-1H-imidazol-1-yl]methyl}-6-(pyridin-2-yl)imidazo[1,2-a]pyridine | thiazole-X1 | X3-CH2-CH3 | H | pyridin-2-yl-X5 | H | | 372.45/373.3 |
| 62 | 3-ethyl-2-{[2-(1,3-thiazol-2-yl)-1H-imidazol-1-yl]methyl}-6-(pyridin-4-yl)imidazo[1,2-a]pyridine | thiazole-X1 | X3-CH2-CH3 | H | pyridin-4-yl-X5 | H | | 372.45/373.3 |
| 63 | 3-ethyl-2-{[2-(1,3-thiazol-2-yl)-1H-imidazol-1-yl]methyl}-6-(cyano)imidazo[1,2-a]pyridine | thiazole-X1 | X3-CH2-CH3 | H | N≡C-X6 | H | | 334.41/335.20 |

TABLE 2

| Cmp. # | Name | W | R5 | R3 | 1H NMR | Mass Spec (Cald./Obs. M + 1) |
|---|---|---|---|---|---|---|
| 64 | 6-chloro-2-{[2-(3-fluorophenyl)-1H-imidazol-1-yl]methyl}imidazo[1,2-b]pyridazine | 3-fluorophenyl (X1) | H | Cl | | 327.1/328.2 |
| 65 | 3-bromo-6-chloro-2-{[2-(3-fluorophenyl)-1H-imidazol-1-yl]methyl}imidazo[1,2-b]pyridazine | 3-fluorophenyl (X1) | Br | Cl | | 405.0/406.0 |
| 66 | 6-chloro-2-{[2-(6-fluoropyridin-2-yl)-1H-imidazol-1-yl]methyl}-3-propylimidazo[1,2-b]pyridazine | 6-fluoropyridin-2-yl (X1) | X3-CH2CH2CH3 | Cl | | 370.1/371.2 |
| 67 | 3-bromo-6-chloro-2-{[2-(6-fluoropyridin-2-yl)-1H-imidazol-1-yl]methyl}imidazo[1,2-b]pyridazine | 6-fluoropyridin-2-yl (X1) | Br | Cl | | 406.0/407.1 |
| 68 | 2-{[2-(6-fluoropyridin-2-yl)-1H-imidazol-1-yl]methyl}-3-propylimidazo[1,2-b]pyridazine | 6-fluoropyridin-2-yl (X1) | X3-CH2CH2CH3 | H | | 336.2/337.2 |
| 69 | 2-{[2-(6-fluoropyridin-2-yl)-1H-imidazol-1-yl]methyl}imidazo[1,2-b]pyridazine | 6-fluoropyridin-2-yl (X1) | H | H | | 294.1/295.3 |
| 70 | 3-bromo-6-chloro-2-{[2-(6-chloropyridin-2-yl)-1H-imidazol-1-yl]methyl}imidazo[1,2-b]pyridazine | 6-chloropyridin-2-yl (X1) | Br | Cl | | 421.9/423.0 |
| 71 | 6-chloro-2-{[2-(4-chloropyridin-2-yl)-1H-imidazol-1-yl]methyl}-3-propylimidazo[1,2-b]pyridazine | 6-chloropyridin-2-yl (X1) | X3-CH2CH2CH3 | Cl | | 386.1/387.2 |

TABLE 2-continued

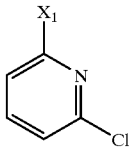

| Cmp. # | Name | W | R5 | R3 | 1H NMR | Mass Spec (Cald./Obs. M + 1) |
|---|---|---|---|---|---|---|
| 72 | 6-chloro-2-{[2-(6-chloropyridin-2-yl)-1H-imidazol-1-yl]methyl}-3-propylimidazo[1,2-b]pyridazine | 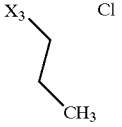 | 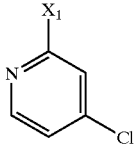 | Cl | | 386.1/387.2 |
| 73 | 3-bromo-6-chloro-2-{[2-(4-chloropyridin-2-yl)-1H-imidazol-1-yl]methyl}imidazo[1,2-b]pyridazine | 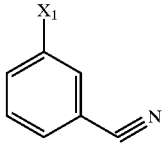 | Br | Cl | | |
| 74 | 3-{1-[(6-chloro-3-propylimidazo[1,2-b]pyridazin-2-yl)methyl]-1H-imidazol-2-yl}benzonitrile | 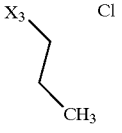 | 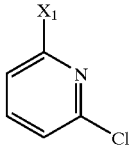 | Cl | | 376.1/377.5 |
| 75 | 6-chloro-2-{[2-(6-chloropyridin-2-yl)-1H-imidazol-1-yl]methyl}-3-ethylimidazo[1,2-b]pyridazine | 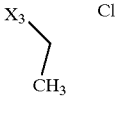 | 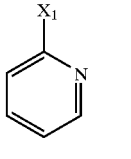 | Cl | | 372.1/373.1 |
| 76 | 3-propyl-2-[(2-pyridin-2-yl-1H-imidazol-1-yl)methyl]imidazo[1,2-b]pyridazine | 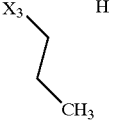 | 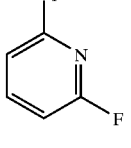 | H | | 318.2/319.4 |
| 77 | 6-chloro-2-{[2-(6-fluoropyridin-2-yl)-1H-imidazol-1-yl]methyl}-3-methylimidazo[1,2-b]pyridazine | 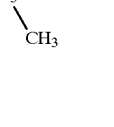 | 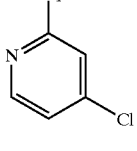 | Cl | | 342.1/343.2 |
| 78 | 6-chloro-2-{[2-(4-chloropyridin-2-yl)-1H-imidazol-1-yl]methyl}-3-methylimidazo[1,2-b]pyridazine | 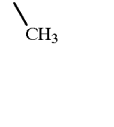 | 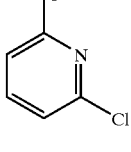 | Cl | | 358.0/359.1 |
| 79 | 6-chloro-2-{[2-(6-chloropyridin-2-yl)-1H-imidazol-1-yl]methyl}-3-methylimidazo[1,2-b]pyridazine | 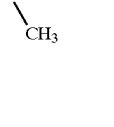 |  | Cl | | 358.0/359.1 |

TABLE 2-continued

| Cmp. # | Name | W | R5 | R3 | 1H NMR | Mass Spec (Cald./Obs. M + 1) |
|---|---|---|---|---|---|---|
| 80 | 2-{[2-(6-fluoropyridin-2-yl)-1H-imidazol-1-yl]methyl}-3-methylimidazo[1,2-b]pyridazine | X₁ 6-fluoropyridin-2-yl | X₃ CH₃ | H | | 308.1/309.2 |
| 81 | 6-chloro-2-{[2-(4-chloropyridin-2-yl)-1H-imidazol-1-yl]methyl}-3-ethylimidazo[1,2-b]pyridazine | X₁ 4-chloropyridin-2-yl | X₃ CH₂CH₃ | Cl | | 372.1/373.1 |
| 82 | 3-ethyl-2-{[2-(6-fluoropyridin-2-yl)-1H-imidazol-1-yl]methyl}imidazo[1,2-b]pyridazine | X₁ 6-fluoropyridin-2-yl | X₃ CH₂CH₃ | H | | 322.1/323.7 |
| 83 | 3-methyl-2-[(2-pyridin-2-yl-1H-imidazol-1-yl)methyl]imidazo[1,2-b]pyridazine | X₁ pyridin-2-yl | X₃ CH₃ | H | | 290.1/291.2 |
| 84 | 3-ethyl-2-[(2-pyridin-2-yl-1H-imidazol-1-yl)methyl]imidazo[1,2-b]pyridazine | X₁ pyridin-2-yl | X₃ CH₂CH₃ | H | | 304.1/305.2 |
| 85 | 3-{1-[(6-chloro-3-ethylimidazo[1,2-b]pyridazin-2-yl)methyl]-1H-imidazol-2-yl}benzonitrile | X₁ 3-cyanophenyl | X₃ CH₂CH₃ | Cl | | 362.1/363.2 |
| 86 | 3-{1-[(3-propylimidazo[1,2-b]pyridazin-2-yl)methyl]-1H-imidazol-2-yl}benzonitrile | X₁ 3-cyanophenyl | X₃ CH₂CH₂CH₃ | H | | 342.2/343.2 |
| 87 | 6-chloro-2-{[2-(2-fluorophenyl)-1H-imidazol-1-yl]methyl}-3-propylimidazo[1,2-b]pyridazine | X₁ 2-fluorophenyl | X₃ CH₂CH₂CH₃ | Cl | | 369.1/370.2 |

TABLE 2-continued

| Cmp. # | Name | W | R5 | R3 | 1H NMR | Mass Spec (Cald./Obs. M + 1) |
|---|---|---|---|---|---|---|
| 88 | 6-chloro-3-ethyl-2-{[2-(3-fluorophenyl)-1H-imidazol-1-yl]methyl}imidazo[1,2-b]pyridazine | $X_1$, 3-F-phenyl | $X_3$, ethyl | Cl | | 355.1/356.1 |
| 89 | 2-{1-[(6-chloro-3-propylimidazo[1,2-b]pyridazin-2-yl)methyl]-1H-imidazol-2-yl}benzonitrile | $X_1$, 2-CN-phenyl | $X_3$, propyl | Cl | | 376.1/377.2 |
| 90 | 6-chloro-2-{[2-(2-fluoropyridin-4-yl)-1H-imidazol-1-yl]methyl}-3-propylimidazo[1,2-b]pyridazine | $X_1$, 2-F-pyridin-4-yl | $X_3$, propyl | Cl | | 370.1/371.2 |
| 91 | 6-chloro-2-{[2-(2-chloropyridin-3-yl)-1H-imidazol-1-yl]methyl}-3-propylimidazo[1,2-b]pyridazine | $X_1$, 2-Cl-pyridin-3-yl | $X_3$, propyl | Cl | | 386.1/387.1 |
| 92 | 3-propyl-2-[(2-pyridin-3-yl-1H-imidazol-1-yl)methyl]imidazo[1,2-b]pyridazine | $X_1$, pyridin-3-yl | $X_3$, propyl | H | | 318.2/319.4 |
| 93 | 6-chloro-3-ethyl-2-{[2-(2-fluorophenyl)-1H-imidazol-1-yl]methyl}imidazo[1,2-b]pyridazine | $X_1$, 2-F-phenyl | $X_3$, ethyl | Cl | | 355.1/356.2 |
| 94 | 6-chloro-2-{[2-(3-fluoropyridin-2-yl)-1H-imidazol-1-yl]methyl}-3-propylimidazo[1,2-b]pyridazine | $X_1$, 3-F-pyridin-2-yl | $X_3$, propyl | Cl | | 370.1/371.3 |
| 95 | 6-chloro-3-propyl-2-({2-[2-(trifluoromethyl)phenyl]-1H-imidazol-1-yl}methyl)imidazo[1,2-b]pyridazine | $X_1$, 2-CF$_3$-phenyl | $X_3$, propyl | Cl | | 419.1/420.2 |

TABLE 2-continued

| Cmp. # | Name | W | R5 | R3 | 1H NMR | Mass Spec (Cald./Obs. M + 1) |
|---|---|---|---|---|---|---|
| 96 | 6-chloro-2-{[2-(2-chlorophenyl)-1H-imidazol-1-yl]methyl}-3-propylimidazo[1,2-b]pyridazine | 2-chlorophenyl | propyl | Cl | | 385.1/386.2 |
| 97 | 6-chloro-3-methyl-2-({2-[2-(trifluoromethyl)phenyl]-1H-imidazol-1-yl}methyl)imidazo[1,2-b]pyridazine | 2-(trifluoromethyl)phenyl | methyl | Cl | | 391.1/392.2 |
| 98 | 6-chloro-2-({2-[3-(methylsulfonyl)phenyl]-1H-imidazol-1-yl}methyl)-3-propylimidazol[1,2-b]pyridazine | 3-(methylsulfonyl)phenyl | propyl | Cl | | 429.1/430.3 |
| 99 | 6-chloro-3-propyl-2-({2-[5-(trifluoromethyl)pyridin-2-yl]-1H-imidazol-1-yl}methyl)imidazo[1,2-b]pyridazine | 5-(trifluoromethyl)pyridin-2-yl | propyl | Cl | | 420.1/421.3 |
| 100 | 6-chloro-2-{[2-(2-piperidin-1-ylpyridin-3-yl)-1H-imidazol-1-yl]methyl}-3-propylimidazo[1,2-b]pyridazine | 2-piperidin-1-ylpyridin-3-yl | propyl | Cl | | 435.2/436.3 |
| 101 | 6-chloro-3-propyl-2-({2-[6-(trifluoromethyl)pyridin-2-yl]-1H-imidazol-1-yl}methyl)imidazo[1,2-b]pyridazine | 6-(trifluoromethyl)pyridin-2-yl | propyl | Cl | | 420.1/421.2 |
| 102 | 6-{1-[(6-chloro-3-propylimidazo[1,2-b]pyridazin-2-yl)methyl]-1H-imidazol-2-yl}pyridine-2-carbonitrile | 2-cyanopyridin-6-yl | propyl | Cl | | 377.1/378.1 |

TABLE 2-continued

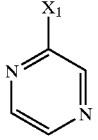

| Cmp. # | Name | W | R5 | R3 | 1H NMR | Mass Spec (Cald./Obs. M + 1) |
|---|---|---|---|---|---|---|
| 103 | 6-chloro-3-propyl-2-[(2-pyrazin-2-yl-1H-imidazol-1-yl)methyl]imidazo[1,2-b]pyridazine | 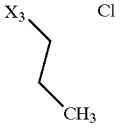 | 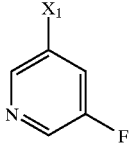 | Cl | | 353.1/354.2 |
| 104 | 6-chloro-2-{[2-(5-fluoropyridin-3-yl)-1H-imidazol-1-yl]methyl}-3-propylimidazo[1,2-b]pyridazine | 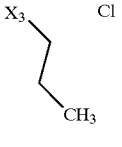 | 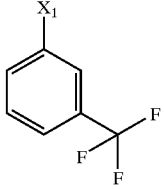 | Cl | | 370.1/371.2 |
| 105 | 6-chloro-3-propyl-2-({2-(3-(trifluoromethyl)phenyl]-1H-imidazol-1-yl}methyl)imidazo[1,2-b]pyridazine | 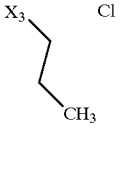 | 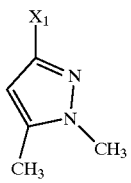 | Cl | | 419.1/420.2 |
| 106 | 6-chloro-2-{[2-(1,5-dimethyl-1H-pyrazol-3-yl)-1H-imidazol-1-yl]methyl}-3-propylimidazo[1,2-b]pyridazine | 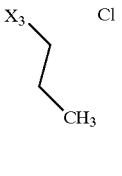 | 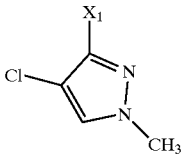 | Cl | | 369.2/370.2 |
| 107 | 6-chloro-2-{[2-(4-chloro-1-methyl-1H-pyrazol-3-yl)-1H-imidazol-1-yl]methyl}-3-propylimidazo[1,2-b]pyridazine | 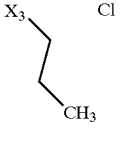 | 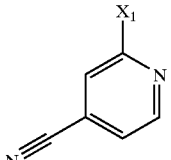 | Cl | | 389.1/390.3 |
| 108 | 2-{1-[(6-chloro-3-propylimidazo[1,2-b]pyridazin-2-yl)methyl]-1H-imidazol-2-yl}isonicotinonitrile | 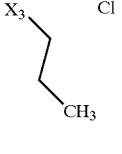 | 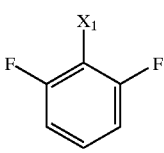 | Cl | | 377.1/378.3 |
| 109 | 6-chloro-2-{[2-(2,6-difluorophenyl)-1H-imidazol-1-yl]methyl}-3-propylimidazo[1,2-b]pyridazine | 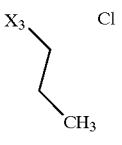 | | Cl | | 387.1/388.2 |

TABLE 2-continued

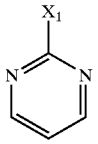

| Cmp. # | Name | W | R5 | R3 | 1H NMR | Mass Spec (Cald./Obs. M + 1) |
|---|---|---|---|---|---|---|
| 110 | 6-chloro-3-propyl-2-[(2-pyrimidin-2-yl-1H-imidazol-1-yl)methyl]imidazo[1,2-b]pyridazine |  | 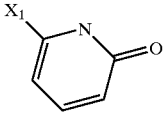 | Cl | | 353.1/354.5 |
| 111 | 6-{1-[(6-chloro-3-methylimidazo[1,2-b]pyridazin-2-yl)methyl]-1H-imidazol-2-yl}pyridin-2(1H)-one |  | 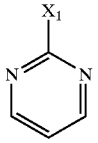 | Cl | | 340.8/341 |
| 112 | 6-chloro-3-methyl-2-[(2-pyrimidin-2-yl-1H-imidazol-1-yl)methyl]imidazo[1,2-b]pyridazine |  | 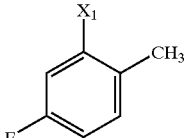 | Cl | | 325.1/326.1 |
| 113 | 6-chloro-2-{[2-(5-fluoro-2-methylphenyl)-1H-imidazol-1-yl]methyl}-3-propylimidazo[1,2-b]pyridazine | 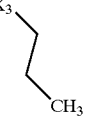 | 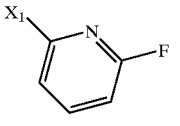 | Cl | | 383.1/384.2 |
| 114 | 6-chloro-2-{[2-(6-fluoropyridin-2-yl)-1H-imidazol-1-yl]methyl}imidazo[1,2-b]pyridazine | 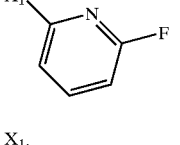 | H | Cl | | 328.7/329.0 |
| 115 | 3,6-dichloro-2-{[2-(6-fluoropyridin-2-yl)-1H-imidazol-1-yl]methyl}imidazo[1,2-b]pyridazine | 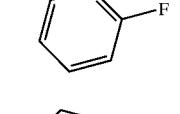 | Cl | Cl | | 362.0/363.1 |
| 116 | 2-{[2-(6-fluoropyridin-2-yl)-1H-imidazol-1-yl]methyl}-3,6-dimethylimidazo[1,2-b]pyridazine |  | 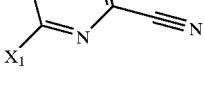 | CH₃ | | 322.3/323.2 |
| 117 | 6-{1-[(3,6-dimethylimidazo[1,2-b]pyridazin-2-yl)methyl]-1H-imidazol-2-yl}pyridine-2-carbonitrile |  | 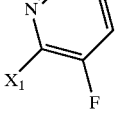 | CH₃ | free base in CDCl3: 8.47, d(1H); 7.88, t(1H); 7.75, d(1H); 7.62, d(1H); 7.31, d(1H); 7.18, d(1H); 6.85, d(1H); 6.08, s(2H); 2.58, s(3H); 2.60, s(3H) | |
| 118 | 2-{[2-(3-fluoropyridin-2-yl)-1H-imidazol-1-yl]methyl}-3,6-dimethylimidazo[1,2-b]pyridazine |  | | CH₃ | | 322.3/323.0 |

TABLE 2-continued

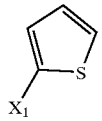

| Cmp. # | Name | W | R5 | R3 | 1H NMR | Mass Spec (Cald./Obs. M + 1) |
|---|---|---|---|---|---|---|
| 119 | 6-chloro-3-methyl-2-[(2-thien-2-yl-1H-imidazol-1-yl)methyl]imidazo[1,2-b]pyridazine |  | $X_3$—$CH_3$ | Cl | | 329.0/330.1 |
| 120 | 6-chloro-3-ethyl-2-{[2-(3-fluoropyridin-2-yl)-1H-imidazol-1-yl]methyl}imidazo[1,2-b]pyridazine | 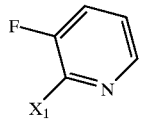 | $X_3$—$CH_2CH_3$ | Cl | | 356.7/357.7 |
| 121 | 3-ethyl-2-{[2-(3-fluoropyridin-2-yl)-1H-imidazol-1-yl]methyl}imidazo[1,2-b]pyridazine |  | $X_3$—$CH_2CH_3$ | H | | 322.1/323.2 |
| 122 | 2-{[2-(6-chloropyridin-2-yl)-1H-imidazol-1-yl]methyl}-3-ethyl-N,N-dimethylimidazo[1,2-b]pyridazin-6-amine | 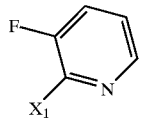 | $X_3$—$CH_2CH_3$ | $X_5$—$N(CH_3)_2$ | | 381.2/382.2 |
| 123 | 2-{[2-(6-chloropyridin-2-yl)-1H-imidazol-1-yl]methyl}-3-ethyl-N-methylimidazo[1,2-]pyridazin-6-amine |  | $X_3$—$CH_2CH_3$ | $CH_3$—NH—$X_5$ | | 367.1/368.2 |
| 124 | 6-chloro-3-ethyl-2-[(2-pyrimidin-2-yl-1H-imidazol-1-yl)methyl]imidazo[1,2-b]pyridazine | 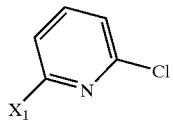 | $X_3$—$CH_2CH_3$ | Cl | | 339.7/340.4 |
| 125 | 6-chloro-3-ethyl-2-{[2-(1,3-thiazol-2-yl)-1H-imidazol-1-yl]methyl}imidazo[1,2-b]pyridazine |  | $X_3$—$CH_2CH_3$ | Cl | | 344.8/345.9 |
| 126 | 3-ethyl-2-{[2-(3-fluoropyridin-2-yl)-1H-imidazol-1-yl]methyl}-6-methoxyimidazo[1,2-b]pyridazine | 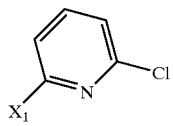 | $X_3$—$CH_2CH_3$ | —$OCH_3$ | | 352.1/353.2 |
| 127 | 3-ethyl-2-{[2-(3-fluoropyridin-2-yl)-1H-imidazol-1-yl]methyl}-6-(3-hydroxy-3-methylbutoxy)imidazo[1,2-b]pyridazine |  | $X_3$—$CH_2CH_3$ | 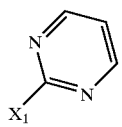 | free base in CDCl3: 7.88, d(1H); 7.73, d(1H); 7.38, d(1H); 721, d(1H); 7.08, d(1H); 6.62, d(1H); 6.02, s(2H); 4.51, t(2H); 2.93, q(2H); 2.21, t(2H); 1.35, s(6H); 1.05, t(3H) | |

TABLE 3

| Cmp # | Name | W | R5 | R2 | 1H NMR | Mass Spec (Cal./Obs. M + 1) |
|---|---|---|---|---|---|---|
| 128 | 3-chloro-2-{[2-(6-fluoro-pyridin-2-yl)-1H-imidazol-1-yl]methyl}-7-methoxy-imidazo[1,2-c]pyrimidine | 6-fluoropyridin-2-yl | Cl | OCH$_3$ | free base in CDCl3: 8.62, s(1H); 8.08, d(1H); 7.82, dd(1H); 7.22, d(1H); 7.19, d(1H); 6.85, dd (1H); 6.68, s(1H); 6.05, s(2H); 3.95, s(3H) | |
| 129 | 3-chloro-2-{[2-(2,5-difluorophenyl)-1H-imidazol-1-yl]methyl}-7-methoxy-imidazo[1,2-c]pyrimidine | 2,5-difluorophenyl | Cl | OCH$_3$ | free base in CDCl3: 8.62, s(1H); 7.32, m(1H); 7.20, s(1H); 7.18, s(1H); 7.12, m(2H); 6.65, s (2H); 3.92, s(3H) | |
| 130 | 3-chloro-2-{[2-(3-fluorophenyl)-1H-imidazol-1-yl]methyl}-7-methoxy-imidazo[1,2-c]pyrimidine | 3-fluorophenyl | Cl | OCH$_3$ | | 357.7/358.6 |

TABLE 4

| Cmp. # | Name | W | R5 | R3 | 1H NMR | Mass Spec (Cal./Obs. M + 1) |
|---|---|---|---|---|---|---|
| 131 | 3-chloro-2-{[2-(6-fluoro-pyridin-2-yl)-1H-imidazol-1-yl]methyl}imidazo[1,2-a]pyrazine | 6-fluoropyridin-2-yl | Cl | H | free base in CDCl3: 9.01, s(1H); 8.09, dd(1H); 7.97, m(2H); 7.82, q, (1H); 7.24, s(1H); 7.18, s(1H); 6.83, dd(1H); 6.17, s (2H) | |
| 132 | 3-bromo-2-{[2-(6-fluoro-pyridin-2-yl)-1H-imidazol-1-yl]methyl}imidazo[1,2-a]pyrazine | 6-fluoropyridin-2-yl | Br | H | free base in CDCl3: 9.0, s(1H); 8.10, dd(1H); 8.00, s(2H); 7.85, q(1H); 7.20, s(1H), 7.15, s(1H); 6.85, dd(1H); 6.15, s(2H) | |
| 133 | 3-bromo-2-{[2-(3-fluoro-pyridin-2-yl)-1H-imidazol-1-yl]methyl}imidazo[1,2-a]pyrazine | 3-fluoropyridin-2-yl | Br | H | free base in CDCl3: 9.0, s(1H); 8.45, dd(1H); 8.00, m(2H); 7.55, t(1H); 7.40–7.2, m(3H); 5.95, s(2H) | |
| 134 | 6-bromo-3-chloro-2-{[2-(6-fluoro-pyridin-2-yl)-1H-imidazol-1-yl]methyl}imidazo[1,2-a]pyrazine | 6-fluoropyridin-2-yl | Cl | Br | free base in CDCl3: 8.70, s(1H); 8.15, m(1H); 8.05, m(1H); 7.25, s(1H); s(1H); 7.20, s(1H), 6.85, dd(1H); 6.15, s(2H) | |

TABLE 4-continued

| Cmp. # | Name | W | R5 | R3 | 1H NMR | Mass Spec (Cal./Obs. M + 1) |
|---|---|---|---|---|---|---|
| 135 | 3-chloro-2-{[2-(6-fluoro-pyridin-2-yl)-1H-imidazol-1-yl]methyl}-6-methyl-imidazo[1,2-a]pyrazine | 6-fluoropyridin-2-yl | $X_2$\Cl | $X_3$\CH$_3$ | free base in CDCl3: 8.80, s(1H); 8.15, s(1H); 7.85, m(2H); 7.35, s(1H); 7.20, s(1H), 6.85, dd (1H); 6.10, s(2H) | |
| 136 | 3-chloro-2-{[2-(6-fluoro-pyridin-2-yl)-1H-imidazol-1-yl]methyl}-6-methoxy-imidazo[1,2-a]pyrazine | 6-fluoropyridin-2-yl | $X_2$\Cl | CH$_3$–O–$X_3$ | free base in CDCl3: 8.85, s(1H); 8.05, s(1H); 7.80, d(1H); 7.65, t (1H); 7.15, s(1H); 7.10, s(1H), 6.70, d(1H); 6.30, s(2H); 3.85, s (3H) | |
| 137 | 3-chloro-6-methoxy-2-{[2-(6-methoxy-pyridin-2-yl)-1H-imidazol-1-yl]methyl}imidazo[1,2-a]pyrazine | 6-methoxypyridin-2-yl | $X_2$\Cl | CH$_3$–O–$X_3$ | free base in CDCl3: 8.75, s(1H); 7.80, d(1H); 7.70, t(1H); 7.45, s (1H); 7.15, s(1H); 7.10, s(1H); 6.70, d(1H); 6.30, s(2H); 3.95, s (3H); 3.85, s(3H) | |
| 138 | 3-chloro-6-pyrrolidin-1-yl-2-{[2-(6-pyrrolidin-1-ylpyridin-2-yl)-1H-imidazol-1-yl]methyl}imidazo[1,2-a]pyrazine | 6-pyrrolidin-1-ylpyridin-2-yl | $X_2$\Cl | pyrrolidin-1-yl–$X_3$ | | 448.2/449.0 |
| 139 | 2-{[2-(6-fluoropyridin-2-yl)-1H-imidazol-1-yl]methyl}-3,6-dimethylimidazo[1,2-a]pyrazine | 6-fluoropyridin-2-yl | $X_2$\CH$_3$ | $X_3$\CH$_3$ | | 322.35/ 323.3 |
| 140 | 6-bromo-3-chloro-2-{[2-(1,3-thiazol-2-yl)-1H-imidazol-1-yl]methyl}imidazo[1,3-a]pyrazine | 1,3-thiazol-2-yl | $X_2$\Cl | Br–$X_3$ | free base in CDCl3: 8.83, d(1H); 8.04, d(1H); 7.80, d(1H); 7.31, d(1H); 7.18, s(1H); 7.15, s (1H); 6.16, s(2H) | |
| 141 | 3-bromo-2-{[2-(6-methoxy-pyridin-2-yl)-1H-imidazol-1-yl]methyl}imidazo[1,2-a]pyrazine | 6-methoxypyridin-2-yl | $X_2$\Br | H | free base in CDCl3: 9.00, s(1H); 8.00, m(2H); 7.80, d(1H); 7.65, t (1H); 7.15, s(1H), 7.10, s(1H); 6.70, d(1H); 6.30, s(2H); 3.90, s (3H) | |
| 142 | 3-chloro-2-{[2-(3-fluoro-phenyl)-1H-imidazol-1-yl]methyl}-6-methyl-imidazo[1,2-a]pyrazine | 3-fluorophenyl | $X_2$\Cl | $X_3$\CH$_3$ | free base in CDCl3: 8.99, d(1H); 7.79, s(1H); 7.53, m(3H); 7.15, m(3H); 5.38, s(2H); 2.58, s (3H) | |

TABLE 5

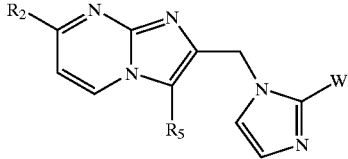

| Cmp. # | Name | W | R5 | R2 | 1H NMR | Mass Spec (Cald./Obsd. M + 1) |
|---|---|---|---|---|---|---|
| 143 | 2-{[2-(6-fluoropyridin-2-yl)-1H-imidazol-1-yl]methyl}-3-propyl-imidazo[1,2-a]pyrimidine | 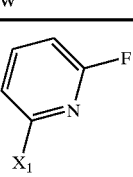 | 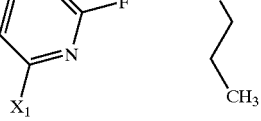 | H | free base in CDCl3: 8.52, dd (1H); 8.20, dd(1H); 8.13, dd(1H); 7.88, dd(1H); 7.52, d(1H); 7.12, dd(1H); 7.01, m(2H); 6.16, s(1H); 2.99, t(2H); 1.50, p(2H), 0.87, t(3H) | 336.12/337.30 |
| 144 | 3-{1-[(3-propylimidazo[1,2-a]pyrimidin-2-yl)methyl]-1H-imidazol-2-yl}benzonitrile | 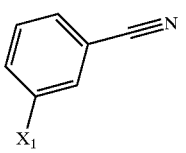 |  | H | free base in CDCl3: 8.57(dd (1H); 8.22, dd(1H); 8.12, d(1H); 8.07, s(1H); 7.72, d(1H); 7.60, t(1H); 7.21, d(1H); 7.14, d(1H); 6.93, dd(1H); 5.36, s(2H); 2.68, t(2H); 1.49, p(2H), 0.89, t(3H) | 342.16/343.20 |
| 145 | 3-bromo-2-{[2-(6-fluoropyridin-2-yl)-1H-imidazol-1-yl]methyl}imidazo[1,2-a]pyrimidine | 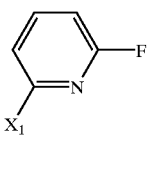 |  | H | free base in CDCl3: 8.56, dd (1H); 8.35, dd(1H); 8.09, dd(1H); 7.83, dd(1H); 7.32, s(1H); 7.14, s(1H); 6.99, dd(1H); 6.85, dd(1H); 6.18, s(2H) | 372.01/375.00 |
| 146 | 3-ethyl-2-{[2-(6-fluoropyridin-2-yl)-1H-imidazol-1-yl]methyl}imidazo[1,2-a]pyrimidine | 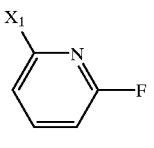 | 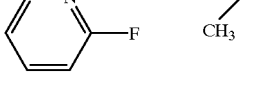 | H | di HCl salt in d6 DMSO: 9.23, dd(1H); 8.87, dd(1H); 8.36, m (2H); 7.93, d(1H); 7.86, d (1H); 7.50, m(2H); 6.19, s(2H); 3.10, q(2H); 1.10, t(3H) | 322.13/323.30 |
| 147 | 3-ethyl-2-{[2-(3-fluorophenyl)-1H-imidazol-1-yl]methyl}imidazo[1,2-a]pyrimidine | 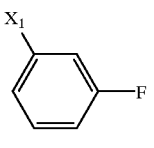 | 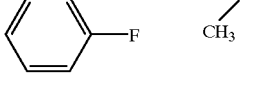 | H | di HCl salt in d6 DMSO: 9.12, bd(1H); 8.77, bs(1H); 7.93, bm(2H); 7.71, m(4H); 7.56, m (2H); 7.37, bs(1H); 5.71, s(2H); 2.97, q(2H); 1.10, t(3H) | 321.14/322.30 |
| 148 | 3-{1-[(3-ethylimidazo[1,2-a]pyrimidin-2-yl)methyl]-1H-imidazol-2-yl}benzonitrile | 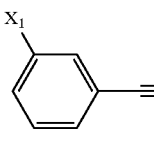 | 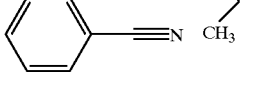 | H | di HCl salt in d6 DMSO: 9.11, d(1H); 8.76, d(1H); 8.49, d(1H); 8.24, d(1H); 8.18, d(1H); 7.92, s(1H); 7.87, t(1H); 7.79, s(1H); 7.36(t(1H); 5.71, s(2H), 2.99, q(2H) 1.11, t(3H) | 328.14/329.30 |
| 149 | 2-{[2-(6-chloropyridin-2-yl)-1H-imidazol-1-yl]methyl}-3-ethyl-imidazo[1,2-a]pyrimidine | 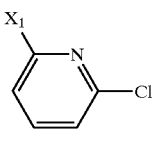 | 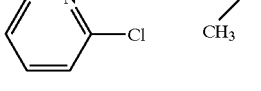 | H | di HCl salt in d6 DMSO: 9.18, d(1H); 8.83, s(1H); 8.36, d(1H); 8.19, t(1H); 7.92, s(1H); 7.81, s(1H); 7.78, d(1H); 7.44, bs(1H); 6.18, s(2H); 3.07, q(2H), 1.08, t(3H) | 338.10/339.20 |
| 150 | 2-{[2-(3-chlorophenyl)-1H-imidazol-1-yl]methyl}-3-ethyl-imidazo[1,2-a]pyrimidine | 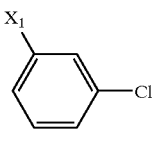 | 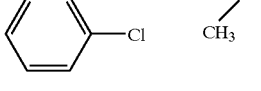 | H | di HCl salt in d6 DMSO: 9.08, dd(1H); 8.74, dd(1H); 8.07, dd(1H); 7.90, m(2H); 7.80, m(2H); 7.67, t(1H); 7.34, dd(1H); 5.68, s(2H); 2.98, q(2H); 1.11, t(3H) | 337.11/338.20 |

TABLE 5-continued

| Cmp. # | Name | W | R5 | R2 | 1H NMR | Mass Spec (Cald./Obsd.) M + 1 |
|---|---|---|---|---|---|---|
| 151 | 3-ethyl-2-{[2-[2-(trifluoromethyl)phenyl]-1H-imidazol-1-yl}methyl)imidazo[1,2-a]pyrimidine | X1-phenyl-2-CF3 | X2-CH2CH3 | H | di HCl salt in d6 DMSO; 9.05, dd(1H); 8.75, dd(1H); 8.02, m (6H); 7.34, dd(1H); 5.44, s (2H); 2.74, q(2H); 0.99, t(3H) | 371.14/372.20 |
| 152 | 2-{[2-(2-chlorophenyl)-1H-imidazol-1-yl]methyl}-3-ethyl-imidazo[1,2-a]pyrimidine | X1-phenyl-2-Cl | X2-CH2CH3 | H | di HCl salt in d6 DMSO: 9.05, dd(1H); 8.75, dd(1H); 7.96, m (3H); 7.77, d(2H); 7.60, m (1H); 7.34, dd(1H); 5.52, s(2H); 2.74, q(2H); 1.00, t(3H) | 337.11/338.20 |
| 153 | 3-ethyl-2-{[2-(2-fluorophenyl)-1H-imidazol-1-yl]methyl}imidazo[1,2-a]pyrimidine | X1-phenyl-2-F | X2-CH2CH3 | H | di HCl salt in d6 DMSO: 9.20, d(1H); 8.85, dd(1H); 7.90, m(4H); 7.51, m(3H); 5.66, s(2H); 2.90, q(2H); 1.06, t(3H) | 321.14/322.20 |
| 154 | 3-ethyl-2-{[2-(3-fluoropyridin-2-yl)-1H-imidazol-1-yl]methyl}imidazo[1,2-a]pyrimidine | X1-(3-F-pyridin-2-yl) | X2-CH2CH3 | H | di HCl salt in d6 DMSO: 9.16, d(1H); 8.81, d(1H); 8.72, d(1H); 8.15, t(1H); 8.01, s(1H); 7.93, s(1H); 7.84, m(1H); 7.42, dd(1H); 5.66, s(2H); 2.90, q(2H), 1.06, t(3H) | 322.13/323.20 |
| 155 | 3-ethyl-2-{[2-(2-fluoropyridin-4-yl)-1H-imidazol-1-yl]methyl}imidazo[1,2-a]pyrimidine | X1-(2-F-pyridin-4-yl) | X2-CH2CH3 | H | di HCl salt in d6 DMSO: 9.10, d(1H); 8.75, d(1H); 8.55, d(1H); 7.90, m(3H); 7.79, s(1H); 7.35, dd(1H); 5.76, s(2H); 3.01, q(2H); 1.12, t(3H) | 322.13/323.30 |
| 156 | 6-{1-[(3-ethylimidazo[1,2-a]pyrimidin-2-yl)methyl]-1H-imidazol-2-yl}pyridine-2-carbonitrile | X1-(6-CN-pyridin-2-yl) | X2-CH2CH3 | H | di HCl salt in d6 DMSO: 9.23, d(1H); 8.87, d(1H); 8.60, d(1H); 8.34, dd(1H); 8.23, d(1H); 7.87, s(1H); 7.73, s(1H); 7.50, bs(1H); 6.17, s(2H); 3.08, q(2H), 1.10, t(3H) | 329.14/330.20 |
| 157 | 3-ethyl-2-({2-[5-(trifluoromethyl)pyridin-2-yl]-1H-imidazol-1-yl}methyl)imidazo[1,2-a]pyrimidine | X1-(5-CF3-pyridin-2-yl) | X2-CH2CH3 | H | di HCl salt in d6 DMSO: 9.21, m(2H); 8.88, d(1H); 8.56, bs(2H); 7.93, s(1H); 7.78, s(1H); 7.50, m(1H); 6.25, s(2H); 3.06, q(2H); 1.08, t(3H) | 372.13/373.20 |

TABLE 5-continued

| Cmp. # | Name | W | R5 | R2 | 1H NMR | Mass Spec (Cald./Obsd. M + 1) |
|---|---|---|---|---|---|---|
| 158 | 3-bromo-2-{[2-(3-fluoro-phenyl)-1H-imidazol-1-yl]methyl}imidazo[1,2-a]pyrimidine | 3-fluorophenyl (X₁) | Br (X₂) | H | di HCl salt in d6 DMSO: 8.79, dd(1H); 8.63, dd(1H); 7.91, s(2H); 7.80, dd(1H); 7.68, m(2H); 7.54, m(1H); 7.23, dd(1H); 5.61, s(2H); | 371.02/374.00 |
| 159 | 3-bromo-2-({2-[6-(trifluoromethyl)pyridin-2-yl]-1H-imidazol-1-yl}methyl)imidazo[1,2-a]pyrimidine | 6-(trifluoromethyl)pyridin-2-yl (X₁) | Br (X₂) | H | di HCl salt in d6 DMSO: 8.79, dd(1H); 8.62, d(1H); 8.57, dd(1H); 8.41, t(1H); 8.10, d(1H); 7.98, d(1H); 7.93, s(1H); 7.21, dd(1H); 6.10, s(2H) | 422.01/425.10 |
| 160 | 3-bromo-2-{[2-(1,5-dimethyl-1H-pyrazol-3-yl)-1H-imidazol-1-yl]methyl}imidazo[1,2-a]pyrimidine | 1,5-dimethyl-1H-pyrazol-3-yl (X₁) | Br (X₂) | H | di HCl salt in d6 DMSO: 8.82, dd(1H); 8.61, dd(1H); 7.85, s(1H); 7.79, s(1H); 7.23, dd(1H); 7.00, s(1H); 3.86, s(3H); 6.77, 2.32, s(2H); | 371.05/374.10 |
| 161 | 3-bromo-2-{[2-[3-(trifluoromethyl)phenyl]-1H-imidazol-1-yl]methyl}imidazo[1,2-a]pyrimidine | 3-(trifluoromethyl)phenyl (X₁) | Br (X₂) | H | di HCl salt in CD3OD: 8.89, dd(1H); 8.82, dd(1H); 8.16, d(1H); 8.06, d(1H); 7.89, d(1H); 7.86, d(1H); 7.81, d(1H); 7.42, dd(1H); 5.74, s(2H) | 421.01/424.30 |
| 162 | 3-bromo-2-{[2-(4-methoxyphenyl)-1H-imidazol-1-yl]methyl}imidazo[1,2-a]pyrimidine | 4-methoxyphenyl (X₁) | Br (X₂) | H | di HCl salt in CD3OD: 8.90, dd(1H); 8.81, dd(1H); 7.71, m(4H); 7.41, dd(1H); 7.21, d(2H); 5.71, s(2H); 3.90, s(3H) | 383.04/386.00 |
| 163 | 3-bromo-2-({2-[3-fluoro-5-(trifluoromethyl)phenyl]-1H-imidazol-1-yl}methyl)imidazo[1,2-a]pyrimidine | 3-fluoro-5-(trifluoromethyl)phenyl (X₁) | Br (X₂) | H | di HCl salt in CD3OD: 8.86, dd(1H); 8.78, dd(1H); 8.05, d(1H); 8.03, s(1H); 7.91, d(1H); 7.88, d(1H); 7.82, s(1H); 7.40, dd(1H); 5.73, s(2H) | 439.01/441.90 |
| 164 | 3-bromo-2-{[2-(3,5-difluorophenyl)-1H-imidazol-1-yl]methyl}imidazo[1,2-a]pyrimidine | 3,5-difluorophenyl (X₁) | Br (X₂) | H | di HCl salt in CD3OD: 8.89, dd(1H); 8.80, dd(1H); 7.84, d(1H); 7.79, d(1H); 7.59, m(2H); 7.40, m(2H); 5.74, s(2H) | 389.01/392.00 |

TABLE 5-continued

| Cmp. # | Name | W | R5 | R2 | 1H NMR | Mass Spec (Cald./Obsd. M + 1) |
|---|---|---|---|---|---|---|
| 165 | 3-bromo-2-{[2-(2-methyl-1,3-thiazol-4-yl)-4-1H-imidazol-1-yl]methyl}imidazo[1,2-a]pyrimidine | 2-methyl-1,3-thiazol-4-yl (X1) | Br (X2) | H | di HCl salt in CD3OD: 8.99, dd(1H); 8.87, dd(1H); 8.41, s(1H); 7.81, s(1H); 7.75, s(1H); 7.51, dd(1H); 6.23, s(2H); 2.80, s(3H); | 373.99/377.00 |
| 166 | 2-{[2-(3-fluorophenyl)-1H-imidazol-1-yl]methyl}-3-methylimidazo[1,2-a]pyrimidine | 3-fluorophenyl (X1) | CH3 (X2) | H | di HCl salt in d6 DMSO: 8.95, dd(1H); 8.71, dd(1H); 7.91m, m(2H); 7.88, d(1H); 7.85, d(1H); 7.73, m(2H); 7.56, m(1H); 7.32, m(1H); 5.66, s(2H); 2.41, s(3H) | 307.12/308.20 |
| 167 | 6-{1-[(3-methylimidazo[1,2-a]pyrimidin-2-yl)methyl]-1H-imidazol-2-yl}pyridine-2-carbonitrile | 6-cyanopyridin-2-yl (X1) | CH3 (X2) | H | di HCl salt in d6 DMSO: 9.07, dd(1H); 8.83, dd(1H); 8.53, d(1H); 8.31, dd(1H); 8.18, dd(1H); 7.82, s(1H); 7.65, s(1H); 7.46, m(1H); 6.11, s(2H); 2.46, s(3H) | 315.12/316.20 |
| 168 | 6-{1-[(3-bromoimidazo[1,2-a]pyrimidin-2-yl)methyl]-1H-imidazol-2-yl}pyridine-2-carbonitrile | 6-cyanopyridin-2-yl (X1) | Br (X2) | H | di HCl salt in d6 DMSO: 8.80, dd(1H); 8.59, dd(1H); 8.51, d(1H); 8.32, dd(1H); 8.20, d(1H); 7.97, d(1H); 7.85, s(1H); 7.20, d(1H); 6.04, s(2H) | 379.02/382.0 |
| 169 | 2-{[2-(6-fluoropyridin-2-yl)-1H-imidazol-1-yl]methyl}-3-methylimidazo[1,2-a]pyrimidine | 6-fluoropyridin-2-yl (X1) | CH3 (X2) | H | di HCl salt in d6 DMSO: 9.07, dd(1H); 8.82, dd(1H); 8.32, m(2H); 7.90, s(1H); 7.82, s(1H); 7.46, m(2H); 6.13, s(2H); 2.54, s(3H) | 308.12/309.20 |
| 170 | 3-ethyl-2-{[2-6-(trifluoromethyl)pyridin-2-yl]-1H-imidazol-1-yl}methyl)imidazo[1,2-a]pyrimidine | 6-(trifluoromethyl)pyridin-2-yl (X1) | CH2CH3 (X2) | H | di HCl salt in d6 DMSO: 9.10, d(1H); 8.77, bs(1H); 8.53, d(1H); 8.37, t(1H); 8.07, d(1H); 7.76, s(1H); 7.64, s(1H); 7.36, m(1H); 6.17, s(2H); 2.92, q(2H), 1.01, t(3H) | 372.13/373.00 |
| 171 | 3-ethyl-2-{[2-(5-methyl-isoxazol-3-yl)-1H-imidazol-1-yl]methyl}imidazo[1,2-a]pyrimidine | 5-methylisoxazol-3-yl (X1) | CH2CH3 (X2) | H | di HCl salt in d6 DMSO: 9.21, dd(1H); 8.86, dd(1H); 7.86, d(1H); 7.76, s(1H); 7.48, dd(1H); 7.16, s(1H); 6.01, s(2H); 3.06, q(3H); 2.54, s(3H), 1.11, t(3H) | 308.14/309.11 |
| 172 | 3-ethyl-2-{[2-(1,3-thiazol-2-yl)-1H-imidazol-1-yl]methyl}imidazo[1,2-a]pyrimidine | 1,3-thiazol-2-yl (X1) | CH2CH3 (X2) | H | di HCl salt in d6 DMSO: 9.28, dd(1H); 8.96, dd(1H); 8.05, d(1H); 7.95, d(1H); 7.74, s(1H); 7.59, dd(1H); 7.33, s(1H); 6.20, s(2H); 3.04, q(2H), 1.02, t(3H) | 310.10/311.08 |

TABLE 5-continued

| Cmp. # | Name | W | R5 | R2 | 1H NMR | Mass Spec (Cald./Obsd. M + 1) |
|---|---|---|---|---|---|---|
| 173 | 2-{[2-(2,3-difluorophenyl)-1H-imidazol-1-yl]methyl}-3-ethyl-imidazo[1,2-a]pyrimidine | 2,3-difluorophenyl (X₁) | CH₂CH₃ (X₂) | H | di HCl salt in d6 DMSO: 9.01, dd(1H); 8.76, bs(1H); 7.95, s(1H); 7.88, s(1H); 7.79, m(2H); 7.51, dd(1H); 7.36, dd(1H); 5.64, s(2H); 2.92, q(2H), 1.01, t(3H) | 339.13/340.10 |
| 174 | 2-{[2-(3,4-difluorophenyl)-1H-imidazol-1-yl]methyl}-3-ethyl-imidazo[1,2-a]pyrimidine | 3,4-difluorophenyl (X₁) | CH₂CH₃ (X₂) | H | di HCl salt in d6 DMSO: 9.13, dd(1H); 8.77, dd(1H); 8.21, t(1H); 7.88, s(1H); 7.79, m(2H); 7.75, s(1H); 7.38, dd(1H); 5.68, s(2H); 2.98, q(2H), 1.06, t(3H) | 339.13/340.08 |
| 175 | 3-ethyl-2-{[2-(6-fluoropyridin-2-yl)-1H-imidazol-1-yl]methyl}-7-methyl-imidazo[1,2-a]pyrimidine | 6-fluoropyridin-2-yl (X₁) | CH₂CH₃ (X₂) | CH₃ (X₃) | di HCl salt in d6 DMSO: 9.17, dd(1H); 8.33m, m(2H); 7.87, s(1H); 7.78, s(1H); 7.52, d(1H); 7.46(d, 1H); 6.16, s(2H); 3.02, q(2H); 2.65, s(3H); 1.06, t(3H) | 336.15/337.07 |
| 176 | 3-ethyl-2-{[2-(5-fluoro-2-methylphenyl)-1H-imidazol-1-yl]methyl}imidazo[1,2-a]pyrimidine | 5-fluoro-2-methylphenyl (X₁) | CH₂CH₃ (X₂) | H | di HCl salt in d6 DMSO: 9.03, dd(1H); 8.71, dd(1H); 7.89, s(1H); 7.73, d(1H); 7.44, d(2H); 7.29, dd(1H); 5.50, s(2H); 2.81, q(2H); 2.10, s(3H), 1.04, t(3H) | 335.15/336.08 |
| 177 | 2-[{2-(3-chloro-2,5-difluorophenyl)-1H-imidazol-1-yl]methyl}-3-ethyl-7-(trifluoromethyl)imidazo[1,2-a]pyrimidine | 3-chloro-2,5-difluorophenyl (X₁) | CH₂CH₃ (X₂) | CF₃ (X₃) | di HCl salt in d6 DMSO: 8.58, dd(1H); 8.26, bs(1H); 8.31, bs(2H); 7.97, bs(1H); 7.88, bs(1H); 7.47, m(1H); 6.13, s(2H); 3.06, q(2H); 1.19, t(3H) | |
| 178 | 2-{[2-(2,5-difluorophenyl)-1H-imidazol-1-yl]methyl}-3-ethyl-imidazo[1,2-a]pyrimidine | 2,5-difluorophenyl (X₁) | CH₂CH₃ (X₂) | H | di HCl salt in d6 DMSO: 9.10, d(1H); 8.76, d(1H); 7.98, dd(1H); 7.94, s(1H); 7.87, s(2H); 7.62, m(2H); 7.35, dd(1H); 5.64, s(2H); 2.93, q(2H); 1.07, t(3H) | 339.13/340.10 |
| 179 | 2-{[2-(3-chloro-2,5-difluorophenyl)-1H-imidazol-1-yl]methyl}-3-ethylimidazo[1,2-a]pyrimidine | 3-chloro-2,5-difluorophenyl (X₁) | CH₂CH₃ (X₂) | H | di HCl salt in d6 DMSO: 9.02, d(1H); 8.70, dd(1H); 8.03, dd(1H); 7.96, s(1H); 7.91, s(1H); 7.47, t(1H); 7.29, dd(1H); 5.60, s(2H); 2.89, q(2H); 1.03, t(3H) | 373.09/374.20 |

TABLE 5-continued

| Cmp. # | Name | W | R5 | R2 | 1H NMR | Mass Spec (Cald./Obsd. M + 1) |
|---|---|---|---|---|---|---|
| 180 | 3-{1-[(3-ethylimidazo[1,2-a]pyrimidin-2-yl)methyl]-1H-imidazol-2-yl}-4-fluorobenzonitrile | $X_1$, F, CN (phenyl) | H | $X_2$ = $CH_3$ (ethyl via $CH_2$) | di HCl salt in d6 DMSO: 9.00, dd(1H); 8.68, bs(1H); 8.54, dd(1H); 8.27, m(1H); 7.91, s(1H); 7.88, s(1H); 7.75, t(1H); 7.26, dd(1H); 5.62, s(2H); 2.91, q(2H), 1.06, t(3H) | 346.13/347.20 |

TABLE 6

| Cmp. # | Name | W | R5 | R3 | R1 | R | 1H NMR | Mass Spec (Cald./Obsd. M + 1) |
|---|---|---|---|---|---|---|---|---|
| 181 | 3-Propyl-2-[2-(3-fluoro-phenyl)-imidazol-1-ylmethyl]-5-methyl-pyrazolo[1,5-a]pyrimidine | 3-F-phenyl ($X_1$) | $X_2$-propyl ($CH_2CH_2CH_3$) | $X_3$, $CH_3$ | H | H | | 349.2/350.2 |
| 182 | 3-Propyl-2-[2-(2-fluoro-phenyl)-imidazol-1-ylmethyl]-5-methyl-pyrazolo[1,5-a]pyrimidine | 2-F-phenyl ($X_1$) | $X_2$-propyl | $X_3$, $CH_3$ | H | H | | 349.2/350.2 |
| 183 | 3-Propyl-2-[2-(4-fluoro-phenyl)-imidazol-1-ylmethyl]-5-methyl-pyrazolo[1,5-a]pyrimidine | 4-F-phenyl ($X_1$) | $X_2$-propyl | $X_3$, $CH_3$ | H | H | | 349.2/350.2 |
| 184 | 3-Propyl-2-[2-(2,5-difluoro-phenyl)-imidazol-1-ylmethyl]-5-methyl-pyrazolo[1,5-a]pyrimidine | 2,5-diF-phenyl ($X_1$) | $X_2$-propyl | $X_3$, $CH_3$ | H | H | | 367.2/368.2 |

TABLE 6-continued

| Cmp. # | Name | W | R5 | R3 | R1 | R | 1H NMR | Mass Spec (Cald./ Obsd. M + 1) |
|---|---|---|---|---|---|---|---|---|
| 185 | 3-Propyl-2-[2-(3-chloro-4-fluorophenyl)-imidazol-1-ylmethyl]-5-methyl-pyrazolo[1,5-a]pyrimidine | 2-F, 3-Cl phenyl (X1=F para) | $X_2$ = propyl | $X_3$ = CH$_3$ | H | H | | 383.1/384.2 |
| 186 | 3-Propyl-2-[2-(3-chlorophenyl)-imidazol-1-ylmethyl]-5-methyl-pyrazolo[1,5-a]pyrimidine | 3-Cl phenyl | $X_2$ = propyl | $X_3$ = CH$_3$ | H | H | | 365.1/366.2 |
| 187 | 3-Propyl-2-[2-(3-fluorophenyl)-4-methyl-imidazol-1-ylmethyl]-5-methyl-pyrazolo[1,5-a]pyrimidine | 3-F phenyl | $X_2$ = propyl | $X_3$ = CH$_3$ | H | CH$_3$ | | 363.2/364.2 |
| 188 | 3-Propyl-2-[2-(2,5-difluorophenyl)-4-methyl-imidazol-1-ylmethyl]-5-methyl-pyrazolo[1,5-a]pyrimidine | 2,5-diF phenyl | $X_2$ = propyl | $X_3$ = CH$_3$ | H | CH$_3$ | | 381.2/382.2 |
| 189 | 3-Ethyl-2-[2-(3-fluorophenyl)-imidazol-1-ylmethyl]-5-methyl-7-methoxy-pyrazolo[1,5-a]pyrimidine | 3-F phenyl | $X_2$ = ethyl | $X_3$ = CH$_3$ | OCH$_3$ | H | | 365.2/366.2 |
| 190 | 3-Ethyl-2-[2-(3-chlorophenyl)-imidazol-1-ylmethyl]-5-methyl-7-methoxy-pyrazolo[1,5-a]pyrimidine | 3-Cl phenyl | $X_2$ = ethyl | $X_3$ = CH$_3$ | OCH$_3$ | H | | 381.1/382.2 |
| 191 | 3-Ethyl-2-[2-(2,5-difluorophenyl)-imidazol-1-ylmethyl]-5-methyl-7-methoxy-pyrazolo[1,5-a]pyrimidine | 2,5-diF phenyl | $X_2$ = ethyl | $X_3$ = CH$_3$ | OCH$_3$ | H | | 383.2/384.2 |

TABLE 6-continued

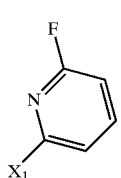

| Cmp. # | Name | W | R5 | R3 | R1 | R | 1H NMR | Mass Spec (Cald./ Obsd. M + 1) |
|---|---|---|---|---|---|---|---|---|
| 192 | 3-Ethyl-2-[2-(6-fluoro-pyridin-2-yl)-imidazol-1-ylmethyl]-5-methyl-pyrazolo[1,5-a]pyrimidine | 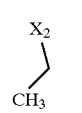 |  | 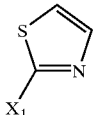 | H | H | Free base in CDCl3: 8.36, d (1H); 8.10, dd(1H); 7.81, q (1H); 7.48(d, 1H); 7.33(d, 1H); 7.25(s, 1H), 7.12, s(1H); 7.07, s (1H); 6.84, dd(1H); 6.57, d (1H); 6.12, s(2H); 2.71, q (2H); 2.56, s(3H); 1.04, t(3H) | |

TABLE 7

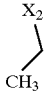

| Cmp. # | Name | W | R₅ | R₃ | MS | NMR |
|---|---|---|---|---|---|---|
| 193 | 4-(3-ethyl-2-{[2-(1,3-thiazol-2-yl)-1H-imidazol-1-yl]methyl}imidazo[1,2-a]pyridin-6-yl)-2-methylbutan-2-ol | 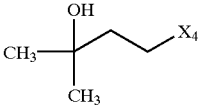 | 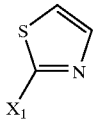 | 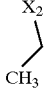 | | 1HNMR(CDCl3, 400MHz)-7.86(d, 1H), 7.67(s, 1H), 7.48(d, 1H), 7.33(d, 1H), 7.25(s, 1H), 7.01(m, 2H), 6.06(s, 2H), 2.90(q, 2H), 2.68(m, 2H), 1.78(m, 2H), 1.31(s, 6H), 1.00(t, 3H). |
| 194 | (3E)-4-(3-ethyl-2-{[2-(1,3-thiazol-2-yl)-1H-imidazol-1-yl]methyl}imidazo[1,2-a]pyrimidin-6-yl)-2-methylbut-3-en-2-ol | 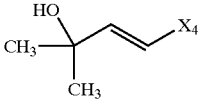 | 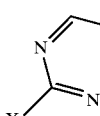 | 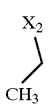 | | 1HNMR(CDCl3, 400MHz)-7.86(d, 1H), 7.77(s, 1H), 7.50(d, 1H), 7.33(d, 1H), 7.25(s, 1H), 7.05(s, 1H), 6.55(d, 1H), 6.06(s, 2H), 2.90(q, 2H), 1.31(s, 3H), 1.05(s, 3H), 1.00(t, 3H). |
| 195 | 3-ethyl-2-[(2-pyrimidin-2-yl-1H-imidazol-1-yl)methyl]-6-(1,3-thiazol-2-yl)imidazol[1,2-a]pyridine | 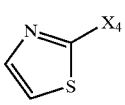 | 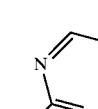 | 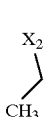 | 382.2 | free base in CDCl3: 8.85, d(2H); 8.64, m(1H); 7.82, d(1H); 7.62, d (2H); 7.40, d(1H); 7.25, m (3H); 6.13, s(2H); 3.95, q(2H); 1.10, t,(3H) |
| 196 | 3-ethyl-6-pyrimidin-2-yl-2-[(2-pyrimidin-2-yl-1H-imidazol-1-yl)methyl]imidazol[1,2-a]pyrimidine | 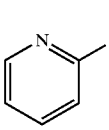 | | | | |

TABLE 7-continued

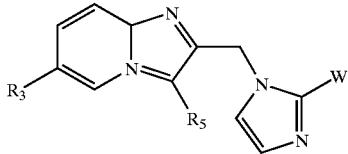

| Cmp. # | Name | W | R₅ | R₃ | MS | NMR |
|---|---|---|---|---|---|---|
| 197 | 1-{3-ethyl-2-[(2-pyrimidin-2-yl-1H-imidazol-1-yl)methyl]imidazo[1,2-a]pyridin-6-yl}ethanone | 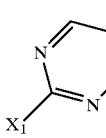 | 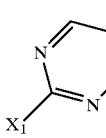 | 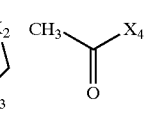 | M + I (339.2) | free base in CDCl3: 8.84, d(2H);8.56, m(1H); 7.67, dd(1H); 7.60, dd(1H); 7.23, m(3H); 6.14, s(2H); 2.92, q(2H); 2.63, s(3H); 1.05, 1(3H) |
| 198 | 6-chloro-3-ethyl-2-[(2-pyrimidin-2-7l-1H-imidazol-1-yl)methyl]imidazo[1,2-a]pyridine | 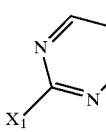 | 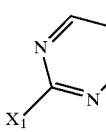 | 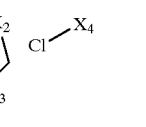 | M + I (339.2) | 1HNMR(CDCl3, 400MHz)- 8383(d, 2H), 7.89(d, 1H), 7.49(d, 1H), 7.23(m, 3H), 7.13(d, 1H), 6.10 (s, 2H), 2.83(q, 2H), 1.03(t, 3H). |
| 199 | 3-ethyl-6-[3-methoxypropyl]-2-[(2-pyrimidin-2-yl-1H-imidazol-1-yl)methyl]imidazo[1,2-a]pyridine | 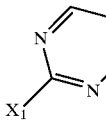 | 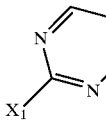 | 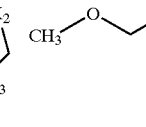 | | free base in CDCl3: 8.84, d(2H), 7.89(d, 1H), 7.46, d(1H); 7.22, m(3H); 7.03, dd(1H); 6.14, s (2H); 3.40, t(2H); 3.32 s(3H); 2.81, q(2H); 2.65, t (2H); 1.85, m(2H); 1.02, t(3H). |
| 200 | 3-ethyl-6-fluoro-2-[(2-pyrimidin-2-yl-1H-imidazol-1-yl)methyl]imidazo[1,2-a]pyridine | 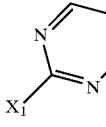 | 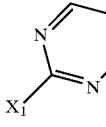 | 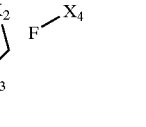 | | free base in CDCl3: 8.84, d(2H); 7.80, m(1H); 7.52, dd(1H); 7.24, m(3H); 7.05, m(1H); 6.14, s (2H); 2.92, q(2H); 0.95, t(3H) |

TABLE 7-continued

| Cmp. # | Name | W | R₅ | R₃ | MS | NMR |
|---|---|---|---|---|---|---|
| 201 | 6-bromo-3-ethyl-2-[(2-pyrimidin-2-yl-1H-imidazol-1-yl)methyl]imidazo[1,2-a]pyridine | 2-pyrimidinyl | X₂–CH₃ | CH₂–Br, X₄ | | free base in CDCl3: 8.84, d(2H); 8.00, m(1H); 7.48, d(1H); 7.24, m(4H); 6.14, s(2H); 2.92, q(2H); 1.05, t(3H) |
| 202 | 3-ethyl-6-fluoro-2-{[2-(1,3-thiazol-2-yl)-1H-imidazol-1-yl]methyl}imidazo[1,2-a]pyridine | 1,3-thiazol-2-yl | X₂–CH₃ | F, X₄ | | free base in CDCl3: 7.86, d(1H); 7.80, m(1H); 7.55, m(1H); 7.35, d(1H); 7.26, s(1H); 7.09, m(2H); 6.14, s(2H); 2.95 q(2H); 1.05, t(3H) |
| 203 | 3-ethyl-6-(2-methylphenyl)-2-[(2-pyrimidin-2-yl-1H-imidazol-1-yl)methyl]imidazo[1,2-a]pyridine | 2-pyrimidinyl | X₂–CH₃ | 2-methylphenyl, X₄ | | free base in CDCl3: 8.84, d(2H); 7.87, m(1H); 7.58, d(1H); 7.24, m(8H); 6.14, s(2H); 2.85, q(2H); 2.29 s (3H); 1.05, t(3H) |
| 204 | 3-ethyl-6-(2-methoxyphenyl)-2-[(2-pyrimidin-2-yl-1H-imidazol-1-yl)methyl]imidazo[1,2-a]pyridine | 2-pyrimidinyl | X₂–CH₃ | 2-methoxyphenyl, X₄ | | free base in CDCl3: 8.84, d(2H); 8.02, m(1H); 7.58, dd(1H); 7.33, m(3H); 7.20, m(3H); 7.00, m(2H); 6.12, s(2H); 3.83, s(3H); 2.85, q(2H); 1.05, t(3H) |
| 205 | 3-ethyl-2-[(2-pyrimidin-2-yl-1H-imidazol-1-yl)methyl]-6-[2-(trifluoromethyl)phenyl]imidazo[1,2-a]pyridine | 2-pyrimidinyl | X₂–CH₃ | 2-(trifluoromethyl)phenyl, X₄ | 449.42 | free base in CDCl3: 8.84, d(2H); 7.83, s(1H); 7.75, dd(1H); 7.53, m(3H); 7.38, d(1H); 7.30, s(1H); 7.22, m(2H); 7.13, dd(1H); 6.15, s(2H); 2.85, q(2H); 1.00, t(3H) |

TABLE 8

| Cmp. # | Name | W | R₅ | R₃ | 1H NMR | MS calc/obs. |
|---|---|---|---|---|---|---|
| 206 | '1-(3-ethyl-2-{[(2-(1,3-thiazol-2-yl)-1H-imidazol-1-yl]methyl}imidazo[1,2-b]pyridazin-6-yl)ethanone | 1,3-thiazol-2-yl | X₂–CH₃ | C(O)–CH₃, X₃ | free base in CDCl3: 7.95(d, 1H); 7.88 (d, 1H), 7.69(d, 1H), 7.35(d, 1H), 7.26(d, 1H), 7.13(d, 1H), 6.18(s, 2H), 3.09(q, 2H), 2.75(s, 3H), 1.18(t, 3H) | |

TABLE 8-continued

| Cmp. # | Name | W | R₅ | R₃ | 1H NMR | MS calc/obs. |
|---|---|---|---|---|---|---|
| 207 | 4-(3-ethyl-2-{[2-(1,3-thiazol-2-yl)-1H-imidazol-1-yl]methyl}imidazo[1,2-b]pyridazin-6-yl)-2-methylbutan-2-ol | thiazol-2-yl (X₁) | CH₂CH₃ (X₂) | HO-C(CH₃)₂-CH₂CH₂-X₃ | free base in CDCl3: 7.87(d, 1H); 7.79 (d, 1H); 7.35(d, 1H); 7.22(d, 1H); 7.08(d, 1H); 6.91(d, 1H); 6.09(s, 2H); 2.92–3.02(m, 4H); 1.93(t, 2H); 1.28(s, 6H); 1.07(t, 3H) | |
| 208 | 1-{3-ethyl-2-[(2-pyrimidin-2-yl-1H-imidazol-1-yl)methyl]imidazo[1,2-b]pyridazin-6-yl}ethanone | pyrimidin-2-yl (X₁) | CH₂CH₃ (X₂) | O=C(CH₃)-X₃ | free base in CDCl3: 8.87(d, 2H); 7.95 (d, 1H); 7.71(d, 1H); 7.22–7.29(m, 3H); 6.20(s, 2H); 3.02(q, 2H); 2.72 (s, 3H); 1.15(t, 3H) | |
| 209 | 3-ethyl-2-[(2-pyrimidin-2-yl-1H-imidazol-1-yl)methyl]imidazo[1,2-b]pyridazine | pyrimidin-2-yl (X₁) | CH₂CH₃ (X₂) | H | free base in CDCl3: 8.83(d, 2H); 8.30 (d, 1H); 7.86(d, 1H); 7.20–7.28(m, 3H); 6.98(dd, 1H); 6.13(s, 2H); 2.97 (q, 2H); 1.06(t, 3H) | |
| 210 | 3-ethyl-2-[(2-pyrimidin-2-yl-1H-imidazol-1-yl)methyl]-6-(1,3-thiazol-2-yl)imidazo[1,2-b]pyridazine | pyrimidin-2-yl (X₁) | CH₂CH₃ (X₂) | thiazol-2-yl-X₃ | free base in CD3OD: 9.07(d, 2H); 8.31(d, 1H); 8.20(d, 1H); 8.07(d, 1H); 7.93(d, 1H); 7.89(d, 1H); 7.84 (d, 1H); 7.69(t, 1H); 6.50(s, 2H); 3.32 (q, 2H); 1.42(t, 3H) | |
| 211 | 3-ethyl-2-[(2-pyrimidin-2-yl-1H-imidazol-1-yl)methyl]-6-(trifluoromethyl)imidazo[1,2-b]pyridazine | pyrimidin-2-yl (X₁) | CH₂CH₃ (X₂) | CF₃-X₃ | | 373.1/374.1 |
| 212 | 3-ethyl-6-(2-isopropoxyethoxy)-2-[(2-pyrimidin-2-yl-1H-imidazol-1-yl)methyl]imidazo[1,2-b]pyridazine | pyrimidin-2-yl (X₁) | CH₂CH₃ (X₂) | (CH₃)₂CH-O-CH₂CH₂-O-X₃ | 1H NMR(CDCl3): 8.84(d, 1H), 7.77 (d, 1H), 7.22(m, 3H), 6.68(d, 1H), 6.07(s, 2H), 4.44(t, 2H), 3.80(t, 2H), 3.67(m, 1H), 2.85(2H), 1.90(d, 6H), 1.06(t, 3H). | 407.4/408.4 |
| 213 | 3-ethyl-2-[(2-pyrimidin-2-yl-1H-imidazol-1-yl)methyl]-6-(tetrahydro-2H-pyran-4-yloxy)imidazo[1,2-b]pyridazine | pyrimidin-2-yl (X₁) | CH₂CH₃ (X₂) | tetrahydropyran-4-yl-O-X₃ | 1H NMR(CDCl3): 8.85(d, 2H), 7.72 (d, 1H), 7.23(m, 3H), 6.64(d, 1H), 6.08(s, 2H), 5.16(m, 1H), 3.97(m, 2H), 3.62(m, 2H), 2.84(q, 2H), 2.09 (m, 2H), 1.86(m, 2H), 1.07(t, 3H) | 405.4/406.4 |
| 214 | 6-(4-chloro-2-methylphenoxy)-3-ethyl-2-[(2-pyrimidin-2-yl-1H-imidazol-1-yl)methyl]imidazo[1,2-b]pyridazine | pyrimidin-2-yl (X₁) | CH₂CH₃ (X₂) | 4-Cl-2-CH₃-C₆H₃-O-X₃ | 1H NMr(CDCl3): 8.81(d, 2H), 7.83(d, 1H), 7.23(m, 5H), 7.02(d, 1H), 6.83 (d, 1H), 6.07(s, 2H), 2.68(q, 2H), 2.18(s, 3H), 0.88(t, 3H). | 445.2/446.2 |
| 215 | 3-ethyl-2-[(2-pyrimidin-2-yl-1H-imidazol-1-yl)methyl]-6-{[4-(trifluoromethyl)benzyl]oxy}imidazo[1,2-b]pyridazine | pyrimidin-2-yl (X₁) | CH₂CH₃ (X₂) | 4-CF₃-C₆H₄-CH₂-O-X₃ | | 479.4/480.4 |

TABLE 8-continued

| Cmp. # | Name | W | R5 | R3 | 1H NMR | MS calc/ obs. |
|---|---|---|---|---|---|---|
| 216 | 3-ethyl-2-[(2-pyri-midin-2-yl-1H-imi-dazol-1-yl)methyl]-6-(tetra-hydrofuran-3-yloxy)imi-dazo[1,2-b]pyridazine | | CH3 | X3 (tetrahydrofuran-3-yloxy) | | 391.4/ 392.4 |
| 217 | 3-ethyl-2-[(2-pyri-midin-2-yl-1H-imi-dazol-1-yl)methyl]-6-[4-(tri-fluoromethoxy-phen-oxy]imidazo[1,2-b]py-ridazine | | CH3 | X3 (4-trifluoromethoxyphenoxy) | free base in CDCl3: 8.82(d, 2H); 7.86 (d, 1H); 7.20–7.30(m, 7H); 6.82(d, 1H); 6.07(s, 2H); 2.74(q, 2H); 0.93(t, 3H) | |

Example 15
Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 16
Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 17
Binding Assay

The high affinity and high selectivity of preferred compounds of the invention for the benzodiazepine site of the $GABA_A$ receptor can be confirmed using the binding assay described by Thomas and Tallman (*J. Bio. Chem.* 1981; 156:9838–9842, and *J. Neurosci.* 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted. The resulting pellet may be stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations contain 100 μl of tissue homogenate, 100 μl of radioligand, (0.5 nM $^{3}H$-Ro15-1788 [$^{3}H$-Flumazenil], specific activity 80 Ci/mmol), and test compound or control (see below), and are brought to a total volume of 500 μl with Buffer A. Incubations are carried for 30 minutes at 4° C. and then rapidly filtered through Whatman GFB filters to separate free and bound ligand. Filters are washed twice with fresh Buffer A and counted in a liquid scintillation counter. Nonspecific binding (control) is determined by displacement of $^{3}H$ Ro15-1788 with 10 μM Diazepam (Research Biochemicals International, Natick, Mass.). Data are collected in triplicate, averaged, and percent inhibition of total specific binding (Total Specific Binding=Total−Nonspecific) is calculated for each compound.

A competition binding curve may obtained with up to 11 points spanning the compound concentration range from $10^{-12}M$ to $10^{-5}M$ obtained per curve by the method described above for determining percent inhibition. $K_i$ values are calculated according the Cheng-Prussof equation. Preferred compounds of the invention exhibit $K_i$ values of less than 100 nM and more preferred compounds of the invention exhibit $K_i$ values of less than 10 nM.

Example 18

Electrophysiology

The following assay can be used to determine if a compound of the invention acts as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. Xenopus Laevis oocytes are enzymatically isolated and injected with non-polyadenylated cRNA mixed in a ratio of 4:1:4 for $\alpha$, $\beta$ and $\gamma$ subunits, respectively. Of the nine combinations of $\alpha$, $\beta$ and $\gamma$ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. NM 021911; human $\beta_3$, GENBANK accession no. M82919 and accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 $\mu$M GABA is applied.

Compounds are evaluated against a GABA concentration that evokes <10% of the maximal evokable GABA current (e.g. 1 $\mu$M–9 $\mu$M). Each oocyte is exposed to increasing concentrations of a compound being evaluated (test compound) in order to evaluate a concentration/effect relationship. Test compound efficacy is calculated as a percent-change in current amplitude: $100*((I_c/I)-1)$, where Ic is the GABA evoked current amplitude observed in the presence of test compound and I is the GABA evoked current amplitude observed in the absence of the test compound.

Specificity of a test compound for the benzodiazepine site is determined following completion of a concentration/effect curve. After washing the oocyte sufficiently to remove previously applied test compound, the oocyte is exposed to GABA+1 $\mu$M Ro15-1788, followed by exposure to GABA+1 $\mu$M Ro15-1788+test compound. Percent change due to addition of compound is calculated as described above. Any percent change observed in the presence of RO15-1788 is subtracted from the percent changes in current amplitude observed in the absence of 1 $\mu$M RO15-1788. These net values are used for the calculation of average efficacy and $EC_{50}$ values by standard methods. To evaluate average efficacy and $EC_{50}$ values, the concentration/effect data are averaged across cells and fit to the logistic equation.

It is to be understood that the foregoing describes preferred embodiments of the present invention and that modifications may be made therein without departing from the scope of the present invention as set forth in the following claims.

What is claimed is:
1. A compound of the formula:

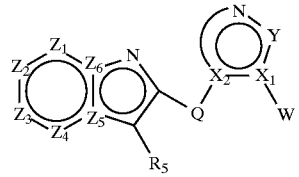

or a pharmaceutically acceptable salt thereof, wherein:

$Z_1$ is $CR_1$;

$Z_2$ is $CR_2$;

$Z_3$ is $CR_3$;

$Z_4$ is $CR_4$;

$Z_5$ is nitrogen;

$Z_6$ is carbon;

$R_1$, $R_2$, $R_3$, and $R_4$ are independently selected from:

(i) hydrogen, halogen, hydroxy, nitro, cyano, amino, haloalkyl, and haloalkoxy;

(ii) alkyl, alkoxy, cycloalkyl, alkenyl, alkynyl, (cycloalkyl)alkyl, —NH($R_{10}$), —N($R_{10}$)'($R_{11}$'), hydroxyalkyl, aminoalkyl, ($R_{10}$)NHalkyl, ($R_{10}$)($R_{11}$)Nalkyl, alkanoyl, alkoxycarbonyl, alkylsulfonyl, ($C_1$–$C_6$)alkylsulfinyl, alkylthio, mono- and dialkylaminocarbonyl, heterocycloalkyl, aryl, and heteroaryl, each of which is unsubstituted or substituted with 1, 2, 3, or 4 substituents independently selected from $R_{20}$;

(iii) groups of the formula:

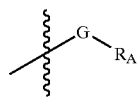

wherein G is alkyl, —O—, —C(=O)—, or —CH$_2$—C (=O)—, and $R_A$ is cycloalkyl, heterocycloalkyl, aryl, or heteroaryl, each of which is unsubstituted or substituted with 1, 2, 3, or 4 of $R_{20}$;

(iv) groups of the formula:

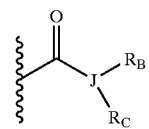

wherein J is N, CH, or C-alkyl, and $R_B$ and $R_C$ are each independently selected from the group consisting of hydrogen, alkyl, alkenyl, alkynyl, alkoxy, cycloalkyl, (cycloalkyl)alkyl, heterocycloalkyl, aryl, arylalkyl, alkanoyl, heteroaryl, and mono and dialkylaminoalkyl, each of which is unsubstituted or substituted with 1 or 2 substituents independently chosen from halogen, hydroxy, cyano, amino, nitro, alkoxy, haloalkoxy, alkyl and haloalkyl; or $R_B$ and $R_C$ and the atom to which they are attached form a 4- to 10-membered monocyclic or bicyclic ring, comprising:

a) 0, 1, 2 or 3 double bonds, and
b) 0, 1, 2 or 3 of oxo, O, S, SO, $SO_2$, or N—$R_D$, wherein $R_D$ is (1)hydrogen; or (2) $Ar_1$, alkyl, cycloalkyl, heterocycloalkyl, or $Ar_1$alkyl; wherein $Ar_1$ is aryl or heteroaryl, each of which is unsubstituted or substituted with 1 or 2 substituents independently chosen from halogen, hydroxy, cyano, amino, nitro, alkoxy, and alkyl; and (v) —OC(=O)$R_E$, —C(=O)$NH_2$, —C(=O)$NHR_E$, —C(=O)$NR_ER_F$, —S(O)$_nR_E$, —S(O)$_nNH_2$, —S(O)$_nNHR_E$, —S(O)$_nNR_ER_F$, —C(=$NR_E$)$R_F$, —HC=N—OH, —HC=N(alkoxy), —HC=N(alkyl), —NHS(O)$_nR_E$, and —$NR_ES(O)_nR_F$, wherein n is 0, 1 or 2;

$R_E$ and $R_F$ are independently selected at each occurrence from alkyl, cycloalkyl, heterocycloalkyl, alkoxy, mono- and dialkylamino, aryl, and heteroaryl, each of which is unsubstituted or substituted with 1, 2, or 3 substituents independently selected from $R_{30}$;

$R_5$ represents:

(i) hydrogen, halogen, cyano, or haloalkyl;

(ii) alkyl, cycloalkyl, (cycloalkyl)alkyl, each of which comprises from 0 to 3 double bonds and/or from 0 to 3 triple bonds, and is unsubstituted or substituted with 1, 2, or 3 substituents independently selected from $R_{30}$; or (iii) aryl, arylalkyl, heteroaryl, or heteroarylalkyl, each of which is unsubstituted or substituted with 1, 2, or 3 substituents independently selected from the group consisting of haloalkyl, amino, —NH($R_{10}$), —N($R_{10}$)($R_{11}$), carboxamido, ($R_{10}$)NHcarbonyl, ($R_{10}$)($R_{11}$)Ncarbonyl, halogen, hydroxy, nitro, cyano, amino, alkyl, alkoxy, alkoxy substituted with amino or mono- or dialkylamino, cycloalkyl, cycloalkylalkyl, cycloalkylalkoxy, cycloalkyloxy, heterocycloalkyl, alkenyl, alkynyl, haloalkyl, haloalkoxy, aminoalkyl, and mono- and dialkylaminoalkyl;

$R_{10}$ and $R_{11}$ are independently selected from the group consisting of alkyl, alkenyl, alkynyl, alkoxy, cycloalkyl, cycloalkylalkyl, aryl, arylalkyl, alkanoyl, and mono and dialkylaminoalkyl;

$R_{10}'$ and $R_{11}'$ are independently selected from the group consisting of alkyl, alkenyl, alkynyl, alkoxy, cycloalkyl, cycloalkylalkyl, aryl, arylalkyl, alkanoyl, and mono and dialkylaminoalkyl;

Q represents —C($R_6$)($R_7$), —N(alkyl)- or oxygen, wherein $R_6$ and $R_7$ independently represent hydrogen, fluorine, or alkyl; with the proviso that Q is not oxygen when $X_2$ is nitrogen;

$R_{20}$ is independently selected at each occurrence from: halogen, hydroxy, nitro, cyano, amino, alky, alkoxy, alkoxy substituted with amino or mono- or dialkylamino, cycloalkyl, cycloalkylalkyl, cycloalkyloxy, alkenyl, alkynyl, haloalkyl, haloalkoxy, mono- and dialkylamino, aminoalkyl, and mono- and dial kylaminoalkyl;

$R_{30}$ is independently selected at each occurrence from: halogen, hydroxy, nitro, cyano, amino, alkyl, alkoxy; alkoxy substituted with amino or mono- or dialkylamino, cycloalkyl, cycloalkylalkyl, cycloalkylalkoxy, cycloalkyloxy, heterocycloalkyl, alkenyl, alkynyl, haloalkyl, haloalkoxy, mono- and dialkylamino, aminoalkyl, and mono- and dialkylaminoalkyl; and the group:

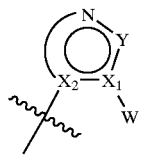

represents a 5 to 7 menibered heteroaryl group containing from 1 to 4 heteroatoms independently selected from nitrogen, sulfur, and oxygen, unsubstituted or substituted at each carbon atom by R, and unsubstituted or substituted at each nitrogen atom available for substitution by R', wherein R is independently chosen at each occurrence from halogen, amino, alkyl, alkenyl, alkynyl, alkoxy, cycloalkyl, (cycloalkyl)alkyl, haloalkyl, haloalkoxy, carboxamido, and 3- to 7-membered carbocyclic and heterocyclic rings, each of which is unsubstituted or substituted with one or more substituents independently selected from halogen, oxo, hydroxy, alkyl, and alkoxy;

R' is independently chosen at each occurrence from alkyl, cycloalkyl, cycloalkyl(alkyl), and 3- to 7-membered carbocyclic and heterocyclic rings, each of which unsubstituted or substituted with one or more substituents independently selected from halogen, oxo, hydroxy, alkyl, and alkoxy;

$X_1$ and $X_2$ independently represent nitrogen, carbon or CH;

Y is nitrogen, carbon, —CH—, —$CH_2$—, or absent; and

W represents aryl or heteroaryl, each of which is unsubstituted or substituted with from 0 to 4 groups independently selected from $R_{30}$, —C(=O)O$R_E$, —C(=O)$NR_E$, —C(O)$R_E$, —O$R_E$ and —S(O)$_mR_E$, wherein m is 0, 1, or 2.

2. A compound or salt according to claim 1, wherein $R_1$, $R_2$, $R_3$, and $R_4$ are independently selected from:

(i) hydrogen, halogen, hydroxy, nitro, cyano, amino, halo($C_1$–$C_6$)alkyl, and halo($C_1$–$C_6$)alkoxy, (ii) ($C_1$–$C_6$)alkyl, ($C_1$–$C_6$)alkoxy, ($C_3$–$C_8$)cycloalkyl, ($C_2$–$C_6$)alkenyl, ($C_2$–$C_6$)alkynyl, (($C_3$–$C_8$)cycloalkyl)($C_1$–$C_4$)alkyl, —NH($R_{10}'$), —N($R_{10}'$)($R_{11}'$), hydroxy($C_1$–$C_6$)alkyl, amino($C_1$–$C_6$)alkyl, ($R_{10}$)NH—, ($C_1$–$C_6$)alkyl, ($R_{10}$)($R_{11}$)N($C_1$–$C_6$)alkyl, ($C_1$–$C_6$)alkanoyl, ($C_1$–$C_6$)alkoxycarbonyl, ($C_1$–$C_6$)alkylsulfonyl, ($C_1$–$C_6$)alkylsulfinyl, ($C_1$–$C_6$)alkylthio, mono- and di($C_1$–$C_6$)alkylaminocarbonyl, and 3- to 8-membered heterocycloalkyl, aryl, and heteroaryl, each of which is unsubstituted or substituted with 1, 2, 3, or 4 substituents independently selected from $R_{20}$;

(iii) groups of the formula:

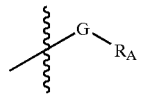

wherein G is ($C_1$–$C_6$)alkyl, —O—, —C(=O)—, or —$CH_2$—C(=O)—, and $R_A$ is 3- to 8-membered cycloalkyl, heterocycloalkyl, aryl, or heteroaryl, each of which is unsubstituted or substituted with 1, 2, 3, or 4 of $R_{20}$;

(iv) groups of the formula:

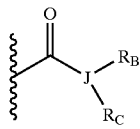

wherein J is N, CH, or C—($C_1$–$C_6$)alkyl and $R_B$ and $R_C$ are each independently selected from the group consisting of hydrogen, ($C_1$–$C_6$)alkyl, ($C_2$–$C_6$)alkenyl, ($C_2$–$C_6$)alkynyl, ($C_1$–$C_6$)alkoxy, ($C_3$–$C_8$)cycloalkyl, ($C_3$–$C_8$cycloalkyl) ($C_1$–$C_4$)alkyl, 3- to 8-membered heterocyoloalkyl, aryl, aryl($C_1$–$C_4$)alkyl, ($C_1$–$C_6$)alkanoyl, 3- to 8-membered heteroaryl, and mono and di($C_1$–$C_6$)alkylamino ($C_1$–$C_6$)alkyl, each of which is unsubstituted or substituted with 1 or 2 substituents independently chosen from halogen, hydroxy, cyano, amino, nitro, $C_1$–$C_6$alkoxy, halo ($C_1$–$C_6$)alkoxy, $C_1$–$C_6$alkyl and halo($C_1$–$C_6$)alkyl; or $R_B$ and $R_C$ and the atom to which they are attached form a 4- to 10-membered monocyclic or bicyclic ring, comprising:

a) 0, 1, 2 or 3 double bonds, and b) 0, 1, 2 or 3 of oxo, O, S, SO, $SO_2$, or N—$R_D$, wherein $R_D$ is (1) hydrogen; or (2) $Ar_1$, ($C_1$–$C_6$)alkyl, ($C_3$–$C_8$) cycloalkyl, 3- to 8-membered heterocycloalkyl, or $Ar_1$ ($C_1$–$C_6$)alkyl wherein $Ar_1$ is aryl or heteroaryl, each of which is unsubstituted or substituted with 1 or 2 substituents independently chosen from halogen, hydroxy, cyano, amino, nitro, $C_1$–$C_6$alkoxy, and $C_1$–$C_6$alkyl; and (v) —OC(=O)$R_E$, —C(=O)$NH_2$, —C(=O)$NHR_E$, —(C=O)$NR_ER_F$, —S(O)$_n$$R_E$, —S(O)$_n$$NH_2$, —S(O)$_n$$NHR_E$, —S(O)$_n$$NR_ER_F$, —C(=$NR_E$)$R_F$, —HC=N—OH, —HC=N($C_1$–$C_6$alkoxy), —HC=N ($C_1$–$C_6$alkyl), —NHS(O)$_n$$R_E$, and —$NR_E$S(O)$_n$$R_F$, wherein n is 0, 1 or 2, $R_E$ and $R_F$ are independently selected at each occurrence from ($C_1$–$C_6$)alkyl, ($C_3$–$C_8$)cycloalkyl, 3- to 8-membered heterocycloalkyl, ($C_1$–$C_6$)alkoxy, mono- and di($C_1$–$C_6$)alkylamino, aryl, and 3- to 8-membered heteroaryl, each of which is unsubstituted or substituted with 1, 2, or 3 substituents independently selected from $R_{30}$;

$R_5$ represents:

(i) hydrogen, halogen or cyano;

(ii) ($C_1$–$C_6$)alkyl, ($C_3$–$C_8$)cycloalkyl, ($C_3$–$C_8$cycloalkyl) ($C_1$–$C_4$)alkyl, or an analogue of the foregoing that comprises from 1 to 3 double bonds and/or from 1 to 3 triple bonds, each of which is unsubstituted or substituted with 1, 2, or 3 substituents independently selected from $R_{30}$; or (iii) 3- to 8-membered aryl, 3- to 8-membered aryl ($C_1$–$C_4$)alkyl, 3- to 8-membered heteroaryl, or 3- to 8-membered heteroaryl ($C_1$–$C_4$)alkyl, each of which is unsubstituted or substituted with 1, 2, or 3 substituents independently selected from the group consisting of halo($C_1$–$C_6$)alkyl, amino, —NH($R_{10}$), —N($R_{10}$)($R_{11}$), carboxamido, ($R_{10}$)NHcarbonyl, ($R_{10}$)($R_{11}$)Ncarbonyl, halogen, hydroxy, nitro, cyano, amino, ($C_1$–$C_6$)alkyl, ($C_1$–$C_6$)alkoxy, ($C_1$–$C_6$)alkoxy substituted with amino or mono- or di($C_1$–$C_6$)alkylamino, ($C_3$–$C_8$)cycloalkyl, ($C_3$–$C_8$)cycloalkyl ($C_1$–$C_4$)alkyl, ($C_3$–$C_8$)cycloalkyl ($C_1$–$C_4$)alkoxy, heterocyclo($C_1$–$C_4$)alkyl, ($C_2$–$C_6$) alkenyl, ($C_2$–$C_6$)alkynyl, halo($C_1$–$C_6$)alkyl, halo ($C_1$–$C_6$)alkoxy, amino($C_1$–$C_6$)alkyl, and mono- and di($C_1$–$C_6$)alkylamino($C_1$–$C_6$)alkyl;

$R_{10}$ and $R_{11}$ are independently selected from the group consisting of ($C_1$–$C_6$)alkyl, ($C_2$–$C_6$)alkenyl, ($C_1$–$C_6$) alkoxy, ($C_3$–$C_8$)cycloalkyl, ($C_3$–$C_8$)cycloalkylalkyl, aryl, aryl($C_1$–$C_6$)alkyl, ($C_1$–$C_6$)alkanoyl, and mono and di($C_1$–$C_6$)alkylaminoalkyl;

$R_{10}$' and $R_{11}$' are independently selected from the group consisting of ($C_1$–$C_6$)alkyl, ($C_2$–$C_6$)alkenyl, ($C_1$–$C_6$) alkoxy, ($C_3$–$C_8$)cycloalkyl, ($C_3$–$C_8$)cycloalkylalkyl, aryl, aryl($C_1$–$C_6$)alkyl, ($C_1$–$C_6$)alkanoyl, and mono and di($C_1$–$C_6$)alkylaminoalkyl;

$R_{20}$ is independently selected at each occurrence from the group consisting of halogen;, hydroxy, nitro, cyano, amino, ($C_1$–$C_6$)alkyl, ($C_1$–$C_6$)alkoxy, ($C_1$–$C_6$)alkoxy substituted with amino or mono- or di($C_1$–$C_6$) alkylamino, ($C_3$–$C_8$)cycloalkyl, ($C_3$–$C_8$)cycloalkyl ($C_1$–$C_4$)alkyl, ($C_3$–$C_8$)cycloalkyl($C_2$–$C_4$)alkoxy, ($C_2$–$C_6$)alkenyl, ($C_2$–$C_6$)alkynyl, halo($C_1$–$C_6$)alkyl, halo($C_1$–$C_6$)alkoxy, mono- and di($C_1$–$C_6$)alkylamino, amino($C_1$–$C_6$)alkyl, and mono- and di($C_1$–$C_6$) alkylamino($C_1$–$C_6$)alkyl;

$R_{30}$ is independently selected at each occurrence from halogen, hydroxy, nitro, cyano, amino, ($C_1$–$C_6$)alkyl, ($C_1$–$C_6$)alkoxy, ($C_1$–$C_6$)alkoxy substituted with amino or mono- or di($C_1$–$C_6$)alkylamino, ($C_3$–$C_8$)cycloalkyl, ($C_3$–$C_8$)cycloalkyl ($C_1$–$C_4$)alkyl, ($C_3$–$C_8$)cycloalkyl ($C_1$–$C_4$)alkoxy, 3- to 8-membered heterocycloalkyl, ($C_2$–$C_6$)alkenyl, ($C_2$–$C_6$)alkynyl, halo($C_1$–$C_6$)alkyl, halo($C_1$–$C_6$)alkoxy, mono- and di($C_1$–$C_6$)alkylamino, amino($C_1$–$C_6$)alkyl, and mono- and di($C_1$–$C_6$) alkylamino ($C_1$–$C_6$)alkyl;

Q represents C($R_6$)($R_7$), N($C_1$–$C_6$alkyl) or oxygen, wherein $R_6$ and $R_7$ independently represent hydrogen, fluorine, or $C_1$–$C_6$alkyl; with the proviso that Q is not oxygen when $X_2$ is nitrogen;

R is independently chosen at each occurrence from halogen, amino, $C_1$–$C_6$alkyl, ($C_2$–$C_6$)alkenyl, ($C_2$–$C_6$) alkynyl, $C_1$–$C_6$alkoxy, ($C_3$–$C_8$)cycloalkyl, ($C_3$–$C_8$cycloalkyl)($C_1$–$C_4$) alkyl, halo($C_1$–$C_6$)alkyl, haloalkoxy, carboxamido, and 3- to 7-membered carbocyclic and heterocyclic rings, each of which is unsubstituted substituted with from 1 to 4 substituents independently selected from halogen, oxo, hydroxy, $C_1$–$C_4$alkyl, and $C_1$–$C_4$alkoxy;

R' is independently chosen at each occurrence from $C_1$–$C_6$alkyl, $C_3$–$C_6$cycloalkyl, $C_3$–$C_8$cycloalkyl ($C_1$–$C_4$alkyl), and 3- to 7-membered carbocyclic and heterocyclic rings, each of which is unsubstituted or substituted with from 1 to 4 substituents independently selected from halogen, oxo, hydroxy, $C_1$–$C_4$alkyl, and $C_1$–$C_4$alkoxy; and W represents 3- to 8-membered aryl or heteroaryl, each of which is unsubstituted or substituted with from 1 to 4 groups independently selected from $R_{30}$, —C(=O) $OR_E$, —C(=O)$NR_E$, —C(O)$R_E$, —$OR_E$ and —S(O)$_m$ $R_E$, wherein m is 0, 1, or 2.

3. A compound or salt according to claim 2 of the formula:

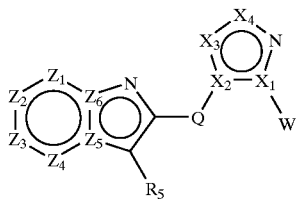

wherein $X_3$ and $X_4$ are independently selected from the group consisting of CH, CR, N, O, S, NH, and $N(C_1-C_6)$alkyl provided that at least one of $X_1$, $X_2$, $X_3$, and $X_4$ is CH or CR;

and wherein R is independently chosen at each occurrence from: halogen, amino, $(C_1-C_6)$alkyl, $(C_1-C_6)$alkoxy, $(C_3-C_8)$cycloalkyl, $(C_3-C_8)$cycloalkyl$(C_1-C_6)$alkyl, $(C_2-C_6)$alkenyl, $(C_2-C_6)$alkynyl, halo$(C_1-C_6)$alkyl, halo$(C_1-C_6)$ alkoxy, carboxamido, and 3- to 7-membered carbocyclic or heterocyclic rings, each of which is unsubstituted or substituted with from 1 to 4 substituents independently selected from halogen, oxo, hydroxy, $(C_1-C_4)$alkyl, and —O$(C_1-C_4$alkyl).

4. A compound or salt according to claim 3, wherein $X_2$ is carbon and Q is oxygen.

5. A compound or salt according to claim 3, wherein $X_2$ is carbon and Q is —NH—, or —N$(C_1-C_6$alkyl)-.

6. A compound or salt according to claim 3 of the formula:

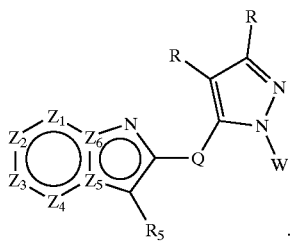

7. A compound or salt according to claim 6, wherein Q is $C(R_6)(R_7)$.

8. A compound or salt according to claim 7, wherein each R is independently selected from the group consisting of:

(i) hydrogen, halogen, $(C_1-C_6)$alkyl, $(C_3-C_8)$cycloalkyl, $(C_3-C_8)$cycloalkyl$(C_1-C_6)$alkyl, $(C_1-C_6)$alkoxy, halo $(C_1-C_6)$alkyl, halo$(C_1-C_6)$alkoxy; and (ii) phenyl and pyridyl, each of which is unsubstituted or substituted with from 1 to 3 substituents independently chosen from halogen, hydroxy, $C_1-C_4$alkyl, and $C_1-C_4$alkoxy;

$R_1$, $R_2$, $R_3$, and $R_4$ are independently selected from:

(i) hydrogen, halogen, hydroxy, nitro, cyano and amino;

(ii) $(C_1-C_6)$alkyl, $(C_1-C_6)$alkoxy, $(C_1-C_6)$alkanoyl, $(C_1-C_6)$alkyl ether, $(C_3-C_8)$cycloalkyl, $(C_3-C_8)$cycloalkyl$(C_1-C_6)$alkyl, $(C_2-C_6)$alkenyl, $(C_2-C_6)$alkynyl, 3- to 8-membered heterocycloalkyl, 3- to 8-membered heteroaryl, halo$(C_1-C_6)$alkyl, halo $(C_1-C_6)$alkoxy, mono and di$(C_1-C_6)$alkylamino, amino$(C_1-C_6)$alkyl, and mono- and di$(C_1-C_6)$ alkylamino$(C_1-C_6)$alkyl, each of which is unsubstituted or substituted with 1 or substituents independently selected from hydroxy, halogen, $(C_1-C_6)$alkyl, $(C_1-C_6)$alkoxy, halo$(C_1-C_6)$alkyl, halo$(C_1-C_6)$alkoxy; and (iii) groups of the formula

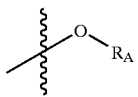

wherein $R_A$ is 5- to 7-membered cycloalkyl, heterocycloalkyl, aryl or heteroaryl, each of which is unsubstituted or substituted with 1 or 2 substituents independently selected from hydroxy, halogen, $(C_1-C_6)$alkyl, halo$(C_1-C_6)$alkyl, $(C_1-C_6)$alkoxy, halo$(C_1-C_6)$alkoxy;

$R_5$ represents hydrogen, halogen, $(C_1-C_6)$alkyl, $(C_3-C_8)$ cycloalkyl, $(C_3-C_8)$cycloalkyl$(C_1-C_6)$alkyl, phenyl, benzyl, thiophenyl, thiazolyl, pyridyl, imidazolyl, pyrazolyl, or pyrimidinyl;

$R_6$ and $R_7$ independently represent hydrogen, fluorine, or $C_1-C_6$ alkyl; and W represents phenyl, thienyl, thiazolyl, pyridyl, imidazolyl, pyrazolyl, isoxazolyl, or pyrimidinyl, each of which is unsubstituted or substituted with from 1 to 4 groups independently selected from $R_{30}$.

9. A compound or salt according to claim 3 of the formula:

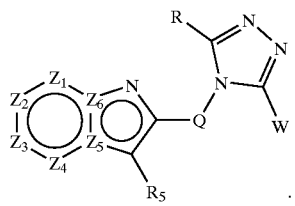

10. A compound or salt according to claim 9, wherein Q is $C(R_6)(R_7)$.

11. A compound or salt according to claim 3 of the formula:

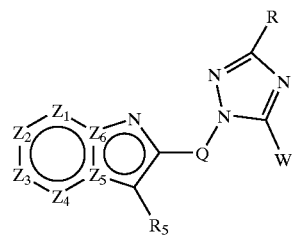

12. A compound or salt according to claim 3 of the formula:

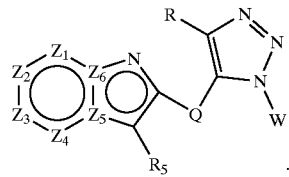

13. A compound or salt according to claim 3 of the formula:

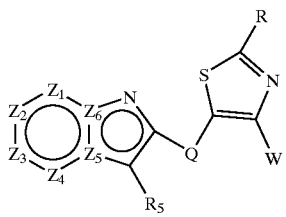

14. A compound or salt according to claim 13, wherein Q is $C(R_6)(R_7)$.

15. A compound or salt according to claim 2 of the formula:

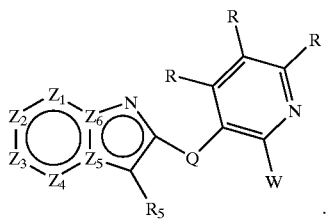

16. A compound or salt according to claim 15, wherein Q is $C(R_6)(R_7)$.

17. A compound or salt according to claim 3 of the formula:

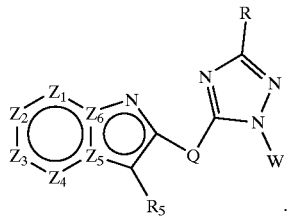

18. A compound or salt according to claim 3 of the formula

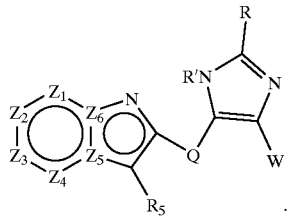

19. A compound or salt according to claim 3 of the formula:

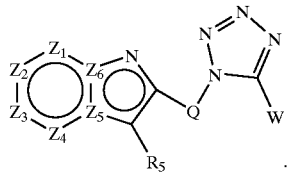

20. A compound or salt according to claim 3 of the formula:

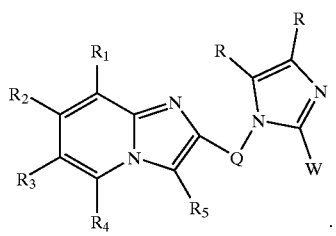

21. A compound or salt according to claim 20, wherein Q is $C(R_6)(R_7)$.

22. A compound or salt according to claim 21, wherein:

each R is independently selected from the group consisting of
(i) hydrogen, halogen, $(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_1-C_6)$alkyl and halo$(C_1-C_6)$alkoxy, and
(ii) phenyl and pyridyl, each of which is unsubstituted or substituted with from 1 to 3 substituents independently chosen from halogen, hydroxy, $C_1-C_4$alkyl, and $C_1-C_4$alkoxy;

$R_1$, $R_2$, $R_3$, and $R_4$ are independently selected from:
(i) hydrogen, halogen, hydroxy, nitro, cyano and amino;
(ii) $(C_1-C_6)$alkyl, $(C_1-C_6)$alkoxy, $(C_1-C_6)$alkanoyl, $(C_1-C_6)$alkyl ether, $(C_3-C_8)$cycloalkyl, $(C_3-C_8)$cycloalkyl$(C_1-C_6)$alkyl, $(C_2-C_6)$alkenyl, $(C_2-C_6)$alkynyl, 3- to 8-membered heterocycloalkyl, 3- to 8-membered heteroaryl, halo$(C_1-C_6)$alkyl, halo$(C_1-C_6)$alkoxy, mono and di$(C_1-C_6)$alkylamino, amino$(C_1-C_6)$alkyl, and mono- and di$(C_1-C_6)$alkylamino$(C_1-C_6)$alkyl, each of which is unsubstituted or substituted with 1 or substituents independently selected from hydroxy, halogen, $(C_1-C_6)$alkyl, $(C_1-C_6)$alkoxy, halo$(C_1-C_6)$alkyl, halo $(C_1-C_6)$alkoxy; and
(iii) groups of the formula

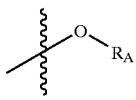

wherein $R_A$ is 5- to 7-membered cycloalkyl, heterocycloalkyl, aryl or heteroaryl, each of which is unsubstituted or substituted with 1 or 2 substituents independently selected from hydroxy, halogen, $(C_1-C_6)$alkyl, halo$(C_1-C_6)$alkyl, $(C_1-C_6)$alkoxy, halo$(C_1-C_6)$alkoxy;

$R_5$ represents hydrogen, halogen, $(C_1-C_6)$alkyl, $(C_3-C_8)$cycloalkyl, $(C_3-C_8)$cycloalkyl$(C_1-C_6)$alkyl, phenyl, benzyl, thiophenyl, thiazolyl, pyridyl, imidazolyl, pyrazolyl, or pyrimidinyl;

$R_6$ and $R_7$ independently represent hydrogen, fluorine, or $C_1-C_6$alkyl; and W represents phenyl, thienyl, thiazolyl, pyridyl, imidazolyl, pyrazolyl, isoxazolyl, or pyrimidinyl, each of which is unsubstituted or substituted with from 1 to 4 groups independently selected from $R_{30}$.

23. A compound or salt according to claim 22, wherein $R_5$ represents hydrogen, halogen, or $(C_1-C_6)$alkyl.

24. A compound or salt according to claim 23, wherein
R$_5$ represents hydrogen, halogen, or (C$_1$–C$_6$)alkyl; and
W represents phenyl, 2-thiazoyl, or 2-pyridyl, each of which is unsubstituted or substituted with from 1 to 4 groups independently selected from R$_{30}$.

25. A compound or salt according to claim 24, wherein R$_1$ and R$_4$ are independently selected from hydrogen, halogen, methyl, ethyl, methoxy, and ethoxy.

26. A compound or salt according to claim 3 of the formula:

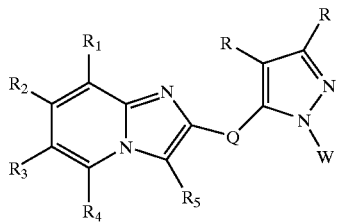

27. A compound or salt according to claim 26, wherein Q is C(R$_6$)(R$_7$).

28. A compound or salt according to claim 27, wherein:
each R is independently selected from the group consisting of
(i) hydrogen, halogen, (C$_1$–C$_6$)alkyl, (C$_3$–C$_8$)cycloalkyl, (C$_3$–C$_8$)cycloalkyl(C$_1$–C$_6$)alkyl, (C$_1$–C$_6$)alkoxy, halo(C$_1$–C$_6$)alkyl and halo(C$_1$–C$_6$)alkoxy, and
(ii) phenyl and pyridyl, each of which is unsubstituted or substituted with from 1 to 3 substituents independently chosen from halogen, hydroxy, C$_1$–C$_4$alkyl, and C$_1$–C$_4$alkoxy;
R$_1$, R$_2$, R$_3$, and R$_4$ are independently selected from:
(i) hydrogen, halogen, hydroxy, nitro, cyano and amino;
(ii) (C$_1$–C$_6$)alkyl, (C$_1$–C$_6$)alkoxy, (C$_1$–C$_6$)alkanoyl, (C$_1$–C$_6$)alkyl ether, (C$_3$–C$_8$)cycloalkyl, (C$_3$–C$_8$)cycloalkyl(C$_1$–C$_6$)alkyl, (C$_2$–C$_6$)alkenyl, (C$_2$–C$_6$)alkynyl, 3- to 8-membered heterocycloalkyl, 3- to 8-membered heteroaryl, halo(C$_1$–C$_6$)alkyl, halo(C$_1$–C$_6$)alkoxy, mono and di(C$_1$–C$_6$)alkylamino, amino(C$_1$–C$_6$)alkyl, and mono- and di(C$_1$–C$_6$)alkylamino(C$_1$–C$_6$)alkyl, each of which is unsubstituted or substituted with 1 or substituents independently selected from hydroxy, halogen, (C$_1$–C$_6$)alkyl, (C$_1$–C$_6$)alkoxy, halo(C$_1$–C$_6$)alkyl, halo(C$_1$–C$_6$)alkoxy; and (iii) groups of the formula

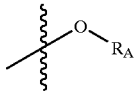

wherein R$_A$ is 5- to 7-membered cycloalkyl, heterocycloalkyl, aryl or heteroaryl, each of which is unsubstituted or substituted with 1 or 2 substituentS independently selected from hydroxy, halogen, (C$_1$–C$_6$)alkyl, halo(C$_1$–C$_6$)alkyl, (C$_1$–C$_6$)alkoxy, halo(C$_1$–C$_6$)alkoxy;
R$_5$ represents hydrogen, halogen, (C$_1$–C$_6$)alkyl, (C$_3$–C$_8$)cycloalkyl, (C$_3$–C$_8$)cycloalkyl(C$_1$–C$_6$)alkyl, phenyl, benzyl, thiophenyl, thiazolyl, pyridyl, imidazolyl, pyrazolyl, or pyrimidinyl;
R$_6$ and R$_7$ independently represent hydrogen, fluorine, or C$_1$–C$_6$ alkyl; and
W represents phenyl, thienyl, thiazolyl, pyridyl, imidazolyl, pyrazolyl, isoxazolyl, or pyrimidinyl, each of which is unsubstituted or substituted with from 1 to 4 R$_{30}$ groups.

29. A compound or salt according to claim 28, wherein R$_5$ represents hydrogen, halogen, or (C$_1$–C$_6$)alkyl.

30. A compound or salt according to claim 29, wherein W represents phenyl, 2-thiazoyl, or 2-pyridyl, each of which is unsubstituted or substituted with from 1 to 4 groups independently selected from R$_{30}$.

31. A compound or salt according to claim 28, wherein R$_1$ is selected from hydrogen, halogen, methyl, ethyl, methoxy, and ethoxy.

32. A pharmaceutical composition comprising a compound or salt according to claim 1 combined with a pharmaceutically acceptable carrier or excipient.

* * * * *